United States Patent
Andou et al.

(12) 
(10) Patent No.: US 6,187,223 B1
(45) Date of Patent: Feb. 13, 2001

(54) POLYHALOALKYL ETHER DERIVATIVES AS WELL AS LIQUID CRYSTAL COMPOSITIONS AND LIQUID CRYSTAL DISPLAY ELEMENTS CONTAINING THEM

(75) Inventors: Tugumiti Andou, Kumamotoken; Koichi Shibata, Chibaken; Shuichi Matsui, Chibaken; Kazutoshi Miyazawa, Chibaken; Hiroyuki Takeuchi, Chibaken; Yasusuke Hisatsune, Chibaken; Fusayuki Takeshita, Chibaken; Etsuo Nakagawa, Chibaken; Katsuhiko Kobayashi, Chibaken; Yoshitaka Tomi, Chibaken, all of (JP)

(73) Assignee: Chisso Corporation, Osaka (JP)

( * ) Notice: Under 35 U.S.C. 154(b), the term of this patent shall be extended for 0 days.

(21) Appl. No.: 09/335,783

(22) Filed: Jun. 18, 1999

Related U.S. Application Data

(62) Division of application No. 08/966,455, filed on Nov. 7, 1997, now Pat. No. 6,007,740.

(30) Foreign Application Priority Data

Nov. 22, 1996 (JP) .................................... 8-327854
Oct. 15, 1997 (JP) .................................... 9-297678

(51) Int. Cl.$^7$ .......................... C09K 19/30; C09K 19/12; C09K 19/20; C09K 19/00
(52) U.S. Cl. ............... 252/299.63; 252/299.66; 252/299.67; 252/299.61; 428/1.1
(58) Field of Search ................. 252/299.63, 299.67, 252/299.66, 299.61

(56) References Cited

U.S. PATENT DOCUMENTS

| | | | |
|---|---|---|---|
| 4,606,845 | 8/1986 | Römer et al. | 252/299.63 |
| 5,032,313 | 7/1991 | Goto et al. | 252/299.63 |
| 5,045,229 | 9/1991 | Bartmann et al. | 252/299.01 |
| 5,324,449 | 6/1994 | Kurmeier et al. | 252/299.01 |
| 5,480,581 | 1/1996 | Plach et al. | 252/299.63 |
| 5,536,442 | 7/1996 | Reiffenrath et al. | 252/299.01 |
| 5,589,102 | 12/1996 | Bartmann et al. | 252/299.01 |
| 5,679,746 | 10/1997 | Shimizu et al. | 252/299.61 |
| 5,728,319 | 3/1998 | Matsui et al. | 252/299.63 |
| 5,792,386 | 8/1998 | Matsui et al. | 252/299.01 |
| 5,961,881 | * 10/1999 | Andou et al. | 252/299.63 |

FOREIGN PATENT DOCUMENTS

| | | |
|---|---|---|
| 4113310 | 10/1991 | (DE) . |
| 4142519 | 8/1992 | (DE) . |
| 19531165 | 3/1996 | (DE) . |
| 0360521 | 3/1990 | (EP) . |
| 0640578 | 3/1995 | (EP) . |
| 2-233626 | 9/1990 | (JP) . |
| 2-40048 | 9/1991 | (JP) . |
| WO88/08441 | 11/1988 | (WO) . |
| WO94/03558 | 2/1994 | (WO) . |
| WO96/11994 | 4/1996 | (WO) . |

\* cited by examiner

Primary Examiner—C. H. Kelly
(74) Attorney, Agent, or Firm—Wenderoth, Lind & Ponack, L.L.P.

(57) ABSTRACT

A compound expressed by the general formula (1):

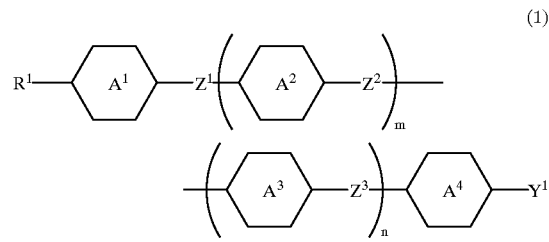

wherein $R^1$ denotes an alkyl group having from 1 to 20 carbon atoms in which one or more methylene groups in said group may be replaced by oxygen atoms or —CH=CH— and one or more hydrogen atoms in said group may be replaced by flourine or chlorine atoms, with the proviso that two or more methylene groups may not be continuously replaced by oxygen atoms, $Y^1$ denotes an alkoxy group having 1 to 5 carbon atoms, in which at least one hydrogen atom is replaced by a fluorine atom and one or more hydrogen atoms may be further replaced by chlorine atoms, $Z^1$, $Z^2$ and $Z^3$ each independently denote a covalent bond, —$CH_2CH_2$—, —CH=CH—, —COO— or —$CF_2$—, with the proviso that at least one of $Z^1$, $Z^2$ and $Z^3$ is —COO— or —$CF_2O$—, rings $A^1$, $A^2$, $A^3$ and $A^4$ each independently denote trans-1,4-cyclohexylene, 3-cyclohexen-1,4-ylene, 3-fluoro-3-cyclohexen-1,4-ylene, pyrimidine-2,5-diyl, 1,3-dioxan-2,5-diyl, trans-1-sila-1,4-cyclohexylene, trans-4-sila-1,4-cyclohexylene, or 1,4-phenylene in which one or more hydrogen atoms may be replaced by fluorine atoms or chlorine atoms, and m and n denote 0 or 1, with the proviso that when $Z^1$, $Z^2$ or $Z^3$ is —$CF_2O$—, then at least two groups selected from rings $A^1$, $A^2$, $A^3$ and $A^4$ directly bonded to —$CF_2O$— are both 1,4-phenylene in which one or more hydrogen atoms may be replaced by fluorine atoms or chlorine atoms, and any of the rings $A^1$, $A^2$ and $A^3$ bonded with the carbon atoms of —$CF_2O$— is 1,4-phenylene in which at least one hydrogen atom is replaced by fluorine or chlorine atoms.

19 Claims, No Drawings

POLYHALOALKYL ETHER DERIVATIVES AS WELL AS LIQUID CRYSTAL COMPOSITIONS AND LIQUID CRYSTAL DISPLAY ELEMENTS CONTAINING THEM

This application is a divisional application of Ser. No. 08/966,455 filed Nov. 7, 1997 now U.S. Pat. No. 6,007,740.

TECHNICAL FIELD

An object of the present invention is to provide a novel liquid crystalline compound which expressed physical properties suitably as an electrooptic display material, a liquid crystal composition having preferable physical properties by use of the above-mentioned novel liquid crystalline compound, and a liquid crystal display element by use of the said liquid crystal composition. In particular, the invention relates to a novel liquid crystalline compound having the following eight characteristics:

1) to have good compatibility with other liquid crystalline compound,
2) to have high dielectric anisotropic value ($\Delta\epsilon$),
3) to have suitable magnitude of refractive anisotropic value ($\Delta n$),
4) to have low viscosity,
5) to have high-speed responsibility,
6) to have low threshold voltage,
7) to be stable physically and chemically, and to be highly reliable,
8) to have a wide temperature range which shows a nematic liquid crystal phase.

Further, the invention relates to a novel liquid crystal composition having good characteristics obtained by use of the said novel liquid crystalline compound.

BACKGROUND ART

Liquid crystal display elements which utilize optical anisotropy and dielectric anisotropy of liquid crystal materials have been used in watches, electric computers, word processor, and television sets etc, and consumption thereof has a tendency to increase year by year. A liquid crystal phase is positioned between a solid phase and a liquid phase, and classified roughly into a nematic phase, a smectic phase and a cholesteric phase. Amongst them, display elements utilizing nematic phases are most widely used. On one hand, although many display modes have been planned hitherto, three modes such as TN display mode, STN display mode and TFT display mode are now main current. Further, as driving modes, a static driving mode, a time-division driving mode, an active matrix driving mode and two-frequency driving mode etc. are known.

Recently, display elements are required to have higher display properties, and thus there have been increased needs for display elements of active matrix driving modes, typically TFT display mode. Liquid crystal materials used in any type of display elements should be stable to external environment factors such as moisture, air, heat and light, express liquid crystal phase in a temperature range as wide as possible which entering around the room temperature, and have low viscosity, low driving voltage, large $\Delta\epsilon$ and optimum $\Delta n$. There is, however, no compound presently which satisfied all these conditions as a single compound, and thus liquid crystal compositions obtained by mixing several liquid crystalline compound or non-liquid crystalline compounds are used now.

One of the characteristics particularly required for liquid crystal display elements of TFT display mode is that display plane has high contrast. Therefore the liquid crystal material used for this object is required to have high specific resistant value, i.e. high voltage holding ratio (V.H.R.) in addition to the above-mentioned conditions. Further, liquid crystal display elements of TFT display mode are required to have low voltage driving, and liquid crystal compositions having higher $\Delta\epsilon$ than conventionally used liquid crystal materials are necessary to satisfy the needs.

In liquid crystalline compounds generally known, those having cyano group are dominant, for which there are problems such as drastical lowering of voltage holding ratio at a high temperature because of large temperature dependency of voltage holding ratio, in the case of using such compounds in liquid crystal display elements of TFT display mode, Therefore, liquid crystalline compounds containing cyano group are not generally used in liquid crystal display elements of TFT display mode, in spite of having high $\Delta\epsilon$. In order to improve it, liquid crystal materials having high $\Delta\epsilon$ while showing high specific resistant value have been developed. As liquid crystalline compounds having high specific resistant values, fluorine type compounds are suitable, These compounds, in general liquid crystalline compounds having (a) fluorine atom(s) as (a) substituent (s), are known as described below. For example, compounds expressed by the following formula (10) are disclosed in Japanese Patent Publication Hei 02-40048.

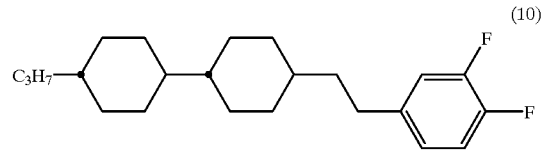

The said compounds (10) have been used industrially, because of having higher specific resistant values than compounds with cyano group, but they cannot realize sufficient low-voltage driving because of low $\Delta\epsilon$ such as about 4.

As compounds having higher $\Delta\epsilon$ than the above-mentioned compounds (10), compounds having trifluorophenyl group as partial structure expressed by the following formula (11) are disclosed in Japanese Patent Application Laid-open Hei 02-233626.

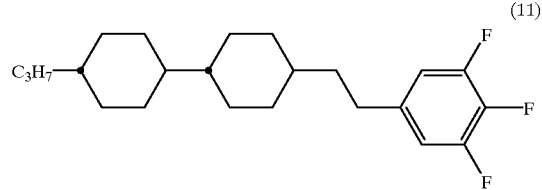

The said compounds, however, have not sufficient $\Delta\epsilon$ such as about 8, and also have more fluorine atom(s) introduced than the above-mentioned compounds of the formula (10) and thus have narrower temperature range of liquid crystal phase than (10), so that they are not suitable for use as one component of liquid crystal composition. Further, considering a clear point, 1-(trans-4-(trans-4-propylcyclohexyl)cyclohexyl)-2-(3,4,5-trifluorophenyl)ethane (11) has a point about 60° C. lower than the corresponding monofluoro compound, that is, 1-(trans-4-(trans-4-propylcyclohexyl)cyclohexyl)-2-(4-fluorophenyl)ethane, and about 25° C. lower than the corresponding difluoro compound, that is, 1-(trans-4-(trans-4-propylcyclohexyl)cyclohexyl)-2-(3,4-difluorophenyl)ethane (10), respectively.

Further, compounds expressed by the formulae (12) and (13) are disclosed in Japanese-translated PCT Patent Applications Laid-open Hei 5-501735 and 2-501311.

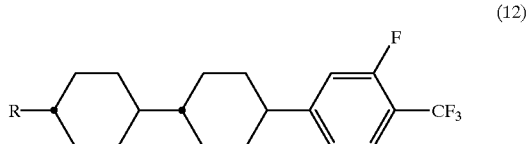

(12)

(13)

These compounds have relatively high Δε (for example Δε of the compound (13) being about 7), but their compatibility at a low temperature with the existing liquid crystalline compounds is very poor, so that they are not suitable for a constituting component of a liquid crystal composition, In order to improve the said compatibility, compounds having (a) fluorine atom(s) introduced in R, i.e. an alkyl group, as disclosed in Japanese-translated PCT Patent application Laid-open Hei 04-506817. The disclosed compound is 2- or 3-cyclic compound having terminal cyclohexyl group and phenyl group, such as the compound expressed by the following formula (14). Derivatives having covalent bonds as bonding groups are only disclosed and there is not disclosed any derivative with other bonding group such as 1,2-ethylene group. Further, (a) substituent(s) on the above-mentioned terminal phenyl group is(are) limited to (a) fluorine atom(s), and there is no description about other substituents such as fluoroalkyl group or fluoroalkoxy group, and also their presences cannot be read from the specification.

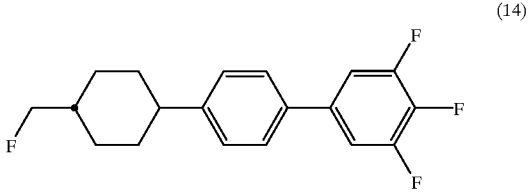

(14)

Further, such compounds have not improve compatibility, particularly the compound of the formula (14) does not express any liquid crystal phase, Therefore, a compound having high Δε and good compatibility has not being known yet, and in the case of using the liquid crystalline compound with high Δε as a composition component, the mixing ratio cannot be increased and the magnitude in Δε of the composition may be limited under the present conditions. Therefore, a liquid crystalline compound having excellent compatibility with conventional liquid crystalline compounds has been waited.

An object of the present invention is to solve the above-mentioned disadvantages of the prior arts and provide a novel liquid crystalline compound which has a wide temperature range of liquid crystals, low threshold voltage, high stability and superior compatibility with other liquid crystal compounds, a liquid crystal composition containing the said compound, as well as a liquid crystal display element by use of the said composition.

DISCLOSURE OF INVENTION

We inventors investigated in order to solve the above-mentioned problems, and found compounds having novel structures and superior characteristics compared to the known liquid crystalline compositions.

That is, the present invention has the following structures [1] to [27].

[1] A compound expressed by the general formula (1):

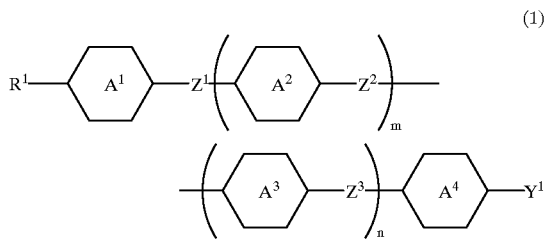

(1)

(wherein, $R^1$ denotes an alkyl group having from 1 to 20 carbon atom(s), in which one or more methylene group (s), in the said group may be substituted by (an) oxygen atom(s), —NR— (R being H or $CH_3$) or —CH=CH— and one or more hydrogen atom(s) in the said group may be substituted by (a) fluorine atom(s) or (a) chlorine atom(s), with the proviso that tow or more methylene groups may not be continuously substituted by oxygen atoms, $Y^1$ denotes a halogen atom, CH, $CF_3$, $CHF_2$ or an alkoxy group having 1 to 5 carbon atom(s), in which at least one hydrogen atom is substituted by a fluorine atom and one or more hydrogen atom(s) may be further substituted by (a) chlorine atom(s), $Z^1$, $Z^2$ and $Z^3$ denote each independently a covalent bond, —$CH_2CH_2$—, —CH=CH—, —COO— or —$CF_2O$—, with the proviso that at least one of $Z^1$, $Z^2$ and $Z^3$ is —COO— or —$CF_2O$—, rings $A^1$, $A^2$, $A^3$ and $A^4$ denote each independently trans-1,4-cyclohexylene, 3-cyclohexen-1,4-ylene, 3-fluoro-3-cyclohexen-1,4-ylene, pyrimidine-2,5-diyl, 1,3-dioxan-2,5-diyl, trans-1-sila-1,4-cyclohexylene, trans-4-sila1,4-cyclohexylene, or 1,4-phenylene in which one or more hydrogen atom(s) may be substituted by (a) fluorine atom(s) or (a) chlorine atom(s), m and n denote 0 or 1, with the proviso that (a) when $Z^1$, $Z^2$ or $Z^3$ is —$CF_2O$— and two groups selected from rings $A^1$, $A^2$, $A^3$ and $A^4$ directly bonded to them are 1,4-phenylene groups in which (a) hydrogen atom(s) may be substituted by (a) fluorine atom(s), then $Y^1$ denotes an alkoxy group having form 2 to 5 carbon atoms in which at least one hydrogen atom is substituted by a fluorine atom and one or more hydrogen atom(s) may be further substituted (a) chlorine atom(s), and (b) when $Z^1$, $Z^2$ or $Z^3$ is —COO—, then $Y^1$ denotes an alkoxy group having from 2 to 5 carbon atoms in which at least one hydrogen atom is substituted by a fluorine atom and one or more hydrogen atom(s) may be further substituted (a) chlorine atom(s), and all atoms which constitute this compound may be substituted by isotopes).

[2] A compound according to item [1], wherein m=n=0 and $Z^1$ is —COO— in the general formula (1).

[3] A compound according to item [1], wherein m=n=0, is —CF$_2$O—, ring $A^1$ is any of trans-1,4-cyclohexylene, 3-cyclohexen-1,4-ylene or 3-fluoro-3-cyclohexen-1,4-ylene, and ring $A^4$ is 1,4phenylene in which (a) hydrogen atom(s) may be substituted by (a) fluorine atom(s) in the general formula (1).

[4] A compound according to item [1], wherein m=n=0 is —CF$_2$O—, ring $A^1$ is trans-1,4-cyclohexylene, and ring $A^4$ is 1,4-phenylene in which (a) hydrogen atom(s) may be substituted by (a) fluorine atom(s) in the general formula (1).

[5] A compound according to item [1], wherein m=1, n=0 and $Z^2$ is —COO— in the general formula (1).

[6] A compound according to item [1], wherein m=1, n=0, $Z^1$ is —CF$_2$O—, and at least one of $A^1$ and $A^2$ is trans-1,4cyclohexylene in the general formula (1).

[7] A compound according to item [6], wherein $A^1$ and $A^2$ are both trans-1,4-cyclohexylene in the general formula (1).

[8] A compound according to item [1], wherein m=1, n=0, $Z^1$ is —CF$_2$O—, and $A^1$ is 3-cyclohexen-1,4ylene or 3-fluoro-3-cyclohexen-1,4-ylene in the general formula (1).

[9] A compound according to item [1], wherein m=1, n=0, $Z^1$ is —CF$_2$O—, and $A^1$ and $A^2$ are both 1,4-phenylen in which one or more hydrogen atom(s) may be substituted by (a) fluorine atoms(s) in the general formula (1).

[10] A compound according to item [1], wherein n=1, n=0, $Z^2$ is —CF$_2$O—, and $A^2$ and $A^4$ are both 1,4-phenylene in which one or more hydrogen atom(s) may be substituted by (a) fluorine atom(s) in the general formula (1).

[11] A compound according to item [1], wherein m=1, n=0, $Z^2$ is —CF$_2$O—, $A^1$ is trans-1,4-cyclohexylene, $A^2$ is any of trans-1,4-cyclohexylene, 3-cyclohexen-1,4ylene or 3-fluoro-3-cyclohexen-1,4-ylene, and $A^4$ is 1,4-phenylene in which one or more hydrogen atom(s) may be substituted by (a) fluorine atom(s) in the general formula (1).

[12] A compound according to item 11, $A^2$ is trans-1,4-cyclohexylene and $Z^1$ is a covalent bond.

[13] A compound according to item [1], wherein m=n=1 and $Z^3$ is —COO— in the general formula (1).

[14] A compound according to item [1], wherein m=n=1, $Z^2$ is —CF$_2$O—, $A^1$ is trans-1,4-cyclohexylene, $A^2$ is any of trans-1,4- cyclohexylene, 3-cyclohexen-1,4-ylene, 3-fluoro-3-cyclohexen-1,4-ylene or 14phenylene in which one or more hydrogen atom(s) may be substituted by (a) fluorine atom(s), and $A^3$ and $A^4$ are both 1,4-phenylene in which one or more hydrogen atom(s) may be substituted by (a) fluorine atom(s) in the general formula (1).

[15] A compound according to item [14], wherein $A^2$ is trans-1,4-cyclohexylene and $Z^3$ is a covalent bond.

[16] A compound according to item [14], wherein $A^2$ is 1,4-phenylene in which one or more hydrogen atom(s) may be substituted by (a) fluorine atom(s) and $Z_3$ is a covalent bond.

[17] A compound according to item [1], wherein m=n=1, $Z^2$ is —CF$_2$O—, $A^1$, $A^2$ and $A^3$ are all trans-1,4-cyclohexylene, and $A^4$ is 1,4-phenylene in which one or more hydrogen atom(s) may be substituted by (a) fluorine atom(s) in the general formula (1).

[18] A compound according to item [1], wherein m=n=1, $Z^3$ is CF$_2$O—, $A^1$ and $A^2$ are both trans-1,4-cyclohexylene, and $A^3$ and $A^4$ are both 1,4-phenylene in which one or hydrogen atom(s) may be substituted by (a) fluorine atom(s) in the general formula (1).

[19] A compound according to item [1], wherein m=n=1, $Z^3$ is —CF$_2$O—, $A^1$ is trans-1,4-cyclohexylene, and $A^2$, $A^3$ and $A^4$ are all 1,4-phenylene in which one or more hydrogen atom(s) may be substituted by (a) fluorine atom(s) in the general formula (1).

[20] A liquid crystal composition consisting of at least two components characterized in that at least one liquid crystalline compound expressed by the general formula (1) according to item [1] is contained.

[21] A liquid crystal composition characterized in that at least one liquid crystalline compound according to item [1] is contained as the first component and that at least one compound selected from the group consisting of compounds having the general formulae (2), (3) and (4) is contained as the second component:

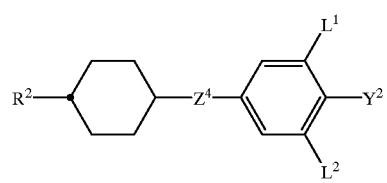

(2)

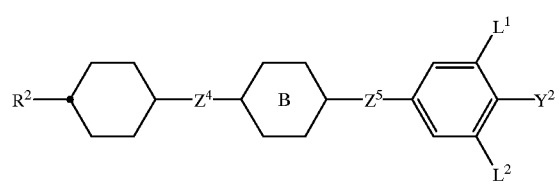

(3)

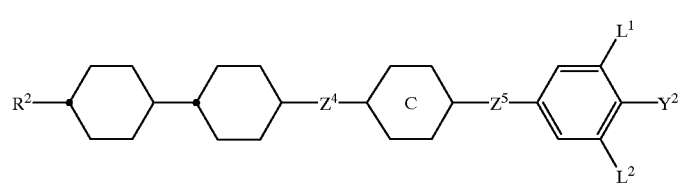

(4)

(wherein, $R^2$ denotes an alkyl group having from 1 to 10 carbon atom(s), in which optional non-adjacent methylene group(s) in the said group may be substituted by (an) oxygen atom(s) or —CH=CH— and optional hydrogen atom(s) in the said group may be substituted by (a) fluorine atom(s), $Y^2$ denotes a fluorine atom, a chlorine atom, $OCF_3$, $OCF_2H$, $CF_3$, $CF_2H$, $CFH_2$, $OCF_2CF_2H$ or $OCF_2CFHCF_3$, $L^1$ and $L^2$ denote each independently a hydrogen atom or a fluorine atom, $Z^4$ and $Z^5$ denote each independently —$CH_2CH_2$—, —CH=CH—, 1,4-butylene group, —COO—, —$CF_2O$—, —$OCF_2$— or a covalent bond, ring B denotes trans-1,4-cyclohexylene, 1,3-dioxane-2,5-diyl, or 1,4-phenylene in which (a) hydrogen atom(s) may be substituted by (a) fluorine atom(s), ring C denotes trans-1,4-cyclohexylene or 1,4-phenylene in which (a) hydrogen atom(s) may be substituted by (a) fluorine atom(s), and all atoms used in the respective formulae may be substituted by isotopes).

[22] A liquid crystal composition characterized in that at least one liquid crystalline compound according to item [1] is contained as the first component and that at least one compound selected from the group consisting of compounds having the general formulae (5) and (6) is contained as the second component:

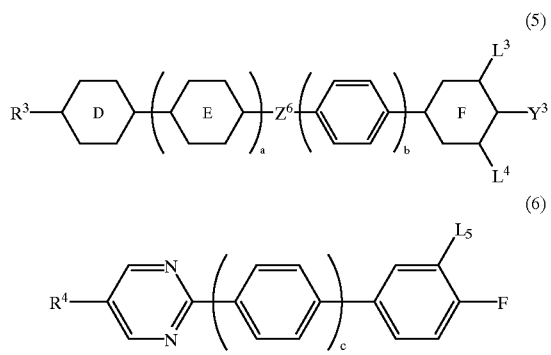

wherein, $R^3$ $R^4$ denote each independently an alkyl group having from 1 to 10 carbon atoms (s), in which optional non-adjacent methylene group(s) in the said group may be substituted by (an) oxygen atom(s) or —CH=CH— and optional hydrogen atom(s) in the said group may be substituted by (a) fluorine atom(s), $Y^3$ denotes CN group or C≡C—CN, ring D denotes trans-1,4-cyclohexylene, 1,4-phenylene, pyrimidine-2,5-diyl or 1,3-dioxane-2,5-diyl, ring E denotes trans-1,4-cyclohexylene, 1,4-phenylene in which (a) hydrogen atom(s) may be substituted by (a) fluorine atom(s), or pyrimidine-2,5-diyl, ring F denotes trans-1,4-cyclohexylene or 1,4-phenylene, $Z^6$ denotes —$CH_2CH_2$—, —COO— or a covalent bond, $L^3$, $L^4$ and $L^5$ denote each independently a hydrogen atom or a fluorine atom, a, b and c denote each independently 0 or 1, and all atoms used in the respective formulae may be substituted by isotopes).

23. A liquid crystal composition characterized in that at least one liquid crystalline compound according to item [1] is contained as the first component and that at least one compound selected from the group consisting of compounds having the general formulae (7), (8) and (9) is contained as the second component:

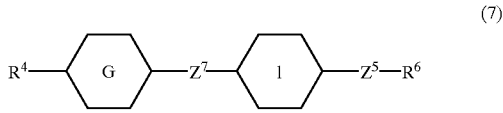

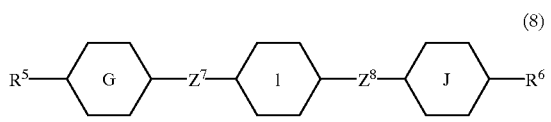

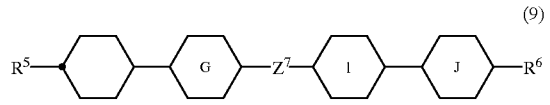

(wherein, $R^5$ and $R^6$ denote each independently an alkyl group having from 1 to 10 carbon atom(s), in which optional non-adjacent methylene group(s) in the said group may be substituted by (an) oxygen atom(s) or —CH=CH— and optional hydrogen atom(s) in the said group may be substituted by (a) fluorine atom(s), ring G, ring I and ring J denote each independently trans-1,4-cyclohexylene, pyrimidine-2,5-diyl or 1,4-phenylene in which one or more hydrogen atom(s) may be substituted by (a) fluorine atom(s), $Z^7$ and $Z^8$ denote each independently —C≡C—, —COO—, —$CH_2CH_2$—, —CH=CH— or a covalent bond, and all atoms used in the respective formulae may be substituted by isotopes).

[24] A liquid crystal composition characterized in that at least one liquid crystalline compound according to item [1] is contained as the first component, that at least one compound selected from the group consisting of compounds having the general formulae (5) and (6) is contained as the second component, and that at least one compound selected from the group consisting of compounds having the general formulae (7), (8) and (9) is contained as the third component.

[25] A liquid crystal composition characterized in that at least one liquid crystalline compound according to item [1] is contained as the first component, that at least one compound selected from the group consisting of compounds having the general formulae (2), (3) and (4) is contained as the second component, that at least one compound selected from the group consisting of compounds having the general formulae (5) and (6) is contained as the third component, and that at least one compound selected from the group consisting of compounds having the general formulae (7), (8) and (9) is contained as the fourth component.

[26] A liquid crystal composition characterized in that one or more optical active compound is (are) further contained in addition to the liquid crystal composition according to any of items [20] to [25].

[27] A liquid crystal display element constituted by use of the liquid crystal composition according to any of items [20] to [26].

Preferable embodiments of compounds expressed by the general formula (1) according to the present invention are the compounds expressed by the following general formulae (1-1) to (1-21), wherein $R^1$ and $Y^1$ have the same meanings as the above-mentioned ones.

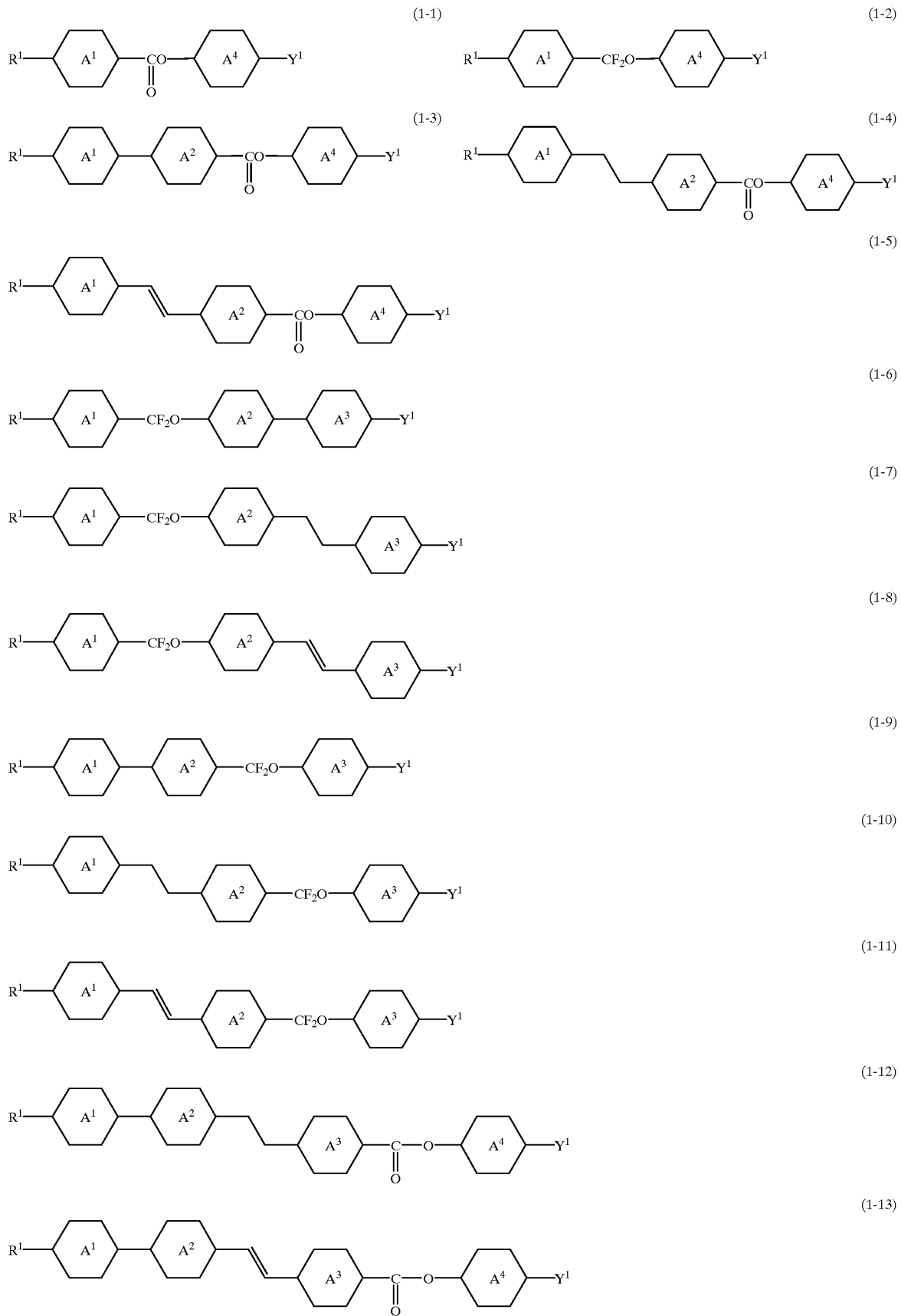

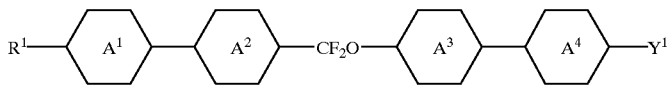
(1-14)
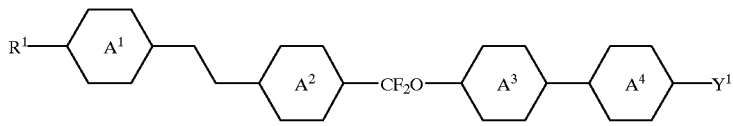
(1-15)
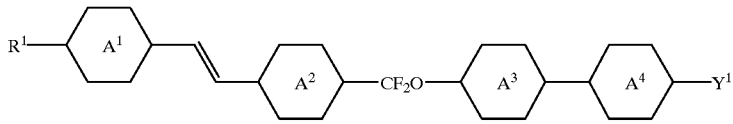
(1-16)
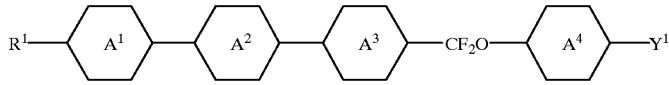
(1-17)
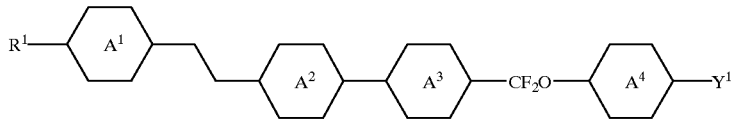
(1-18)
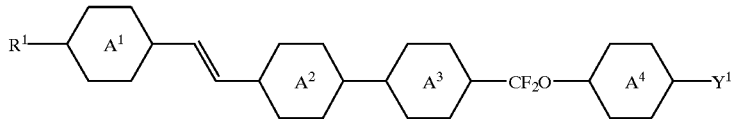
(1-19)
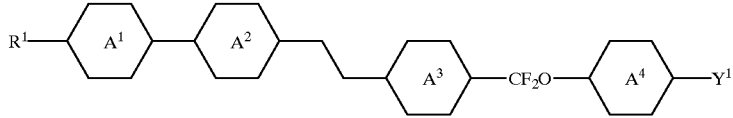
(1-20)
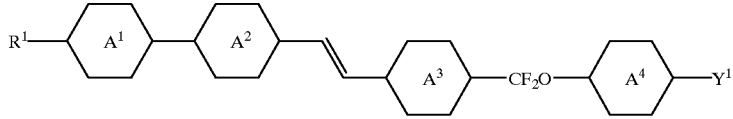
(1-21)
Also, in the case of selecting a structure of rings $A^1$, $A^2$, $A^3$ and $A^4$, the compounds expressed by the following formulae (1-1-1) to (1-21-4) are preferable, wherein $R^1$ and $Y^1$ have the same meanings as the above-mentioned ones and one or more hydrogen atom(s) on 1,4-phenylene in the general formulae may be substituted by (a) halogen atom(s).
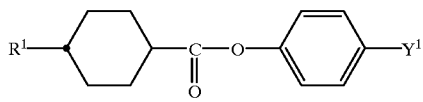
(1-1-1)
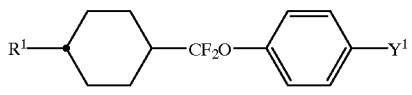
(1-2-1)
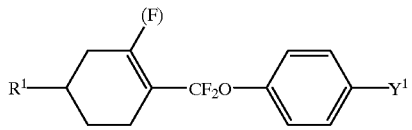
(1-2-2)
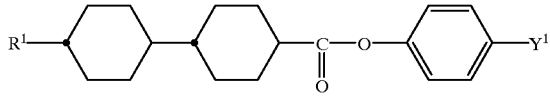
(1-3-1)

(1-3-2)
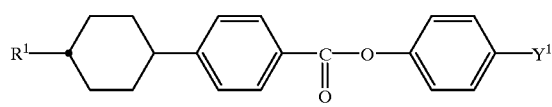
(1-4-1)
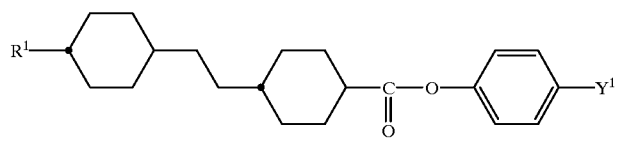
(1-4-2)
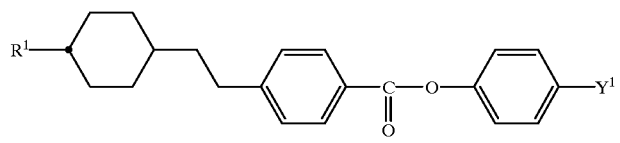
(1-5-1)
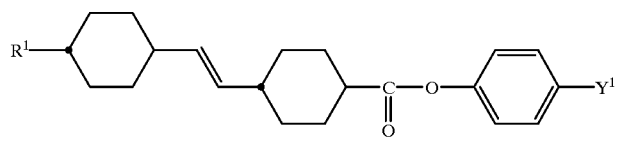
(1-5-2)
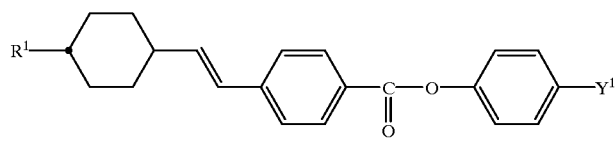
(1-6-1)
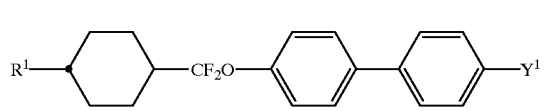
(1-6-2)
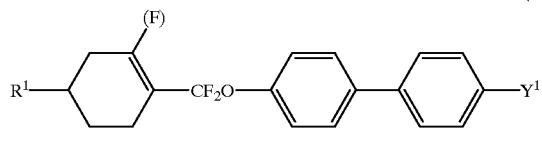
(1-6-3)
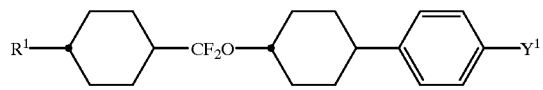
(1-6-4)
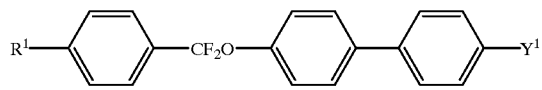
(1-7-1)
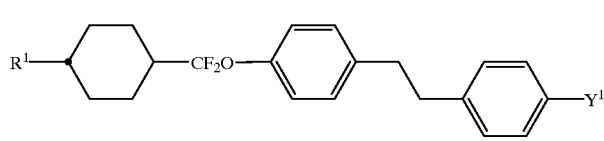
(1-7-2)
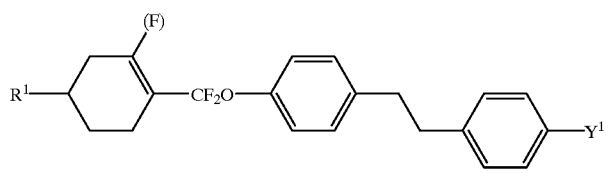
(1-7-3)
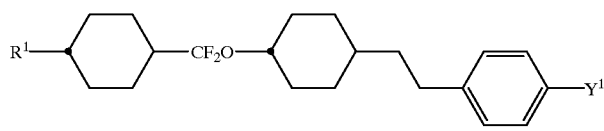

(1-8-1)
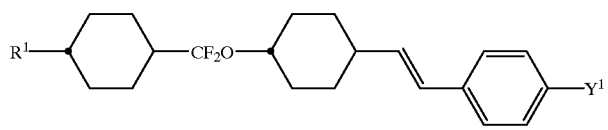
(1-8-2)
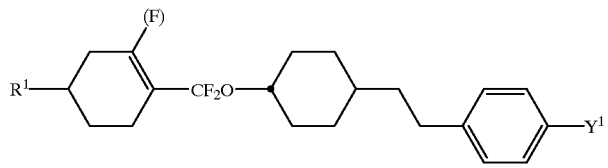
(1-9-1)
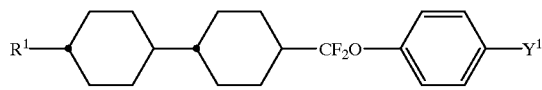
(1-9-2)
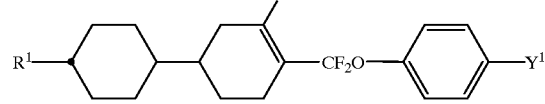
(1-9-3)
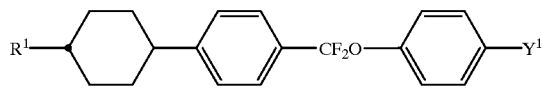
(1-10-1)
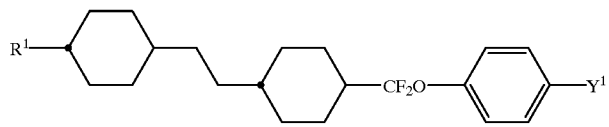
(1-10-2)
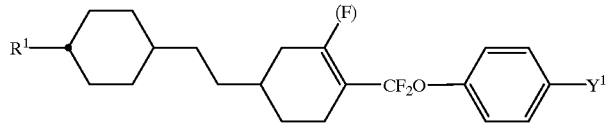
(1-10-3)
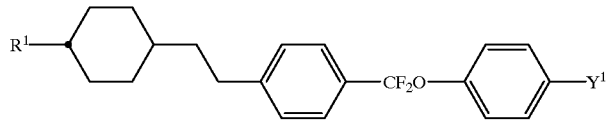
(1-11-1)
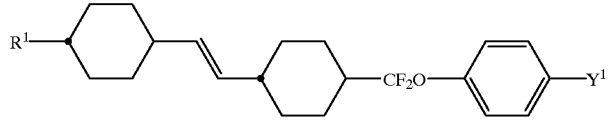
(1-11-2)
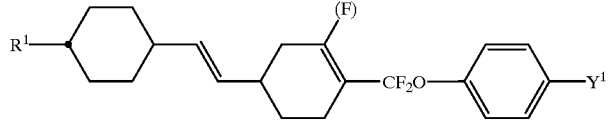
(1-11-3)
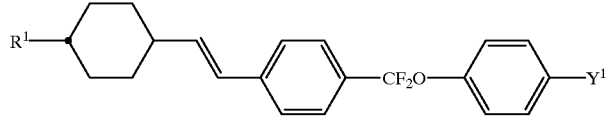

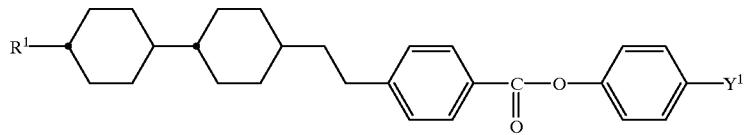
(1-12-1)
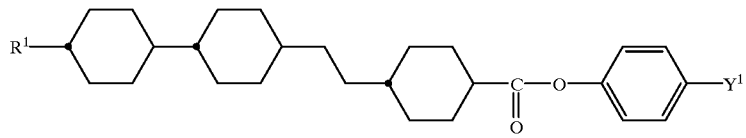
(1-12-2)
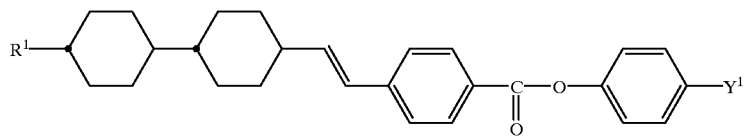
(1-13-1)
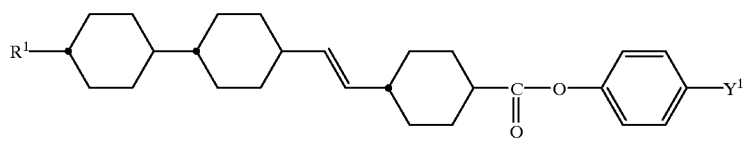
(1-13-2)
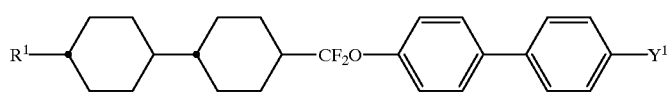
(1-14-1)
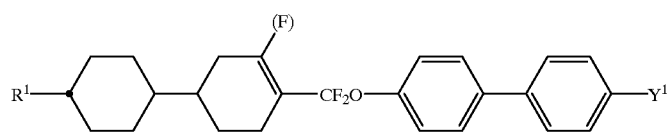
(1-14-2)
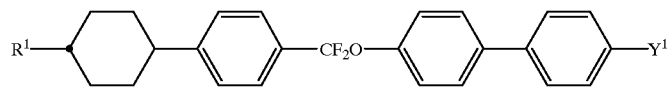
(1-14-3)
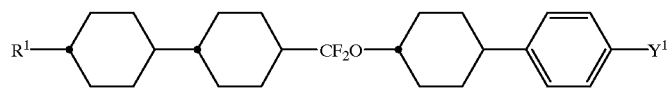
(1-14-4)
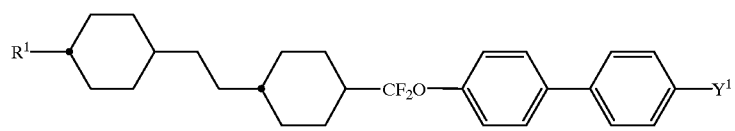
(1-15-1)
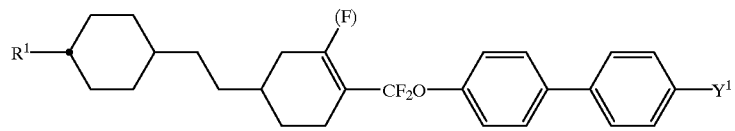
(1-15-2)
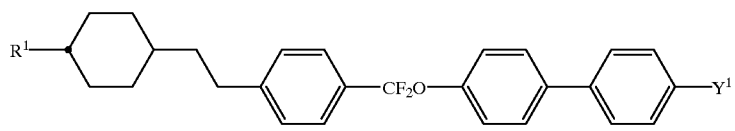
(1-15-3)

-continued
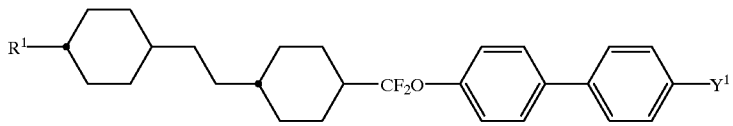
(1-15-4)
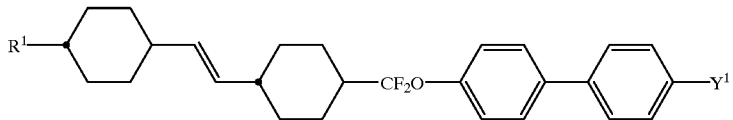
(1-16-1)
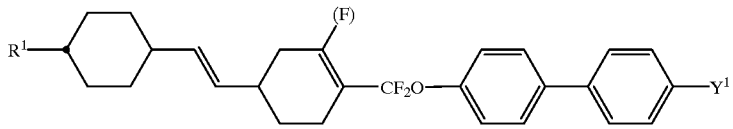
(1-16-2)
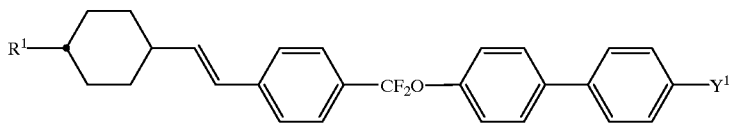
(1-16-3)
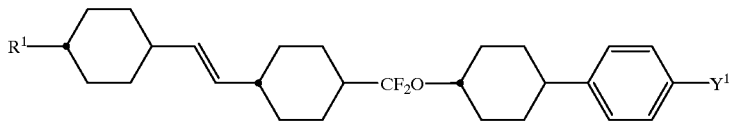
(1-16-4)
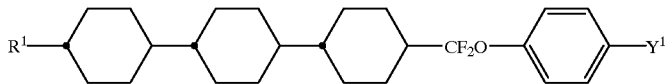
(1-17-1)
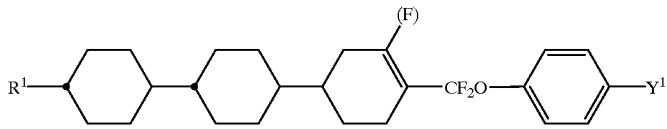
(1-17-2)
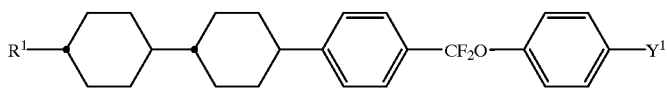
(1-17-3)
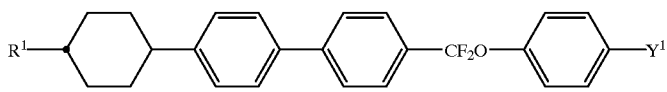
(1-17-4)
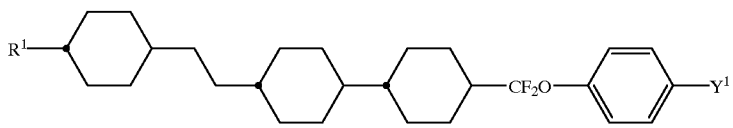
(1-18-1)
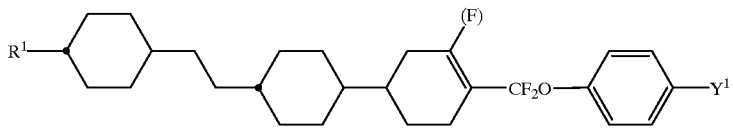
(1-18-2)

-continued
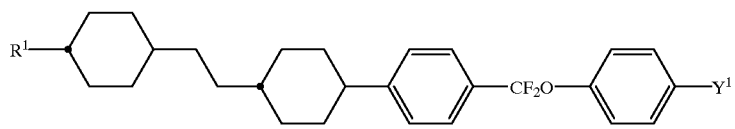 (1-18-3)
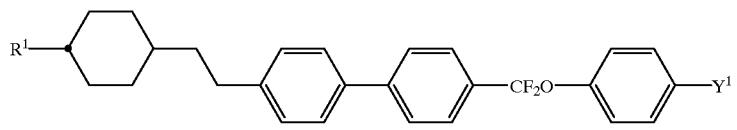 (1-18-4)
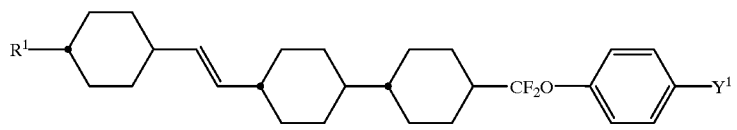 (1-19-1)
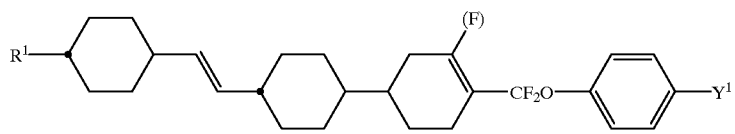 (1-19-2)
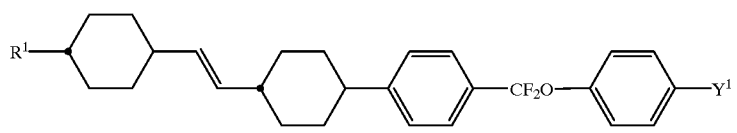 (1-19-3)
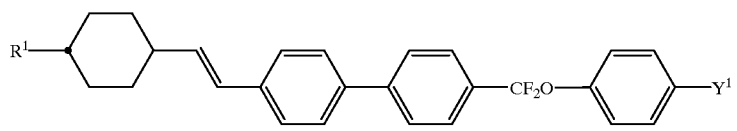 (1-19-4)
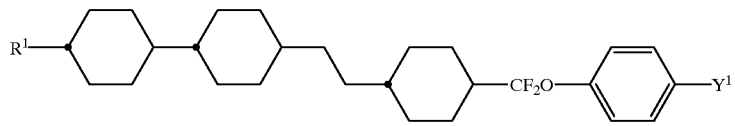 (1-20-1)
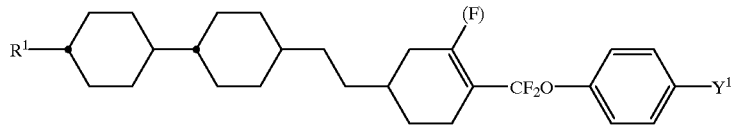 (1-20-2)
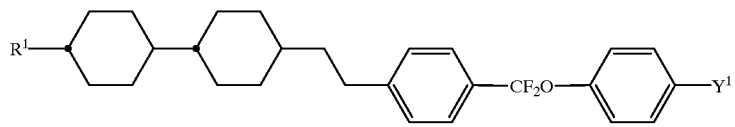 (1-20-3)
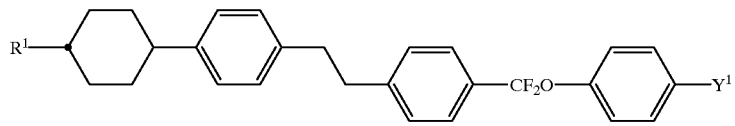 (1-20-4)

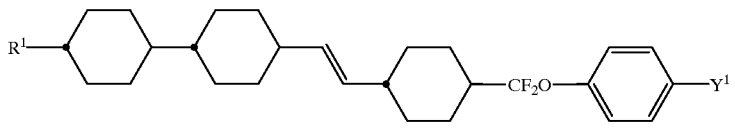
(1-21-1)

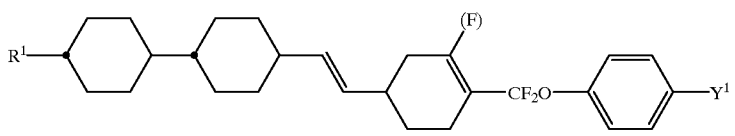
(1-21-2)

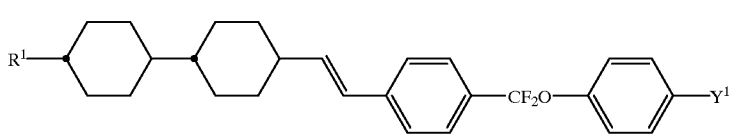
(1-21-3)

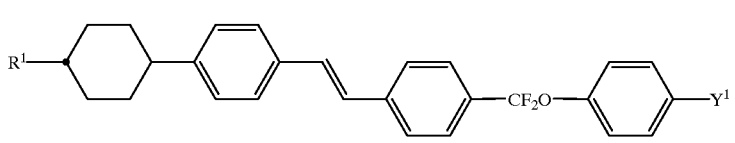
(1-21-4)

These compounds all show preferable characteristics, but more preferable examples of $R^1$ and $Y^1$ are mentioned as follows.

As to $R^1$, the followings are preferable: that is, methyl, ethyl, n-propyl, n-butyl, n-pentyl, n-hexyl, n-heptyl, n-octyl, n-nonyl, n-decyl, methyloxy, ethyloxy, n-propyloxy, n-butyloxy, n-pentyloxy, n-hexyloxy, n-heptyloxy, n-octyloxy, n-nonyloxy, n-decyloxy, methoxymethyl, ethoxymethyl, propoxymethyl, butoxymethyl, methoxyethyl, methoxypropyl, methoxybutyl, ethoxyethyl, ethoxypropyl, propoxyethyl, propoxypropyl, vinyl, 1-propenyl, 1-butenyl, 1-pentenyl, 3-butenyl, 3-pentenyl, allyloxy, ethynyl, 1-propynyl, 1-butynyl, 1-pentynyl, 3-butynyl, 3-pentynyl, trifluoromethyl, difluoromethyl, difluorochloromethyl, 2,2,2-trofluoroethyl, 2-fluoroethyl, 3-fluoropropyl, 4-fluorobutyl, 5-fluoropentyl, 3-chloropropyl, trifluoromethyloxy, difluoromethyloxy, difluorochloromethyloxy, pentafluoroethyloxy, 1,1,2,2-tetrafluoroethyloxy, heptafluoropropyloxy, 1,1,2,3,3,3-hexafluoropropyloxy, trifluormethyloxymethyl, 2-fluoroethenyl, 2,2-difluoroethenyl, 1,2,2-trifluoroethenyl, 3-fluoro-1-butenyl, 4-fluoro-1-butenyl and 3,3,3-trifluoro-1-propynyl etc. may be exemplified.

More preferably, methyl, ethyl, n-propyl, n-butyl, n-pentyl, methyloxy, ethyloxy, n-propyloxy, n-butyloxy, n-pentyloxy, methoxymethyl, ethoxymethyl, methoxyethyl, vinyl, 1-propenyl, 1-butenyl, 3-buenyl, 3-pentenyl, ethynyl, 1-propynyl, 1-butynyl, 3-fluoropropyl and 4-fluorobutyl etc. may be exemplified.

As to $Y^1$, the followings are preferable:

F, Cl, CN, $CF_3$, $CF_2H$, $OCF_3$, $OCF_2H$, $OCFHCF_3$, $OCFHCFH_2$, $OCFHCF_2H$, $OCF_2CH_3$, $OCF_2CFH_2$, $OCF_2CF_2H$, $OCF_2CF_2CF_2H$, $OCF_2CF_2CFH_2$, $OCFHCF_2CF_3$, $OCFHCF_2CF_2H$, $OCFHCFHCF_3$, $OCH_2CF_2CF_3$, $OCF_2CF_2CF_3$, $OCF_2CFHCFH_2$, $OCF_2CH_2$, $OCFHCF_2CFH_2$, $OCFHCFHCF_2H$, $OCFHCH_2CF_3$, $OCH_2CFHCF_3$, $OCH_2CF_2CF_2H$, $OCF_2CFHCH_3$, $OCF_2CH_2CFH_2$, $OCFHCF_2CH_3$, $OCFHCFHCFH_2$, $OCFHCH_2CF_3$, $OCH_2CF_2CFH_2$, $OCH_2CFHCF_2H$, $OCF_2CH_2CH_3$, $OCFHCFHCH_3$, $OCFHCH_2CFH_2$, $OCH_2CF_2CH_3$, $OCH_2CFHCFH_2$, $OCH_2CH_2CF_2H$, $OCFHCH_2CH_3$, $OCH_2CFHCH_3$, $OCH_2CH_2CF_2H$, $OCClFCF_3$, $OCClFCClF_2$, $OCClFCFH_2$, $OCFHCCl_2F$, $OCClFCF_2H$, $OCClFCClF_2$, $OCF_2CClH_2$, $OCF_2CCl_2H$, $OCF_2CCl_2F$, $OCF_2CClFH$, $OCF_2CClF_2$, $OCF_2CF_2CClF_2$, $OCF_2CF_2CCl_2F$, $OCClFCF_2CF_3$, $OCClFCF_2CF_2H$, $OCClFCF_2CClF_2$, $OCClFCFHCF_3$, $OCClFCClFCF_3$, $OCCl_2CF_2CF_3$, $OCClHCF_2CF_3$, $OCClFCF_2CF_3$, $OCClFCClFCF_3$, $OCF_2CClFCFH_2$, $OCF_2CF_2CCl_2F$, $OCF_2CCl_2CF_2H$, $OCF_2CH_2CClF_2$, $OCClFCF_2CFH_2$, $OCFHCF_2CCl_2F$, $OCClFCFHCF_2H$, $OCClFCFHCF_2H$, $OCClFCCl_2FCF_2H$, $OCClFCCl_2CF_3$, $OCFHCCl_2CF_3$, $OCCl_2CFHCF_3$, $OCH_2CClFCF_3$, $OCCl_2CF_2CF_2H$, $OCH_2CF_2CClF_2$, $OCF_2CClFCH_3$, $OCF_2CFHCCl_2H$, $OCF_2CCl_2CFH_2$, $OCF_2CH_2CCl_2F$, $OCClFCF_2CH_3$, $OCFHCF_2CCl_2H$, $OCClFCClFCFH_2$, $OCFHCFHCCl_2F$, $OCClFCH_2CF_3$, $OCFHCCl_2CF_3$, $OCCl_2CF_2CFH_2$, $OCH_2CF_2CCl_2F$, $OCCl_2CFHCF_2H$, $OCClHCClFCF_2H$, $OCF_2CClHCClH_2$, $OCF_2CH_2CCl_2H$, $OCClFCFHCH_3$, $OCF_2CClFCCl_2H$, $OCClFCH_2CFH_2$, $OCFHCCl_2CFH_2$, $OCCl_2CF_2CH_3$, $OCH_2CF_2CClH_2$, $OCCl_2CFHCFH_2$, $OCH_2CClFCFCl_2$, $OCH_2CH_2CF_2H$, $OCClHCClHCF_2H$, $OCH_2CCl_2CF_2H$, $OCClFCH_2CH_3$, $OCFHCH_2CCl_2H$, $OCClHCFHCClH_2$, $OCH_2CFHCCl_2H$, $OCCl_2CH_2CF_2H$, $OCH_2CCl_2CF_2H$ etc. may be exemplified.

More preferably, F, Cl, CN, $CF_3$, $CF_2H$, $OCF_3$, $OCF_2H$, $OCFHCF_3$, $OCFHCFH_2$, $OCFHCF_2H$, $OCF_2CH_3$, $OCF_2CFH_2$, $OCF_2CF_2H$, $OCF_2CF_2CF_2H$, $OCF_2CF_2CFH_2$, $OCFHCF_2CF_3$, $OCFHCF_2CF_2H$, $OCF_2CF_2CF_3$, $OCF_2CF_2CClF_2$, $OCClFCF_2CF_3$ etc. may be exemplified.

The compounds according to the present invention have high $\Delta\epsilon$, good compatibility and low viscosity, and also show high stability, that is, high specific resistant value and a wide liquid crystal temperature range. Therefore, in the case that the compounds according to the invention being used as components of liquid crystal compositions, novel liquid crystal compositions having preferable physical properties can be provided.

The liquid crystalline compounds according to the invention can express physical properties suitable for electrooptic display materials, and can provide liquid crystal compositions having preferable physical properties by use of these novel liquid crystalline compounds.

The compounds according to the invention have high solubility in other liquid crystalline compounds or liquid crystal compositions, so that liquid crystal compositions obtained by using the compounds according to the present invention do not lose their nematic phases at a low temperature (for example −20° C., which being required from practical viewpoint).

The compounds according to the invention have low viscosity, so that they don't increase eminently viscosity of total liquid crystal compositions even if the compounds being used in plenty for the liquid crystal compositions. Further, since a temperature-dependency of viscosity is very low, an increased rate of viscosity due to a temperature decrease is low. By using the liquid crystalline compounds having superior low viscosity, it becomes possible to prepare liquid crystal compositions having high-speed responsibility.

Although all of compounds according to the invention express preferable physical properties, the liquid crystal compositions having the properties according to objects may be prepared by using compounds in which $R^1$, $Z^1$, $Z^2$, $Z^3$, $A^1$, $A^2$, $A^3$, $A^4$ and $Y^1$ in the general formula (1) are suitably selected. That is, in the case that the compounds are used particularly for liquid crystal compositions wherein the liquid crystal temperature range being higher one, the four-cyclic compounds in which m=n=1 may be used, and otherwise, two-cyclic compounds in which m=n=0.

Refractive anisotropic value may be adjusted by selecting $R^1$, $Z^1$, $Z^2$, $Z^3$, $A^1$, $A^2$, $A^3$, $A^4$ and $Y^1$ in the general formula (1) suitably. That is, in the case that high refractive anisotropic value being necessary, the compounds containing much 1,4-phenylene rings may be used, and in the case that low refractive anisotropy value being necessary, the compounds containing much trans-1,4-cyclohexylene rings may be used.

The liquid crystal compositions according to the invention nare illustrated as follows. The liquid crystal compositions according to the invention contain preferably at least one compound expressed by the general formula (1) in such a proportion as 0.1 to 99.9% by weight, for the purpose of expressing superior characteristics.

In more detail, the liquid crystal compositions according to the invention are obtained by introducing the first component containing at least one compound expressed by the general formula (1) and then mixing it with a compound optionally selected from the compound groups expressed by the general formulae (2) to (9) according to the purposes of the liquid crystal compositions in an optional proportion to complete the compositions.

As compounds of the general formulae (2) to (4) used for the invention, the following compounds may be preferably mentioned, wherein $R^2$ and $Y^2$ denote the same meanings as the above-mentioned ones.

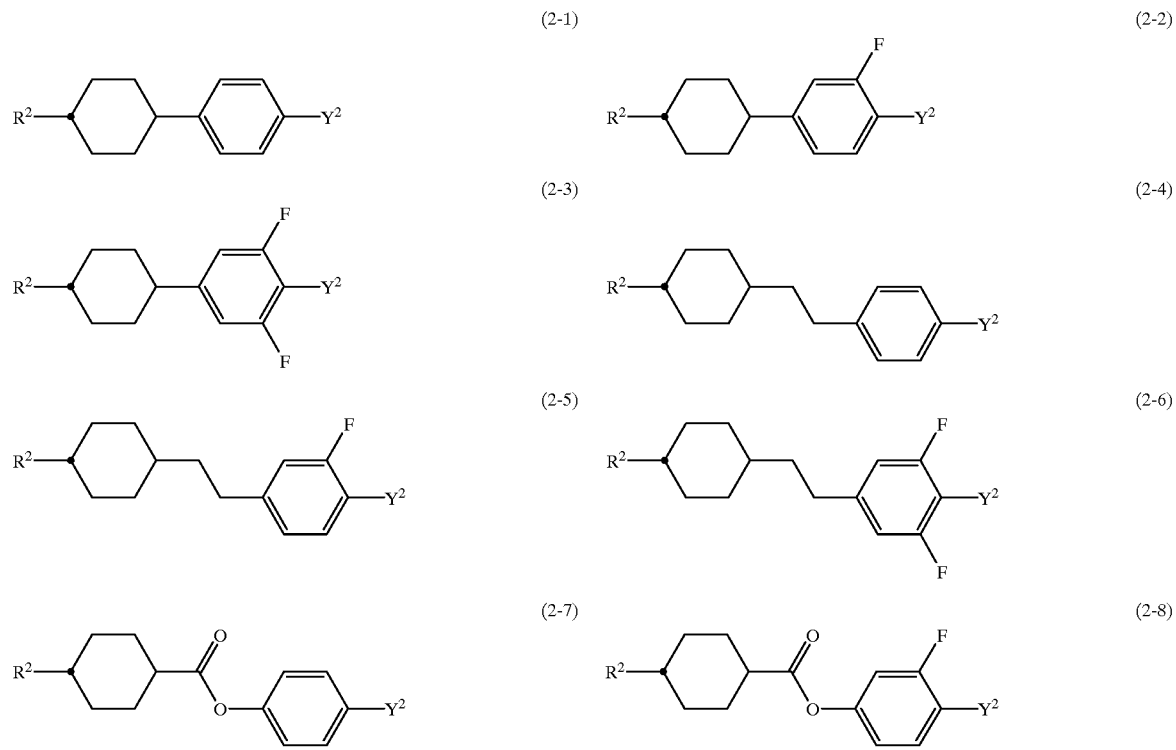

-continued

-continued
(3-16)
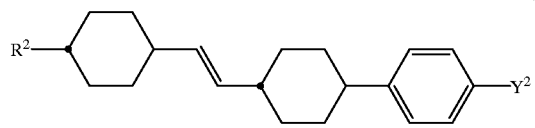
(3-17)
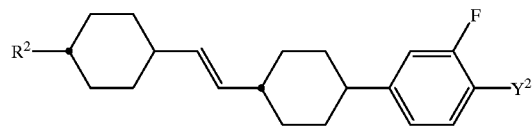
(3-18)
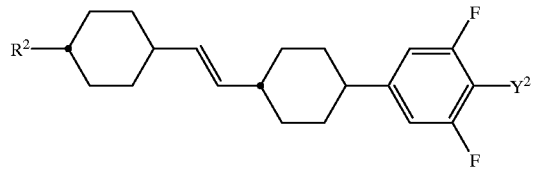
(3-19)
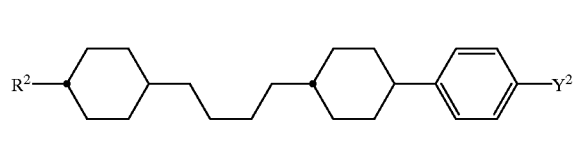
(3-20)
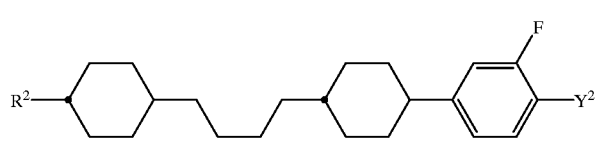
(3-21)
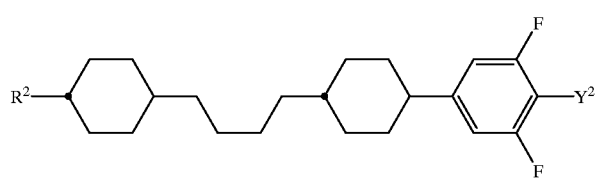
(3-22)
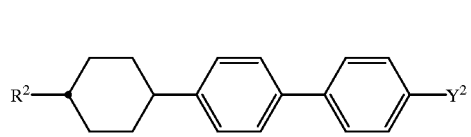
(3-23)
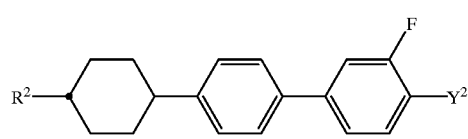
(3-24)
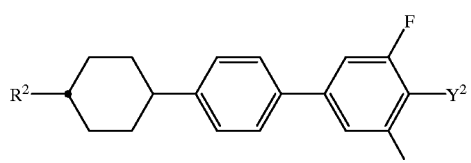
(3-25)
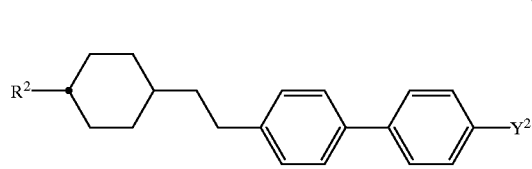
(3-26)
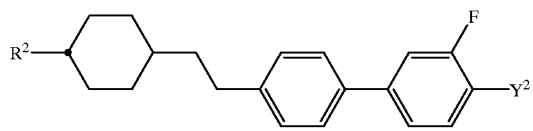
(3-27)
(3-28)
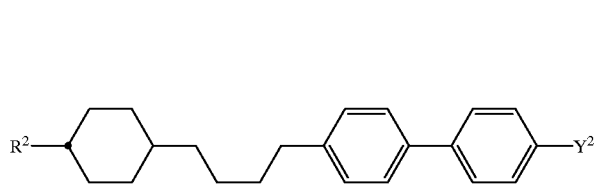
(3-29)
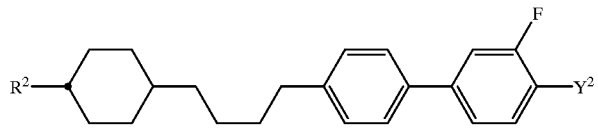

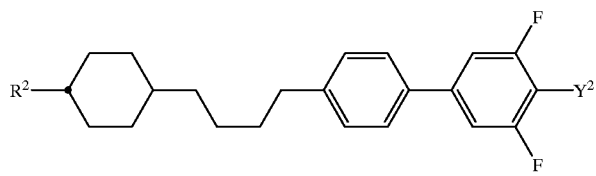
(3-30)
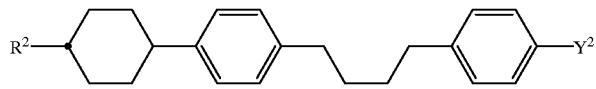
(3-31)
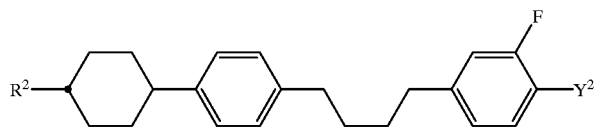
(3-32)
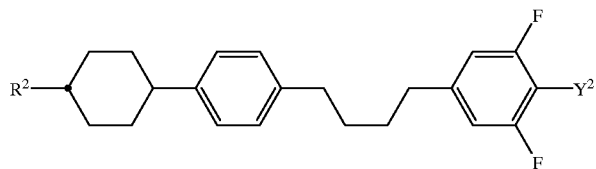
(3-33)
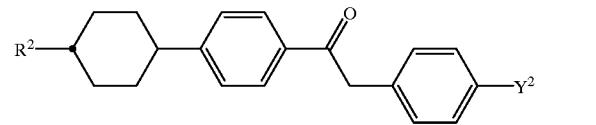
(3-34)
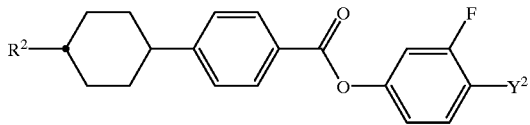
(3-35)
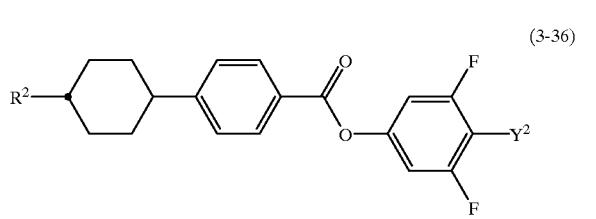
(3-36)
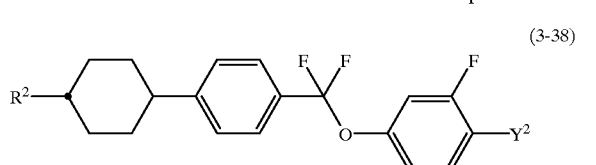
(3-38)
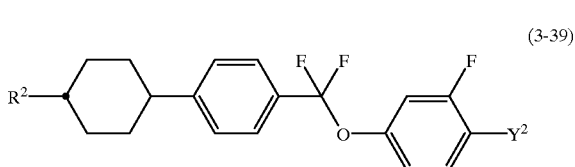
(3-39)
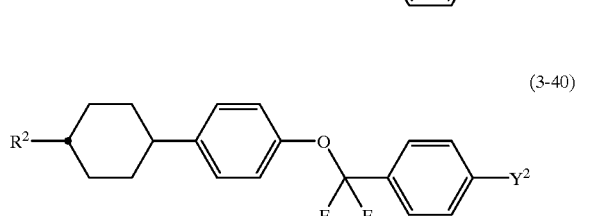
(3-40)
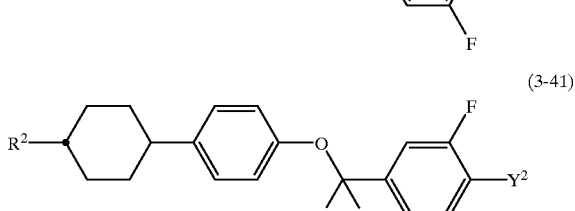
(3-41)
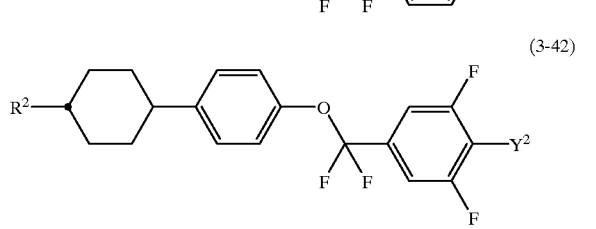
(3-42)
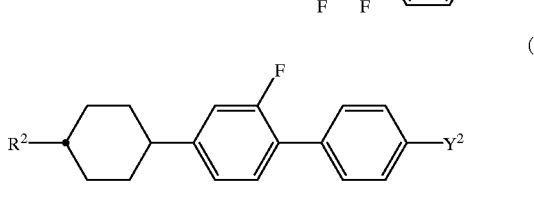
(3-43)

-continued
(3-44)
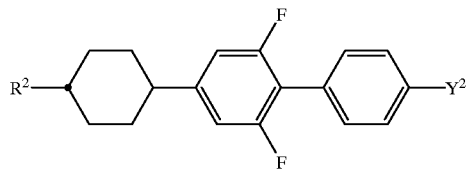
(3-45)
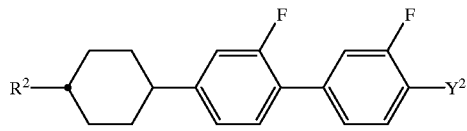
(3-46)
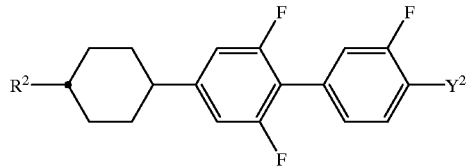
(3-47)
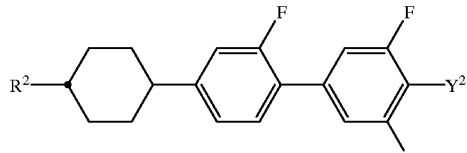
(3-48)
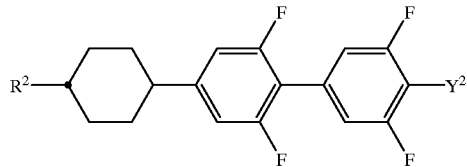
(3-49)
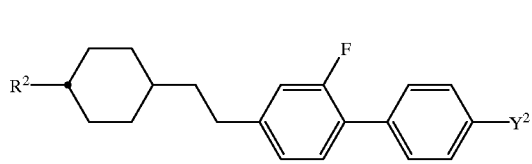
(3-50)
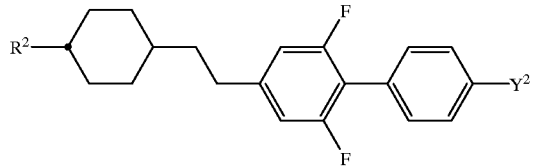
(3-51)
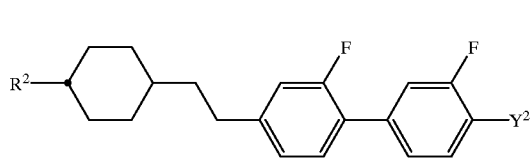
(3-52)
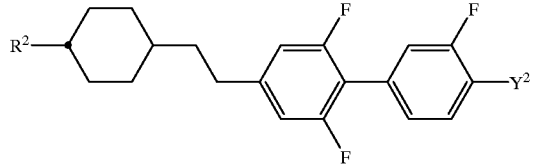
(3-53)
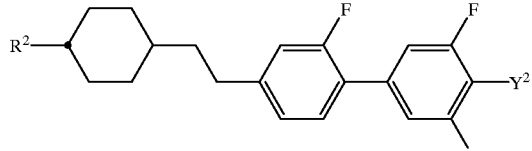
(3-54)
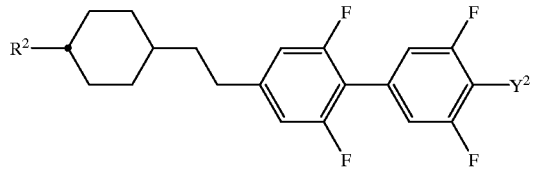
(3-55)
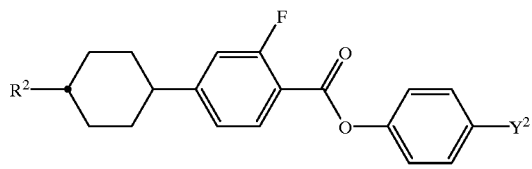
(3-56)
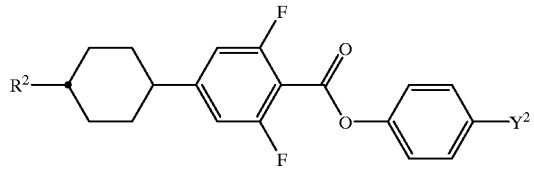
(3-57)
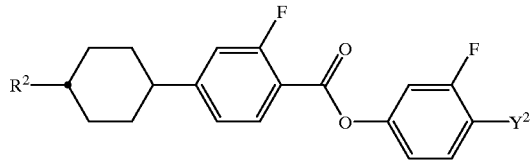
(3-58)
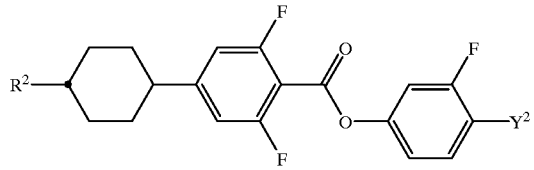
(3-59)
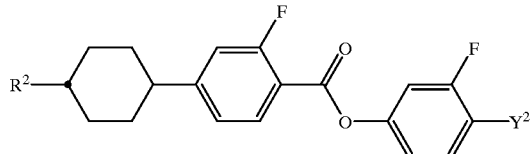

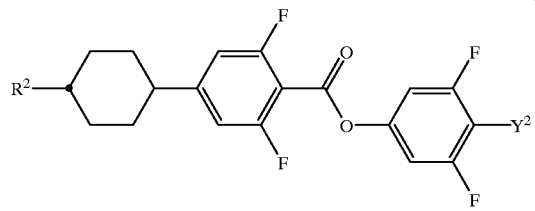
(3-60)
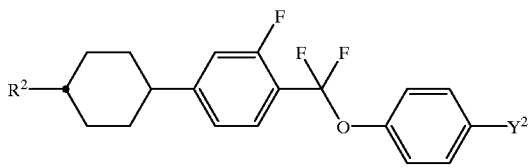
(3-61)
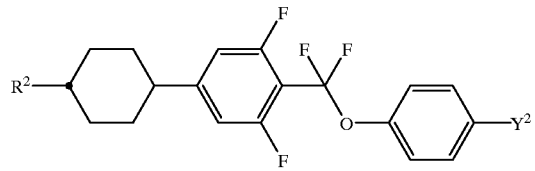
(3-62)
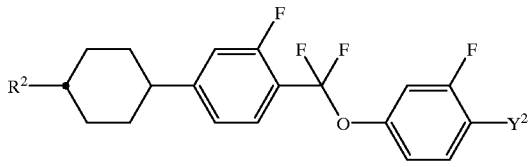
(3-63)
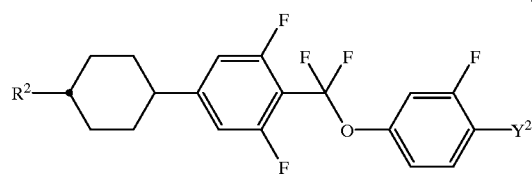
(3-64)
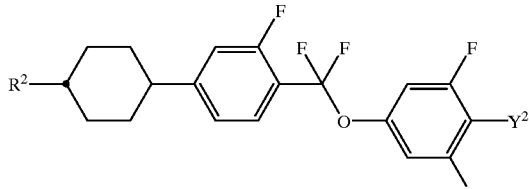
(3-65)
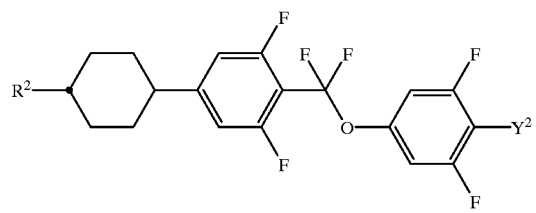
(3-66)
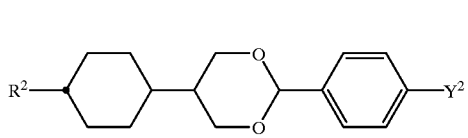
(3-67)
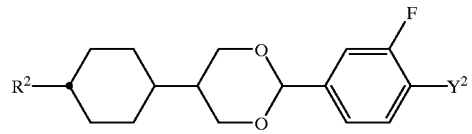
(3-68)
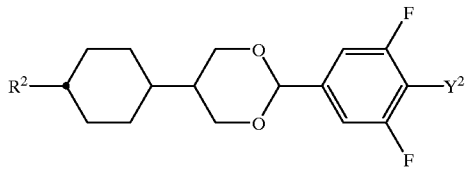
(3-69)
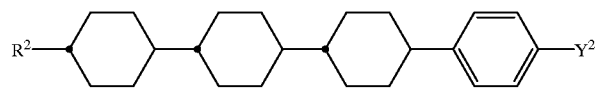
(4-1)
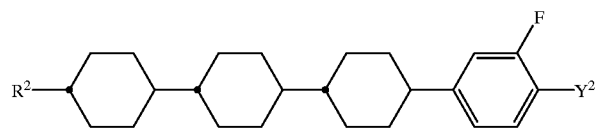
(4-2)
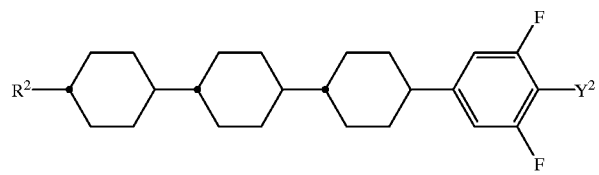
(4-3)
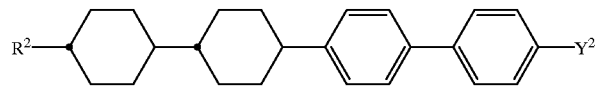
(4-4)

-continued
(4-5)
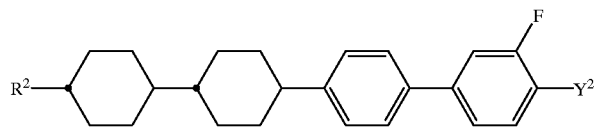
(4-6)
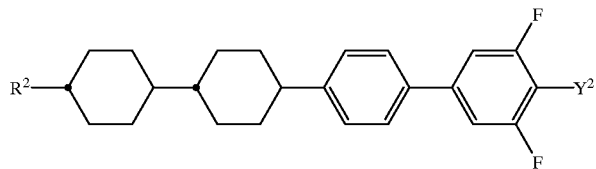
(4-7)
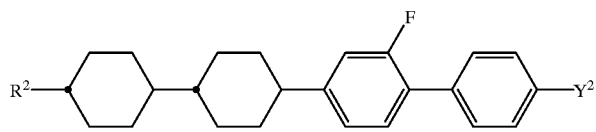
(4-8)
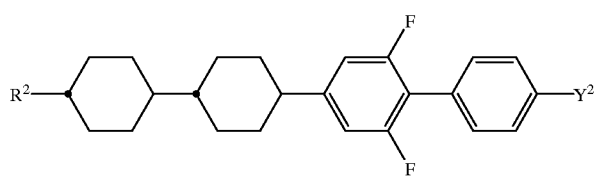
(4-9)
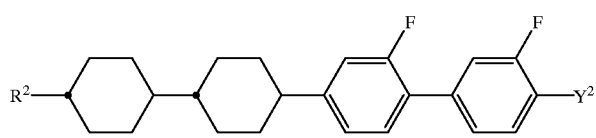
(4-10)
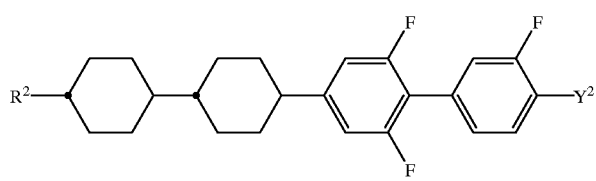
(4-11)
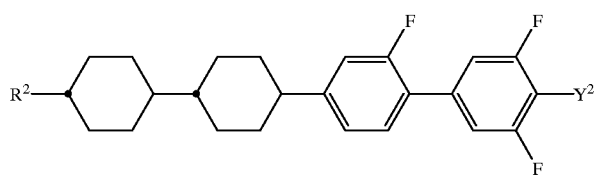
(4-12)
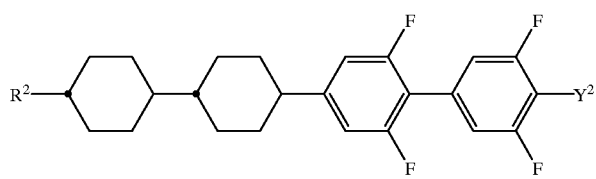
(4-13)
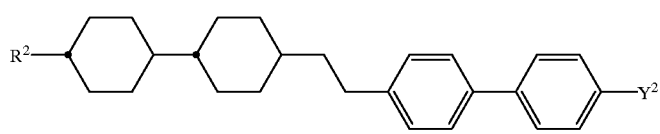

-continued
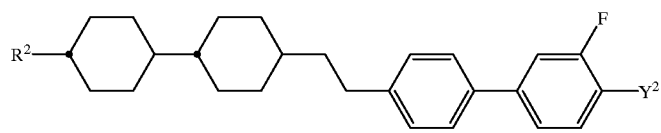
(4-14)
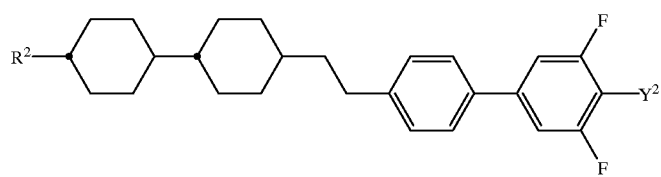
(4-15)
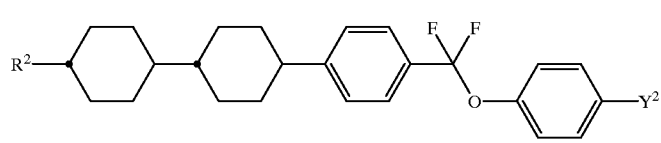
(4-16)
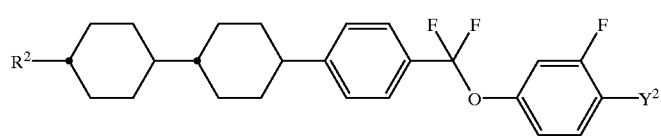
(4-17)
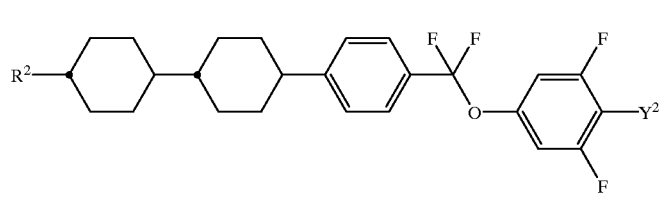
(4-18)
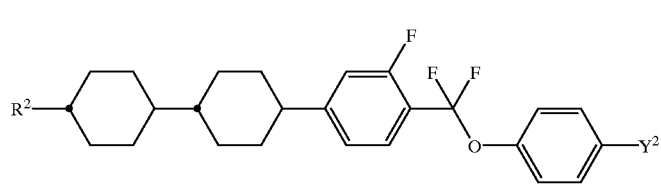
(4-19)
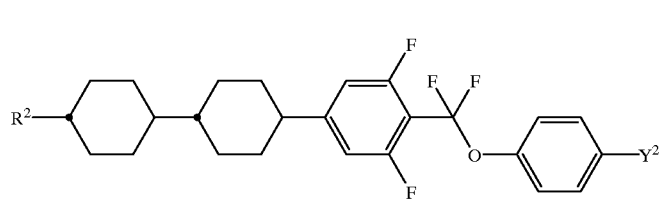
(4-20)
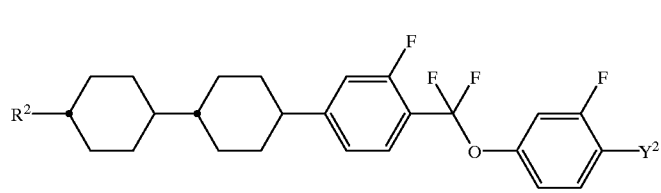
(4-21)
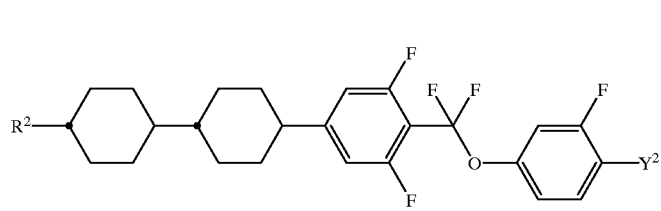
(4-22)

-continued

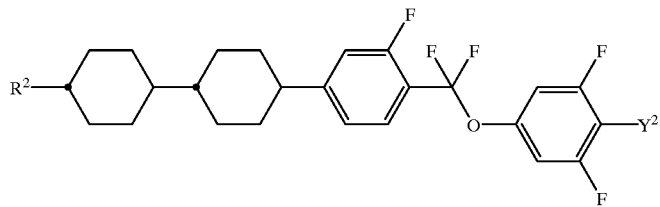
(4-23)

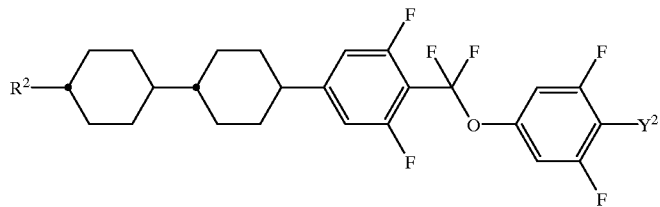
(4-24)

The compounds expressed by the general formulae (2) to (4) are the compounds in which dielectric anisotropic value being positive, and they have very superior thermal and chemical stabilities, so that they are necessary compounds to prepare liquid crystal compositions for TFT display mode in which high reliabilities such as a particularly high voltage holding ratio or a high specific resistant value.

Amounts of the compounds expressed by the general formulae (2) to (4) used may be optionally in a range from 0.1 to 99.9% by weight relative to the total weight of the liquid crystal composition, from 10 to 97% by weight being preferable. More preferably, it is from 40 to 95% by weight. Further, the compounds expressed by the general formulae (7) to (9) may be contained for the purpose of viscosity control In the case of preparing liquid crystal compositions for STN display mode or TN display mode, compounds expressed by the general formulae (2) to (4) can be used. In that case, the said compounds have less effect on decrease in threshold voltage of the liquid crystal compositions than the compounds expressed by the general formulae (5) and (6), so that the amount used is preferably 50% by weight or less.

As compounds expressed by the general formulae (5) and (6) used in the present invention, the following compounds may be preferably mentioned, wherein $R^2$ and $Y^2$ have the same meanings as the above-mentioned ones.

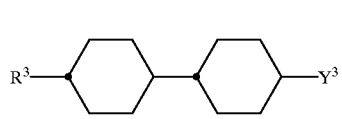
(5-1)

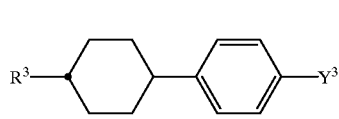
(5-2)

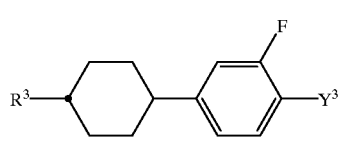
(5-3)

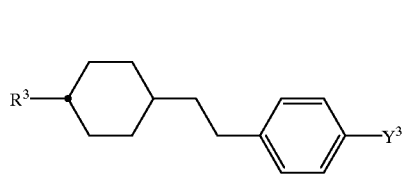
(5-4)

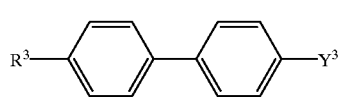
(5-5)

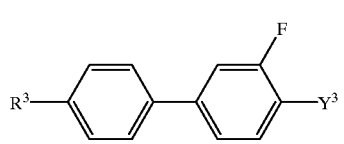
(5-6)

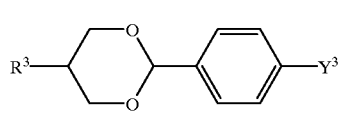
(5-7)

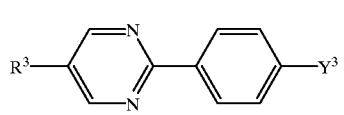
(5-8)

-continued
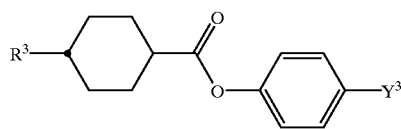
(5-9)
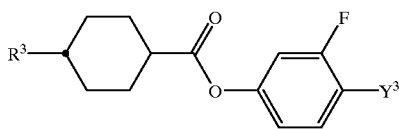
(5-10)
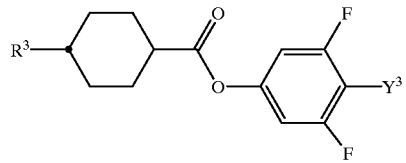
(5-11)
(5-12)
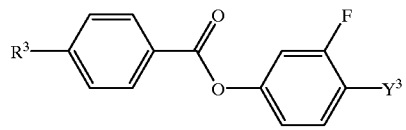
(5-13)
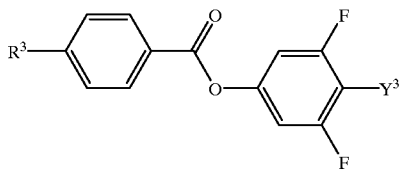
(5-14)
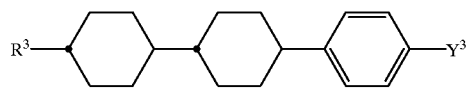
(5-15)
(5-16)
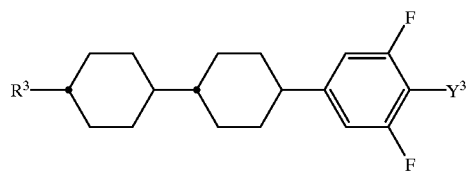
(5-17)
(5-18)
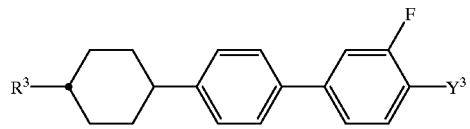
(5-19)
(5-20)
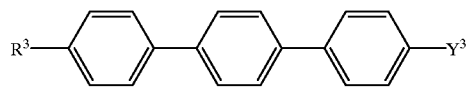
(5-21)
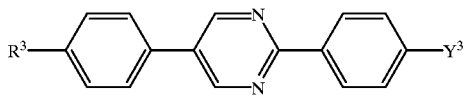
(5-22)
(5-23)
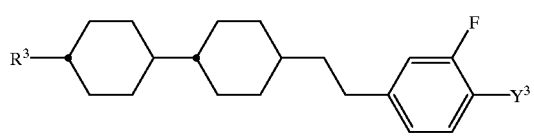
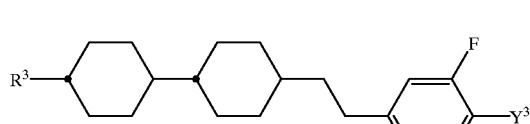
(5-24)
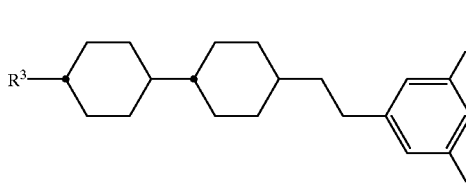
(5-25)

-continued
(5-26)
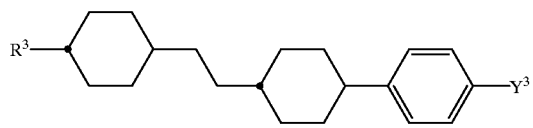
(5-27)
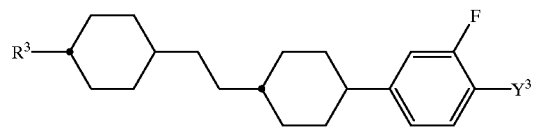
(5-28)
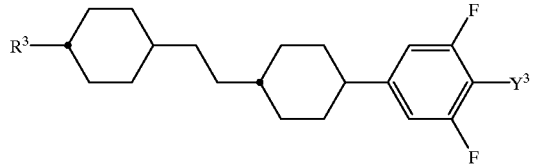
(5-29)
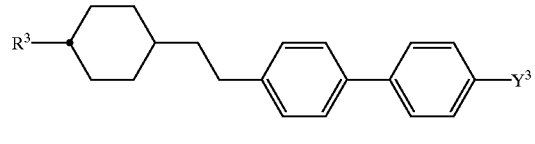
(5-30)
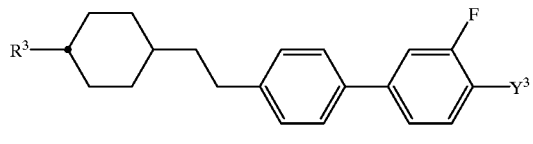
(5-31)
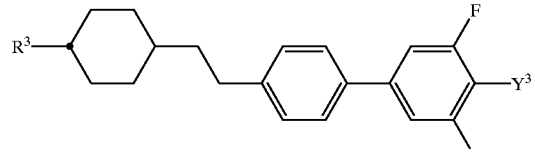
(5-32)
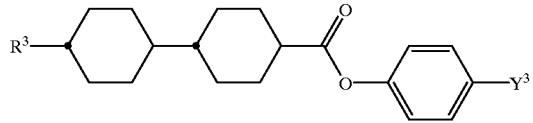
(5-33)
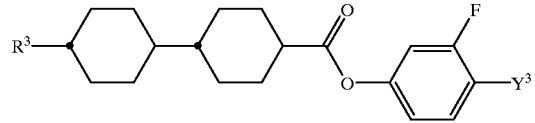
(5-34)
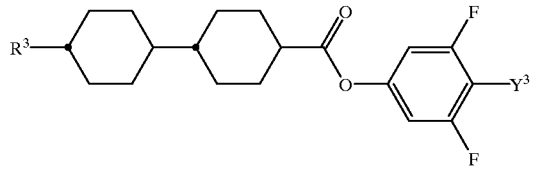
(5-35)
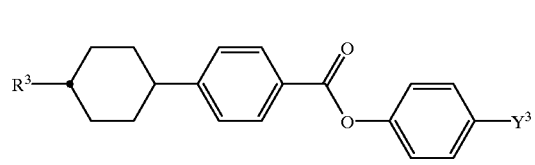
(5-36)
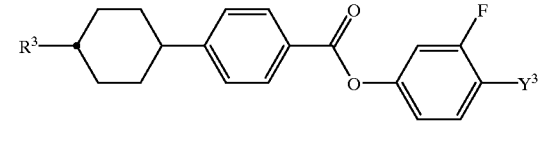
(5-37)
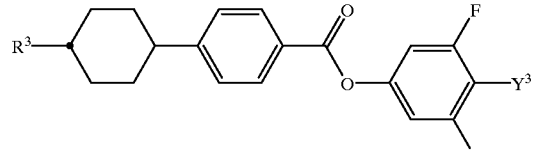
(5-38)
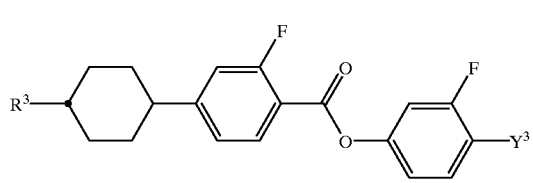
(5-39)
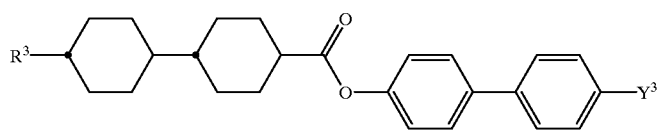
(5-40)
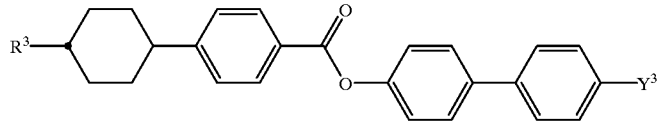

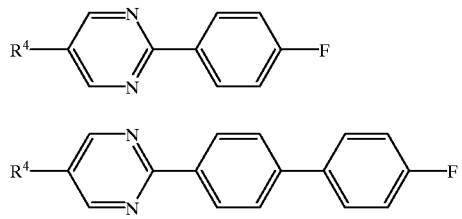

The compounds expressed by the general formulae (5) and (6) have positive and large dielectric anisotropic value, and thus they are used particularly for the purpose to lower threshold voltage of liquid crystal compositions. Further, they are used for the purpose to enlarge a nematic range, such as increase in clear point of liquid crystal compositions and control refractive anisotropic value. Further, they are used for the purposes to improve sharpness of the liquid crystal compositions for STN display mode or TN display mode. The compounds expressed by the general formulae (5) and (6) are indispensable components to prepare the liquid crystal compositions for STN display mode or TN display mode.

If the amount of the compounds expressed by the general formulae (5) and (6) used being increased, threshold voltage of the liquid crystal compositions becomes low and viscosity increases. Therefore, if viscosity of the liquid crystal compositions satisfies the required conditions as to characteristics, it is advantageous to use much amount because of drivability at a low voltage. The amount of the compounds expressed by the general formulae (5) and (6) used may be optionally within a range from 0.1 to 99.9% by weight in the case of preparing the liquid crystal compositions for STN display mode or TN display mode, from 10 to 97% by weight being preferable and from 40 to 95% by weight being more preferable.

As the compounds expressed by the general formulae (7) to (9) used in the present invention, the following compounds may be mentioned, wherein $R^5$ and $R^6$ have the same meanings as the above-mentioned ones.

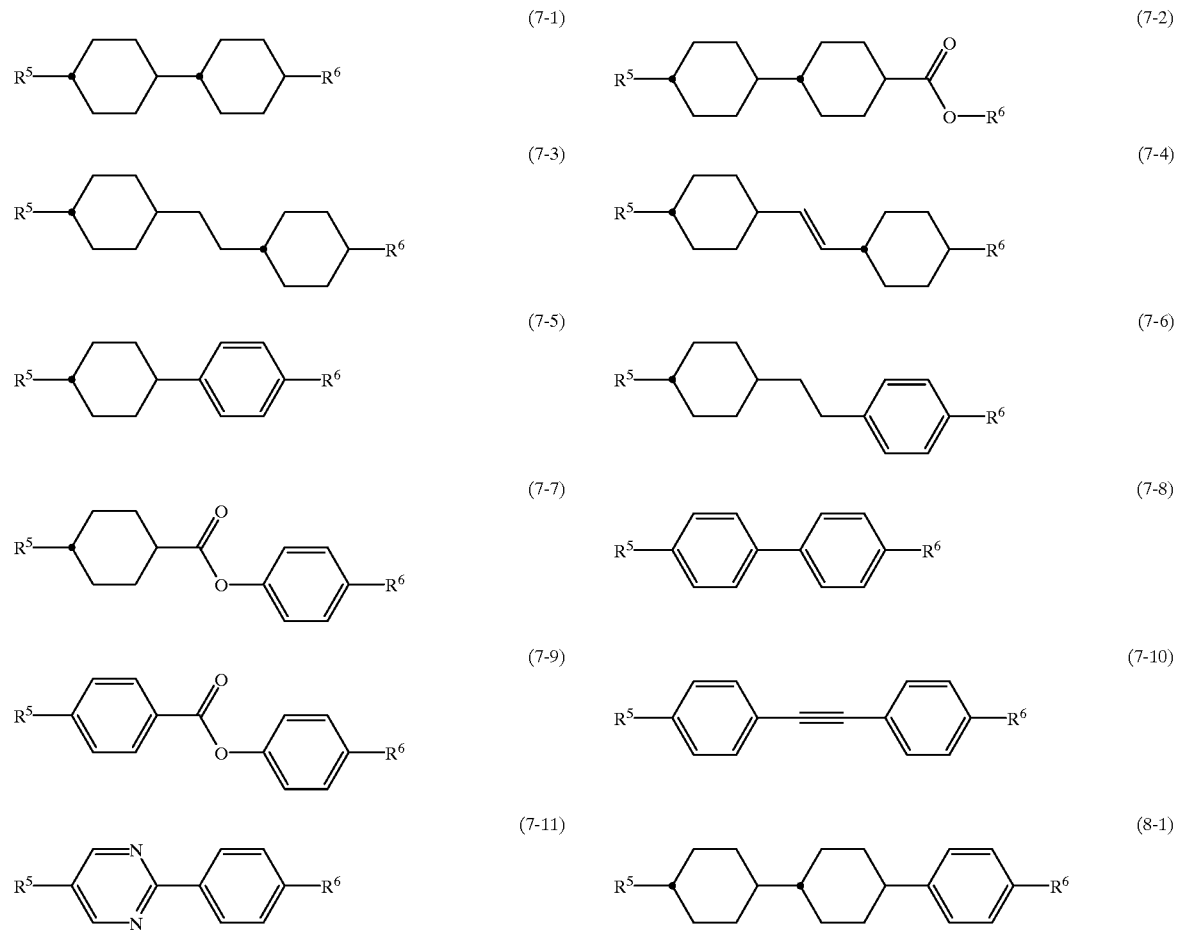

-continued
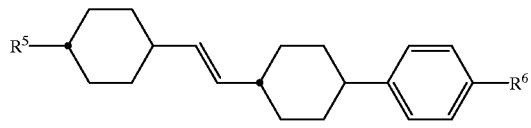
(8-2)
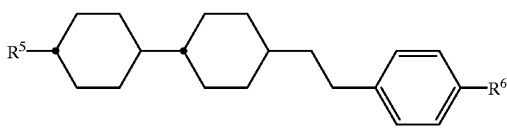
(8-3)
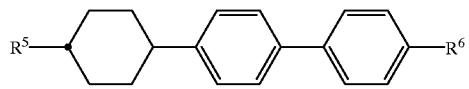
(8-4)
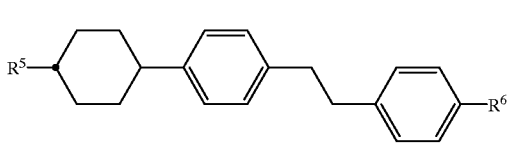
(8-5)
(8-6)
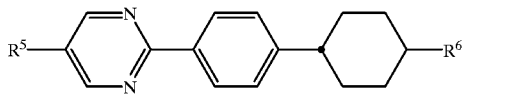
(8-7)
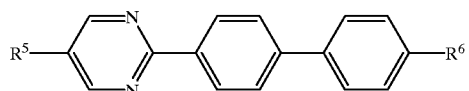
(8-8)
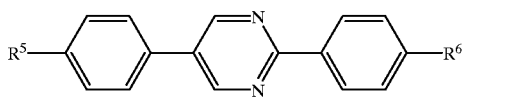
(8-9)
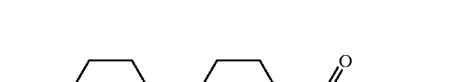
(8-10)
(8-11)
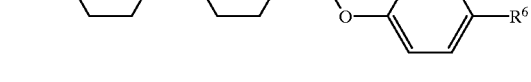
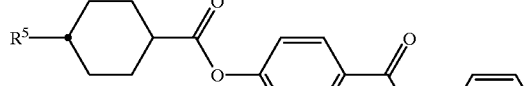
(8-12)
(8-13)
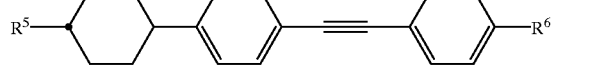
(8-14)
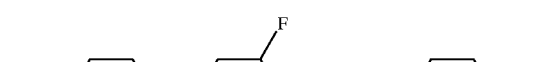
(8-15)
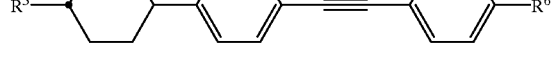
(8-16)
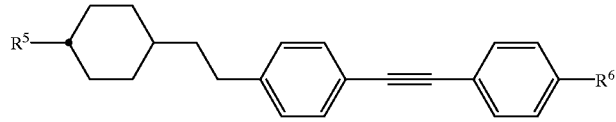
(8-17)
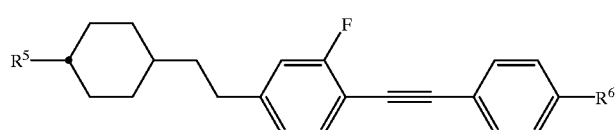

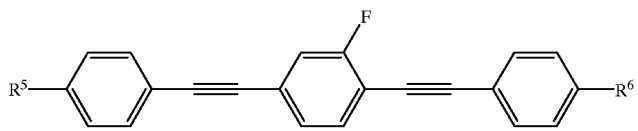

(8-18)

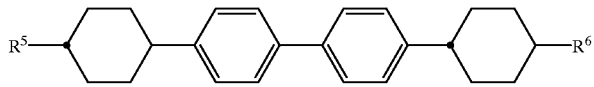

(9-1)

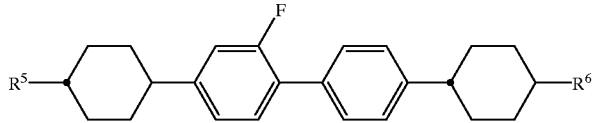

(9-2)

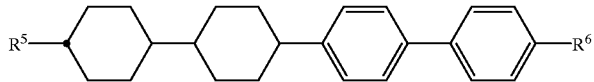

(9-3)

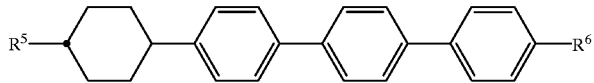

(9-4)

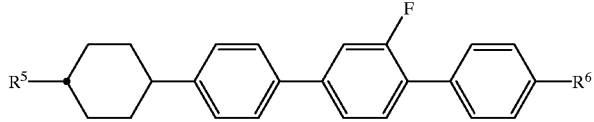

(9-5)

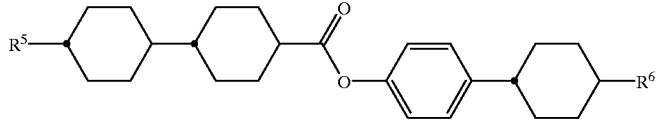

(9-6)

The compounds expressed by the general formulae (7) to (9) have low absolute values of dielectric anisotropy, about neutral one. The compounds expressed by the general formula (7) are used mainly for the purposes to control viscosity of the liquid crystal compositions and to control refractive anisotropy. Further, the compounds expressed by the general formulae (8) and (9) are used for the purpose to enlarge a nematic range, such as increase in clear point of liquid crystal compositions and control refractive anisotropic value.

If the amount of the compounds expressed by the general formulae (7) to (9) used being increased, threshold voltage of the liquid crystal compositions becomes low and viscosity increases. Therefore, if viscosity of the liquid crystal compositions satisfies the required conditions as to characteristics, it is advantageous to use much amount because of drivability at a low voltage. The amount of the compounds expressed by the general formulae (7) to (9) used may optionally be 40% by weight or less, more preferably 35% by weight or less in the case of preparing the liquid crystal compositions for TFT display mode. Further, in the case of preparing the liquid crystal compositions for STN display mode or TN display mode, from 70% by weight or less is preferable and 60% by weight or less is more preferable.

Further, according to the invention, (an) optically active compound(s) is (are) generally added for the purpose of inducing helical structure of the liquid crystal compositions and controlling a twist angle to prevent reverse twist, with the exception if the special cases such as liquid crystal compositions for OCB (Optically Compensated Birefringence) mode. Although any of the known optically active compounds may be used as optically active compounds according to the invention if they are used for the said objects, the following optically active compounds may be preferably mentioned.

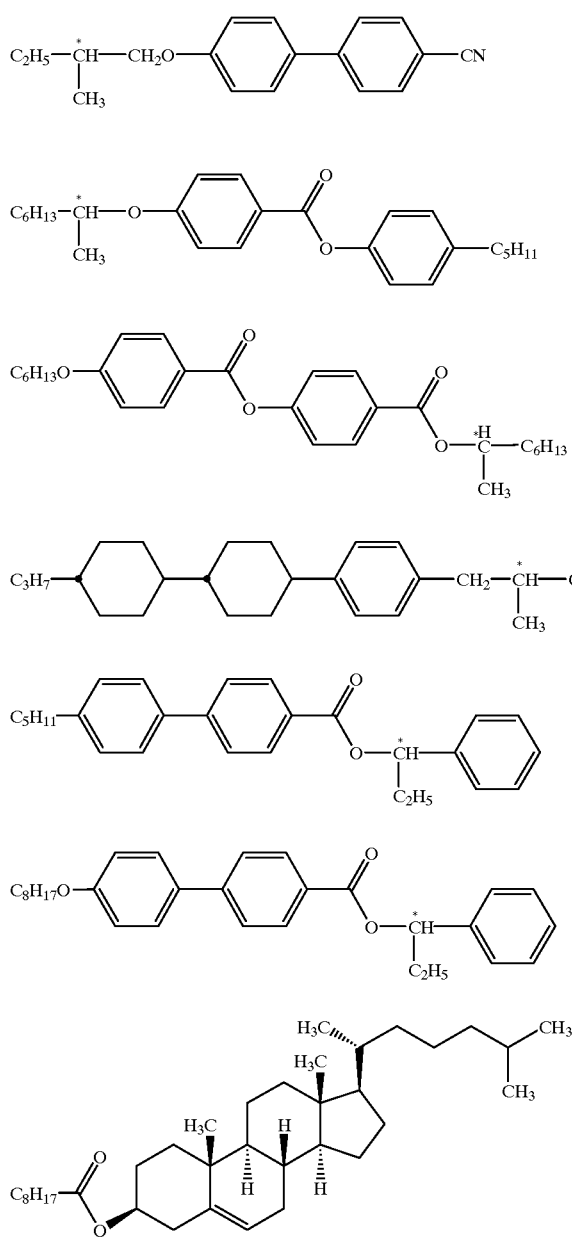

(C15)

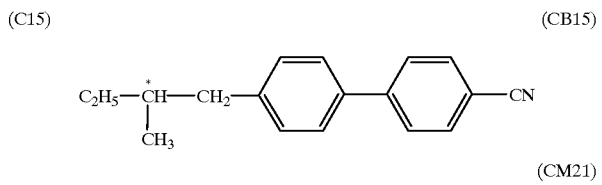

(CB15)

(CM21)

(CM33)

(CM44)

(CM45)

(CM47)

(CN)

In the liquid crystal compositions according to the invention, pitch length of twist may be adjusted generally by adding these organic active compounds. Pitch length is preferably adjusted within a range of 10 to 200 μm. In the case of the liquid crystal composition for STN display mode, it is preferable to adjust within a range of 6 to 20 μm. Further, in the case for Bistable TN mode, it is preferable to adjust within a range of 1.5 to 4 μm. Further, two or more optical active compounds may be added for the purpose of adjusting a temperature-dependency of pitch length.

The liquid crystal compositions used according to the present invention are prepared by the conventional methods known per se. Generally, there is used a method to dissolve various components each other at a high temperature.

The liquid crystal compositions used according to the present invention can be used as liquid crystal compositions for guest host (GH) mode by adding bichromatic dyes such as merocyanine type, styryl type, azo type, azomethine type, azoxy type, quinophthalone type, anthraquinone type and tetrazine type etc. Or, they are used as liquid crystal compositions for polymer dispersion type liquid crystal display element (PDLCD), such as, those obtained by microcapsulating nematic liquid crystals (NCAP), and polymer network liquid crystal display elements (PNLCD). Further, they may be used as liquid crystal compositions for effective control birefringence (ECB) mode or dynamic scattering (DS) mode.

As nematic liquid crytal compositions containing the liquid crystalline compounds according to the invention thus prepared, the following composition examples may be mentioned. However, the compounds in the compositions are denoted by abbreviations according to definitions shown in Table 1. Further, in the case that hydrogen atoms of trans-1,4-cyclohexylene being substituted by deuterium atoms at the positions of $Q^1$, $Q^2$ and $Q^3$ in the following partial structural formulae, positions of deuterium are shown by become symbol H [1D, 2D, 3D], and in the case that hydrogen atoms being substituted by deuterium atoms at the positions of $Q^5$, $Q^6$ and $Q^7$, they are shown by symbol H [5D, 6D, 7D], wherein the positions of deuteriums substitutions are shown by numbers in parentheses.

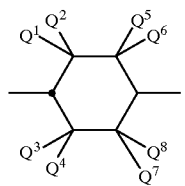

TABLE 1

Manner for describing compounds with codes
R—(A₁)-Z₁— - - Zₙ—(Aₙ)—X

| 1) Left end group R— | Code | 3) Bond group —$Z_1$—, —$Z_n$— | Code |
|---|---|---|---|
| $C_nH_{2n+1}$— | n— | —$C_2H_4$— | 2 |
| $C_nH_{2n+1}O$— | nO— | —$C_4H_8$— | 4 |
| $C_nH_{2n+1}OC_mH_{2m}$— | nOmO— | —COO— | E |
| $CH_2$=CH— | V— | —C≡C— | T |
| $CH_2$=$CHC_nH_{2n}$— | Vn— | —CH=CH— | V |
| $C_nH_{2n+1}CH$=$CHC_mH_{2m}$— | nVm— | —$CF_2O$— | CF2O |
| $C_nH_{2n+1}CH$=$CHC_mH_{2m}CH$=$CHC_kH_{2k}$— | nVmVk— | —$OCF_2$— | OCF2 |

| 2) Cyclic structure —(A₁)—, —(Aₙ)— | Code | 4) Right end group —X | Code |
|---|---|---|---|
| 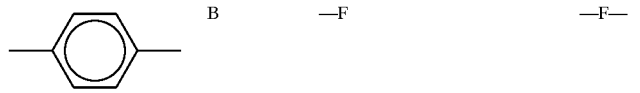 | B | —F | —F— |
|  | B(F) | —Cl | —CL |
| 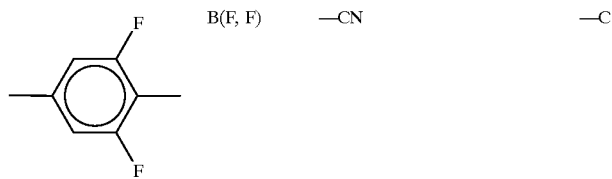 | B(F, F) | —CN | —C |
| 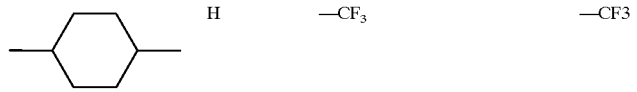 | H | —$CF_3$ | —CF3 |
| 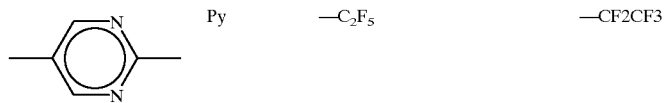 | Py | —$C_2F_5$ | —CF2CF3 |
| 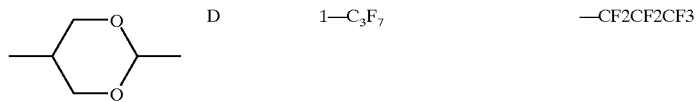 | D | 1—$C_3F_7$ | —CF2CF2CF3 |

TABLE 1-continued

Manner for describing compounds with codes
R—(A₁)–Z₁— - - Zₙ—(Aₙ)—X

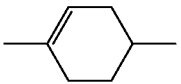

| | | |
|---|---|---|
| Ch | —OCF₃ | —OCF3 |
| | —OCF₂H | —OCF2H |
| | —OCF₂CF₂H | —OCF2CF2H |
| | —OCF₂CFHCF₃ | —OCF2CFHCF3 |
| | —OCH₂CF₂H | —OCH2CF2H |
| | —OCFHCF₃ | —OCFHCF3 |
| | —CₙH₂ₙ₊₁ | —n |
| | —OCₙH₂ₙ₊₁ | —On |
| | —COOCH₃ | —EMe |
| | —CₙH₂ₙCH=CH₂ | —nV— |
| | —CₘH₂ₘCH=CHCₙH₂ₙ₊₁ | —MvN |
| | —CₘH₂ₘCH=CHCₙH₂ₙF | —mVnF |
| | —CH=CF₂ | —CFF |
| | —OCH=CF₂ | —OVFF |

5) Description examples 3

Examlel 3-H2B(F, F)B(F)—F

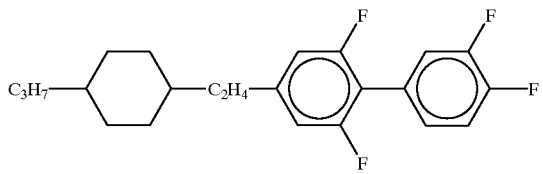

Example2 3-HB(F)TB-2

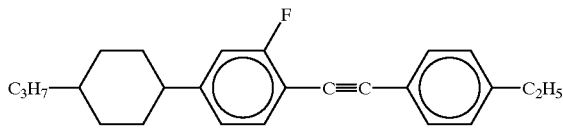

Example3 1V2-BEB(F, F)—C

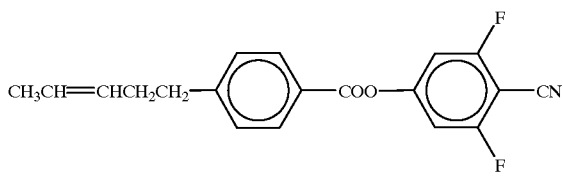

Composition Example 1

| | |
|---|---|
| 3-HBEB(F)-OCF2CF2H | 5.0% |
| 1V2-BEB(F,F)-C | 5.0% |
| 3-HB-C | 25.0% |
| 1-BTB-3 | 5.0% |
| 2-BTB-1 | 10.0% |
| 3-HH-4 | 11.0% |
| 3-HHB-1 | 11.0% |
| 3-HHB-3 | 4.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0,% |
| CM33 | 0.8 parts |

Composition Example 2

| | |
|---|---|
| 5-HB(F,F)EB(F)-OCF2CF2H | 5.0% |
| V2-HB-C | 12.0% |
| 1V2-HB-C | 12.0% |
| 3-HB-C | 15.0% |
| 3-HB[1D,2D,3D]-C | 9.0% |
| 3-HB(F)-C | 5.0% |
| 2-BTB-1 | 2.0% |
| 3-HH-4 | 8.0% |
| 3-HH-VFF | 6.0% |
| 2-H[1D,2D,3D]HB-C | 3.0% |
| 3-HHB-C | 6.0% |
| 3-HB(F)TB-2 | 8.0% |
| 3-H2BTB-3 | 5.0% |
| 3-H2BTB-4 | 4.0% |

Composition Example 3

| | |
|---|---|
| 3-HBCF2OB(F)-OCF2CF2H | 5.0% |
| 201-BEB(F)-C | 5.0% |
| 301-BEB(F)-C | 15.0% |
| 401-BEB(F)-C | 13.0% |
| 501-BEB(F)-C | 13.0% |
| 2-HHB(F)-C | 15.0% |
| 3-HHB(F)-C | 15.0% |
| 3-HB(F)TB-2 | 4.0% |
| 3-HB(F)TB-3 | 4.0% |
| 3-HB(F)TB-4 | 4.0% |
| 3-HHB-1 | 3.0% |
| 3-HHB-O1 | 4.0% |

Composition Example 4

| | |
|---|---|
| 3-HBEB(F)-OCF2CF2H | 4.0% |
| 5-HB(F,F)EB(F)-OCF2CF2H | 3.0% |
| 3-HBCF2OB(F)-OCF2CF2H | 3.0% |
| 5-PyB-F | 4.0% |
| 3-PyB(F)-F | 4.0% |
| 2-BB-C | 5.0% |
| 4-BB-C | 4.0% |
| 5-BB-C | 5.0% |
| 2-PyB-2 | 2.0% |
| 3-PyB-2 | 2.0% |
| 4-PyB-2 | 2.0% |
| 6-PyB-O5 | 3.0% |
| 6-PyB-O6 | 3.0% |
| 6-PyB-O7 | 3.0% |
| 6-PyB-O8 | 3.0% |
| 3-PyBB-F | 6.0% |
| 4-PyBB-F | 6.0% |
| 5-PyBB-F | 6.0% |
| 3-HHB-1 | 6.0% |
| 3-HHB-3 | 8.0% |
| 2-H2BTB-2 | 4.0% |
| 2-H2BTB-3 | 4.0% |
| 3-H2BTB-2 | 5.0% |
| 3-H2BTB-3 | 5.0% |

Composition Example 5

| | |
|---|---|
| 5-HB(F)CF2OBB(F,F)-OCF2CF3 | 3.0% |
| 3-B(F,F)CF2OBB(F,F)-OCF2CF3 | 3.0% |
| 3-HB(F,F)CF2OB(F,F)-OCFHCF3 | 4.0% |
| 3-DB-C | 10.0% |
| 4-DB-C | 10.0% |
| 2-BEB-C | 12.0% |
| 3-BEB-C | 4.0% |
| 3-PyB(F)-F | 6.0% |
| 3-HEB-O4 | 8.0% |
| 4-HEB-O2 | 6.0% |
| 5-HEB-O1 | 6.0% |
| 5-HEB-O2 | 4.0% |
| 5-HEB-5 | 5.0% |
| 4-HEB-5 | 5.0% |
| 10-BEB-2 | 4.0% |
| 3-HHB-1 | 3.0% |
| 3-HHEBB-C | 3.0% |
| 3-HBEBB-C | 2.0% |
| 5-HBEBB-C | 2.0% |

Composition Example 6

| | |
|---|---|
| 3-HB(F)CF2OB(F,F)-OCF2CF2H | 3.0% |
| 3-B(F)CF2OBB(F,F)-OCH2CF2H | 4.0% |
| 5-HB(F)CF2OB(F,F)-OVFF | 3.0% |
| 3-HB-C | 18.0% |
| 7-HB-C | 3.0% |
| 101-HB-C | 10.0% |
| 3-HB(F)-C | 10.0% |
| 2-PyB-2 | 2.0% |
| 3-PyB-2 | 2.0% |
| 4-PyB-2 | 2.0% |
| 101-HH-3 | 7.0% |
| 2-BTB-O1 | 7.0% |
| 3-HHB-1 | 5.0% |
| 3-HHB-F | 4.0% |
| 3-HHB-O1 | 4.0% |
| 3-HHB-3 | 3.0% |
| 3-H2BTB-2 | 3.0% |
| 3-H2BTB-3 | 3.0% |
| 2-PyBH-3 | 4.0% |
| 3-PyBB-2 | 3.0% |

Composition Example 7

| | |
|---|---|
| 3-HBEB(F,F)-OCF2CF2H | 2.0% |
| 5-HB(F,F)EB(F,F)-OCF2CF2H | 2.0% |
| 3-BEBB(F)-OCF2CF2H | 2.0% |
| 201-BEB(F)-C | 5.0% |
| 301-BEB(F)-C | 12.0% |
| 501-BEB(F)-C | 4.0% |
| 1V2-BEB(F,F)-C | 10.0% |
| 3-HH-EMe | 10.0% |
| 3-HB-O2 | 18.0% |
| 7-HEB-F | 2.0% |
| 3-HHEB-F | 2.0% |
| 5-HHEB-F | 2.0% |
| 3-HBEB-F | 4.0% |
| 201-HBEB(F)-C | 2.0% |
| 3-HB(F)EB(F)-C | 2.0% |
| 3-HBEB(F,F)-C | 2.0% |
| 3-HHB-F | 4.0% |
| 3-HHB-O1 | 4.0% |
| 3-HHB-3 | 7.0% |
| 3-HEBEB-F | 2.0% |
| 3-HEBEB-1 | 2.0% |

Composition Example 8

| | |
|---|---|
| 3-HBEB(F)-OCF2CFHCF3 | 5.0% |
| 5-HBCF2OB(F)-OCF2CFHCF3 | 5.0% |
| 5-BEB(F)-C | 5.0% |
| V-HB-C | 11.0% |
| 5-PyB-C | 6.0% |
| 4-BB-3 | 11.0% |
| 3-HH-2V | 10.0% |
| 5-HH-V | 11.0% |
| V-HHB-1 | 7.0% |
| V2-HHB-1 | 10.0% |
| 3-HHB-1 | 4.0% |
| 1V2-HBB-2 | 10.0% |
| 3-HHEBH-2 | 5.0% |

Composition Example 9

| | |
|---|---|
| 5-HB(F,F)EB(F)-OCF2CF2H | 4.0% |
| 5-HB(F,F)EB(F,F)-OCF2CF2H | 4.0% |
| 3-HB(F)CF2OB(F,F)-OCF2CF2H | 4.0% |
| 3-B(F,F)CF2OBB(F,F)-OCF2CF2CF3 | 4.0% |
| 2O1-BEB(F)-C | 5.0% |
| 3O1-BEB(F)-C | 12.0% |
| 1V2-BEB(F,F)-C | 16.0% |
| 3-HB-O2 | 10.0% |
| 3-HH-4 | 3.0% |
| 3-HHB-F | 3.0% |
| 3-HHB-1 | 3.0% |
| 3-HHB-O1 | 4.0% |
| 3-HBEB-F | 4.0% |
| 5-HHEB-F | 7.0% |
| 3-H2BTB-2 | 4.0% |
| 3-H2BTB-3 | 4.0% |
| 3-H2BTB-4 | 4.0% |
| 3-HB(F)TB-2 | 5.0% |

Composition Example 10

| | |
|---|---|
| 3-HBEB(F)-OCF2CF2H | 4.0% |
| 3-BEBB(F)-OCF2CF2H | 4.0% |
| 2-BEB-C | 12.0% |
| 3-BEB-C | 4.0% |
| 4-BEB-C | 6.0% |
| 3-HB-C | 28.0% |
| 3-HEB-O4 | 12.0% |
| 4-HEB-O2 | 8.0% |
| 5-HEB-O1 | 4.0% |
| 3-HEB-O2 | 6.0% |
| 5-HEB-O2 | 5.0% |
| 3-HHB-1 | 3.0% |
| 3-HHB-O1 | 4.0 |

Composition Example 11

| | |
|---|---|
| 5-HB(F,F)EB(F)-OCF2CF2H | 4.0% |
| 3-B(F)CF2OBB(F,F)-OCH2CF2H | 4.0% |
| 2-BEB-C | 10.0% |
| 5-BB-C | 12.0% |
| 7-BB-C | 7.0% |
| 1-BTB-3 | 7.0% |
| 2-BTB-1 | 10.0% |
| 10-BEB-2 | 10.0% |
| 10-BEB-5 | 12.0% |
| 2-HHB-1 | 4.0% |
| 3-HHB-F | 4.0% |
| 3-HHB-1 | 7.0% |
| 3-HHB-O1 | 4.0% |
| 3-HHB-3 | 5.0% |

Composition Example 12

| | |
|---|---|
| 3-HBCF2OB(F)-OCF2CF2H | 4.0% |
| 3-HBEB(F,F)-OCF2CF2H | 4.0% |
| 5-HB(F)CF2OB(F,F)-OVFF | 4.0% |
| 1V2-BEB(F,F)-C | 8.0% |
| 3-HB-C | 10.0% |
| V2V-HB-C | 14.0% |
| V2V-HH-3 | 19.0% |
| 3-HB-O2 | 4.0% |
| 3-HHB-1 | 10.0% |
| 3-HHB-3 | 3.0% |
| 3-HB(F)TB-2 | 4.0% |
| 3-HB(F)TB-3 | 4.0% |
| 3-H2BTB-2 | 4.0% |
| 3-H2BTB-3 | 4.0% |
| 3-H2BTB-4 | 4.0% |

Composition Example 13

| | |
|---|---|
| 3-HBEB(F)-OCF2CF2H | 4.0% |
| 5-HB(F)CF2OBB(F,F)-OCF2CF3 | 4.0% |
| 5-HB(F,F)CF2OB(F,F)-OCFHCF3 | 4.0% |
| 5-BTB(F)TB-3 | 10.0% |
| V2-HB-TC | 10.0% |
| 3-HB-TC | 10.0% |
| 3-HB-C | 10.0% |
| 5-HB-C | 7.0% |
| 5-BB-C | 3.0% |
| 2-BTB-1 | 10.0% |
| 2-BTB-O1 | 5.0% |
| 3-HH-4 | 5.0% |
| 3-HHB-1 | 4.0% |
| 3-HHB-3 | 5.0% |
| 3-H2BTB-2 | 3.0% |
| 3-H2BTB-3 | 3.0% |
| 3-HB(F)TB-2 | 3.0% |

Composition Example 14

| | |
|---|---|
| 3-HBEB(F)-OCF2CFHCF3 | 5.0% |
| IV2-BEB(F,F)-C | 6.0% |
| 3-HB-C | 18.0% |
| 2-BTB-1 | 10.0% |
| 5-HH-VFF | 30.0% |
| 1-BHH-VFF | 8.0% |
| 1-BHH-2VFF | 11.0% |
| 3-H2BTB-3 | 4.0% |
| 3-H2BTB-4 | 4.0% |
| 3-HHB-1 | 4.0% |

Composition Example 15

| | |
|---|---|
| 5-HBCF2OB(F)-OCF2CFHCF3 | 5.0% |
| 3-B(F)CF2OBB(F,F)-OCH2CF2H | 5.0% |
| 3-B(F,F)CF2OBB(F,F)-OCF2CF2CF3 | 5.0% |
| 2-HB-C | 5.0% |
| 3-HB-C | 12.0% |
| 3-HB-O2 | 15.0% |
| 2-BTB-1 | 3.0% |
| 3-HHB-1 | 8.0% |
| 3-HHB-F | 4.0% |
| 3-HHB-O1 | 5.0% |
| 3-HHB-3 | 4.0% |
| 3-HHEB-F | 4.0% |
| 5-HHEB-F | 4.0% |
| 2-HHB(F)-F | 2.0% |
| 3-HHB(F)-F | 7.0% |
| 5-HHB(F)-F | 7.0% |
| 3-HHB(F,F)-F | 5.0% |

Composition Example 16

| | |
|---|---|
| 3-HBEB(F)-0CF2CF2H | 5.0% |
| 5-HB(F,F)EB(F)-0CF2CF2H | 5.0% |
| 2-HHB(F)-F | 17.0% |
| 3-HHB(F)-F | 17.0% |
| 5-HHB(F)-F | 6.0% |
| 2-H2HB(F)-F | 10.0% |
| 3-H2HB(F)-F | 5.0% |
| 5-H2HB(F)-F | 10.0% |
| 2-HBB(F)-F | 6.0% |
| 3-HBB(F)-F | 6.0% |
| 5-HBB(F)-F | 13.0% |
| CN | 0.3 parts |

Composition Example 17

| | |
|---|---|
| 3-HBCF20B(F)-0CF2CF2H | 5.0% |
| 3-HBEB(F,F)-0CF2CF2H | 5.0% |
| 5-HBCF20B(F)-0CF2CFHCF3 | 5.0% |
| 7-HB(F)-F | 5.0% |
| 5-H2B(F)-F | 5.0% |
| 3-HB-02 | 10.0% |
| 3-HH-4 | 2.0% |
| 3-HH[5D,6D,7D]-4 | 3.0% |
| 2-HHB(F)-F | 10.0% |
| 3-HHB(F)-F | 10.0% |
| 5-HH[5D,6D,7D]B(F)-F | 10.0% |
| 3-H2HB(F)-F | 5.0% |
| 2-HBB(F)-F | 3.0% |
| 3-HBB(F)-F | 3.0% |
| 2-H2BB(F)-F | 5.0% |
| 3-HHB-1 | 5.0% |
| 3-HHB-01 | 5.0% |
| 3-HHB-3 | 4.0% |

Composition Example 18

| | |
|---|---|
| 5-HB(F,F)EB(F,F)-0CF2CF2H | 5.0% |
| 3-HB(F)CF20B(F,F)-0CF2CF2H | 5.0% |
| 3-B(F)CF20BB(F,F)-0CH2CF2H | 5.0% |
| 7-HB(F,F)-F | 3.0% |
| 3-HB-02 | 7.0% |
| 2-HHB(F)-F | 10.0% |
| 3-HHB(F)-F | 10.0% |
| 5-HHB(F)-F | 5.0% |
| 2-HBB(F)-F | 9.0% |
| 3-HBB(F)-F | 9.0% |
| 5-HBB(F)-F | 6.0% |
| 2-HBB-F | 4.0% |
| 3-HBB-F | 4.0% |
| 5-HBB-F | 3.0% |
| 3-HBB(F,F)-F | 5.0% |
| 5-HBB(F,F)-F | 10.0% |

Composition Example 19

| | |
|---|---|
| 3-BEBB(F)-0CF2CF2H | 5.0% |
| 5-HB(F)CF20B(F,F)-0VFF | 5.0% |
| 3-B(F,F)CF20BB(F,F)-0CF2CF2CF3 | 5.0% |
| 7-HB(F,F)-F | 3.0% |
| 3-H2HB(F,F)-F | 12.0% |
| 4-H2HB(F,F)-F | 10.0% |
| 3-HHB(F,F)-F | 5.0% |
| 4-HHB(F,F)-F | 5.0% |
| 3-HH2B(F,F)-F | 10.0% |
| 5-HH2B(F,F)-F | 10.0% |
| 3-HBB(F,F)-F | 12.0% |
| 5-HBB(F,F)-F | 12.0% |
| 3-HBCF20B(F,F)-F | 6.0% |

Composition Example 20

| | |
|---|---|
| 3-HBEB(F)-0CF2CFHCF3 | 5.0% |
| 5-HB(F)CF20BB(F,F)-0CF2CF3 | 5.0% |
| 5-HB(F,F)CF20B(F,F)-0CFHCF3 | 5.0% |
| 7-HB(F,F)-F | 5.0% |
| 3-H2HB(F,F)-F | 12.0% |
| 4-H2HB(F,F)-F | 10.0% |
| 3-HHB(F,F)-F | 10.0% |
| 4-HHB(F,F)-F | 5.0% |
| 3-HBB(F,F)-F | 10.0% |
| 3-HHEB(F,F)-F | 10.0% |
| 4-HHEB(F,F)-F | 3.0% |
| 2-HBEB(F,F)-F | 3.0% |
| 3-HBEB(F,F)-F | 5.0% |
| 5-HBEB(F,F)-F | 3.0% |
| 3-HDB(F,F)-F | 6.0% |
| 3-HHBB(F,F)-F | 3.0% |

Composition Example 21

| | |
|---|---|
| 3-HBEB(F)-0CF2CF2H | 4.0% |
| 5-HB(F,F)EB(F)-0CF2CF2H | 4.0% |
| 3-HBCF20B(F)-0CF2CF2H | 4.0% |
| 5-HBCF20B(F)-0CF2CFHCF3 | 4.0% |
| 3-HB-CL | 10.0% |
| 5-HB-CL | 4.0% |
| 7-HB-CL | 4.0% |
| 101-HH-5 | 5.0% |
| 2-HBB(F)-F | 8.0% |
| 3-HBB(F)-F | 8.0% |
| 5-HBB(F)-F | 2.0% |
| 4-HHB-CL | 8.0% |
| 5-HHB-CL | 4.0% |
| 3-H2HB(F)-CL | 4.0% |
| 3-HBB(F,F)-F | 10.0% |
| 5-H2BB(F,F)-F | 9.0% |
| 3-HB(F)VB-2 | 4.0% |
| 3-HB(F)VB-3 | 4.0% |

Composition Example 22

| | |
|---|---|
| 3-HBEB(F,F)-0CF2CF2H | 5.0% |
| 5-HB(F,F)EB(F,F)-0CF2CF2H | 5.0% |
| 3-HB(F)CF20B(F,F)-0CF2CF2H | 5.0% |
| 3-B(F)CF20BB(F,F)-0CH2CF2H | 5.0% |
| 3-HHB(F,F)-F | 9.0% |
| 3-H2HB(F,F)-F | 8.0% |
| 4-H2HB(F,F)-F | 8.0% |
| 3-HBB(F,F)-F | 21.0% |
| 5-HBB(F,F)-F | 8.0% |
| 3-H2BB(F,F)-F | 10.0% |
| 5-HHBB(F,F)-F | 3.0% |
| 5-HHEBB-F | 2.0% |
| 3-HH2BB(F,F)-F | 3.0% |
| 101-HBBH-4 | 4.0% |
| 101-HBBH-5 | 4.0% |

Composition Example 23

| | |
|---|---|
| 3-BEBB(F)-OCF2CF2H | 5.0% |
| 5-HB(F,F)CF2OB(F,F)-OCFHCF3 | 5.0% |
| 5-HB-F | 12.0% |
| 6-HB-F | 9.0% |
| 7-HB-F | 7.0% |
| 3-HHB-OCF3 | 7.0% |
| 4-HHB-OCF3 | 7.0% |
| 5-HHB-OCF3 | 5.0% |
| 3-HH2B-OCF3 | 4.0% |
| 5-HH2B-OCF3 | 4.0% |
| 3-HHB(F,F)-OCF3 | 5.0% |
| 3-HBB(F)-F | 10.0% |
| 5-HBB(F)-F | 7.0% |
| 3-HH2B(F)-F | 3.0% |
| 3-HB(F)BH-3 | 3.0% |
| 5-HBBH-3 | 3.0% |
| 3-HHB(F,F)-OCF2H | 4.0% |

Composition Example 24

| | |
|---|---|
| 5-HB(F)CF2OB(F,F)-OVFF | 5.0% |
| 5-HB(F)CF2OB(F,F)-OCF2CF3 | 5.0% |
| 3-B(F,F)CF2OBB(F,F)-OCF2CF2CF3 | 5.0% |
| 5-H4HB(F,F)-F | 7.0% |
| 5-H4HB-OCF3 | 5.0% |
| 3-H4HB(F,F)-CF3 | 8.0% |
| 5-H4HB(F,F)-CF3 | 5.0% |
| 3-HB-CL | 6.0% |
| 5-HB-CL | 4.0% |
| 2-H2BB(F)-F | 5.0% |
| 3-H2BB(F)-F | 10.0% |
| 5-HVHB(F,F)-F | 5.0% |
| 3-HHB-OCF3 | 5.0% |
| 3-H2HB-OCF3 | 5.0% |
| V-HHB(F)-F | 5.0% |
| 3-HHB(F)-F | 5.0% |
| 5-HHEB-OCF3 | 2.0% |
| 3-HBEB(F,F)-F | 5.0% |
| 5-HH-V2F | 3.0% |

Composition Example 25

| | |
|---|---|
| 5-HB(F)CF2OB(F,F)-OVFF | 2.0% |
| 3-B(F,F)CF2OBB(F,F)-OCF2CF2CF3 | 2.0% |
| 5-HB(F,F)CF2OB(F,F)-OCFHCF3 | 2.0% |
| 2-HHB(F)-F | 2.0% |
| 3-HHB(F)-F | 2.0% |
| 5-HHB(F)-F | 2.0% |
| 2-HBB(F)-F | 6.0% |
| 3-HBB(F)-F | 6.0% |
| 5-HBB(F)-F | 10.0% |
| 2-H2BB(F)-F | 9.0% |
| 3-H2BB(F)-F | 9.0% |
| 3-HBB(F,F)-F | 25.0% |
| 5-HBB(F,F)-F | 13.0% |
| 101-HBBH-4 | 5.0% |
| 101-HBBH-5 | 5.0% |

Composition Example 26

| | |
|---|---|
| 5-HBCF2OB(F)-OCF2CFHCF3 | 3.0% |
| 3-HB(F)CF2OB(F,F)-OCF2CF2H | 3.0% |
| 5-HB(F)CF2OBB(F,F)-OCF2CF3 | 3.0% |

-continued

| | |
|---|---|
| 5-HB-CL | 12.0% |
| 3-HH-4 | 7.0% |
| 3-HB-O2 | 20.0% |
| 3-H2HB(F,F)-F | 4.0% |
| 3-HHB(F,F)-F | 8.0% |
| 3-HBB(F,F)-F | 6.0% |
| 2-HHB(F)-F | 5.0% |
| 3-HHB(F)-F | 5.0% |
| 2-H2HB(F)-F | 2.0% |
| 3-H2HB(F)-F | 1.0% |
| 5-H2HB(F)-F | 2.0% |
| 3-HHHBB(F,F)-F | 4.0% |
| 3-HBCF2OB-OCF3 | 4.0% |
| 5-HBCF2OB(F,F)-CF3 | 4.0% |
| 3-HHB-1 | 3.0% |
| 3-HHB-O1 | 4.0% |

Composition Example 27

| | |
|---|---|
| 5-HB(F,F)EB(F)-OCF2CF2H | 5.0% |
| 3-HBCF2OB(F)-OCF2CF2H | 5.0% |
| 3-HBEB(F,F)-OCF2CF2H | 5.0% |
| 5-HB(F,F)EB(F,F)-OCF2CF2H | 5.0% |
| 3-HBEB(F)-OCF2CFHCF3 | 5.0% |
| 3-HB(F)CF2OB(F,F)-OCF2CF2H | 5.0% |
| 5-HB(F,F)CF2OB(F,F)-OCFHCF3 | 5.0% |
| 2-HHB(F)-F | 17.0% |
| 3-HHB(F)-F | 17.0% |
| 2-H2HB(F)-F | 10.0% |
| 3-H2HB(F)-F | 5.0% |
| 5-H2HB(F)-F | 4.0% |
| 2-HBB(F)-F | 6.0% |
| 3-HBB(F)-F | 6.0% |
| CN | 0.3 parts |

Composition Example 28

| | |
|---|---|
| 3-HBCF2OB(F)-OCF2CF2H | 3.0% |
| 3-BEBB(F)-OCF2CF2H | 3.0% |
| 3-HBEB(F)-OCF2CFHCF3 | 3.0% |
| 3-BEB(F)-C | 8.0% |
| 3-HB-C | 8.0% |
| V-HB-C | 8.0% |
| 1V-HB-C | 8.0% |
| 3-HB-O2 | 3.0% |
| 3-HH-2V | 14.0% |
| 3-HH-2V1 | 7.0% |
| V2-HHB-1 | 10.0% |
| 3-HBB-1 | 5.0% |
| 3-HHEB-F | 7.0% |
| 3-H2BTB-2 | 2.0% |
| 3-H2BTB-3 | 6.0% |
| 3-H2BTB-4 | 5.0% |

Composition Example 29

| | |
|---|---|
| 5-HBCF2OB(F)-OCF2CFHCF3 | 5.0% |
| 3-B(F)CF2OBB(F,F)-OCH2CF2H | 5.0% |
| 5-HB(F)CF2OB(F,F)-OVFF | 5.0% |
| 3-H2HB(F,F)-F | 7.0% |
| 5-H2HB(F,F)-F | 8.0% |
| 3-HHB(F,F)-F | 10.0% |
| 3-HH2B(F,F)-F | 9.0% |
| 5-HH2B(F,F)-F | 4.0% |
| 3-HBB(F,F)-F | 15.0% |

| | |
|---|---|
| -continued | |
| 5-HBB(F,F)-F | 15.0% |
| 3-HBEB(F,F)-F | 2.0% |
| 4-HBEB(F,F)-F | 2.0% |
| 5-HBEB(F,F)-F | 2.0% |
| 3-HHEB(F,F)-F | 5.0% |
| 4-HHEB(F,F)-F | 3.0% |
| 5-HHEB(F,F)-F | 3.0% |

The compounds expressed by the general formula (1) according to the invention can be produced easily by using conventional organic synthetic methods. For example, the said compounds can be synthesized easily by selecting and combining methods described in Organic Synthesis, Organic Reactions and Experimental Chemical Courses etc. In particular, the compounds wherein ring A being silacyclohexane ring can be synthesized according to the method disclosed in Japanese Patent Application Laid-open Hie 7-173176.

For example, the compounds of the general formula (1) wherein m=1, n=0 and $Z^2$ being —COO— can be produced by a method for reacting a phenol derivative with a carboxylic derivative in a solvent such as dichloromethane and chloroform as well as in the presence of a dehydration agent such as dicyclohexylcarbodiimide (DCC) and 4-dimethylaminopyridine (DMAP) (B. Neises et al., Organic Synthesis, 63, 183 (1985)), or a method for reacting a phenol derivative with a carboxylic chloride derivative in a solvent such as dichloromethane and chloroform as well as in the presence of a base such as pyridine, diethylamine and triethylamine (Japanese Patent Application Laid-open Hei 2-233626).

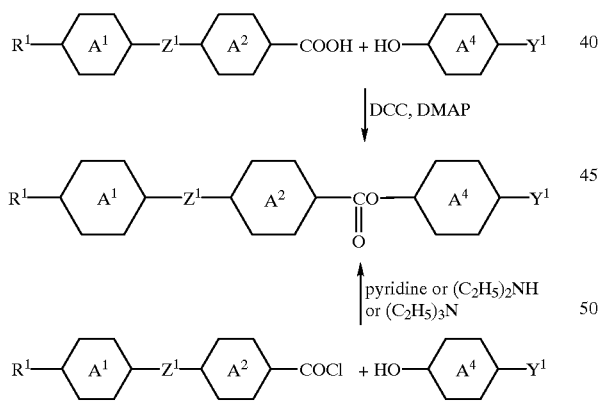

Further, the compounds of the general formula (1) wherein m=1, n=0 and $Z^2$ being —$CF_2O$— can be produced by converting an aromatic halide into a Grignard reagent or a lithiated compound with use of magnesium or metallic lithium and then reacting with carbon disulfide to form dithiocarboxylic acid. The said acid can be reacted with a phenol derivative in the presence of hydride of alkali metal and iodine to form a thioester derivative. Then, by using a fluorinating reagent such as hydrogen fluoride-pyridine and diethylaminosulfate trifluoride (hereinafter referred to DAST), the above-mentioned compounds can be produced.

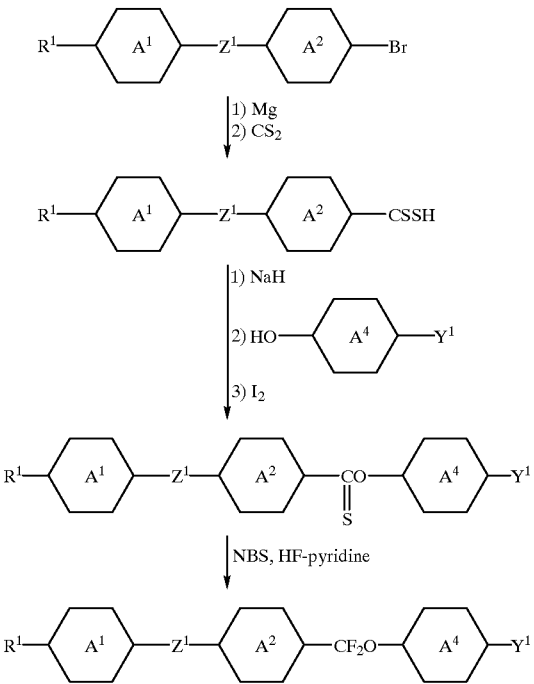

A thioester derivative can be produced also by reacting a lawessen's reagent with the ester derivative synthesized as above. Then, by using a fluorinating reagent such as hydrogen fluoride-pyridine and DAST, the above-mentioned compounds can be produced.

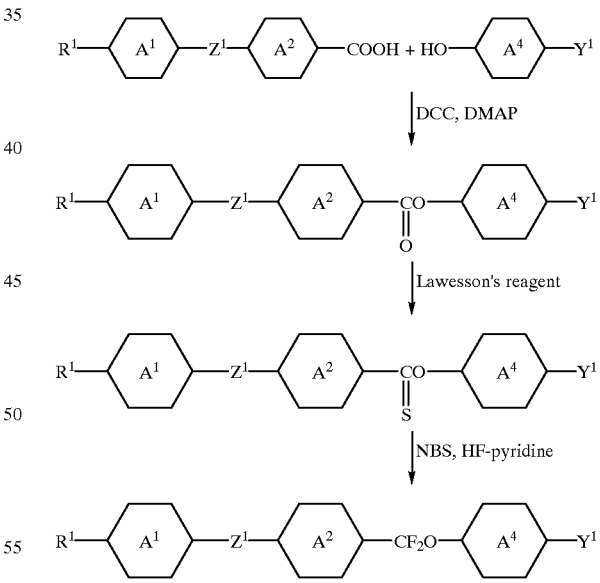

Further, the compounds of the general formula (1) wherein m=1, n=0, $Z^2$ being —$CF_2O$— and ring $A^2$ being 3-cyclohexen-1,4-ylene or 3-fluoro-3-cyclohexen-1,4-ylene can be produced by the following procedures. That is, a cyclohexanone derivative is reacted with hexamethylphosphorus triamide and dibromodifluoromethane to form a difluorohexylidene derivative, which is then subjected to an addition reaction with bromine and reacted with an alcohol derivative in the presence of a polar aprotic slvent such as N,N-dimethylformamide (hereinafter referred to DMF) to carry out dehydrobromination and etherification simultaneously, to prepare a compound wherein ring A² being 3-cyclohexen-1,4-ylene. Further, the compound thus obtained is hydroborated (H. C. Brown, Organic Syntheses via Borane, John Wiley (1975)), then treated with an oxidant such as pyrijinium chlorochromate (hereinafter referred to PCC), to produce a cyclohexanone derivative. It is then fluorinated with DAST and the difuoro compound obtained is treated with a base such as potassium-t-butoxide, to produce a compound wherein A² being 3-fluoro-3-cyclohexen-1,4-ylene.

| No. | R¹ | A¹ | Z¹ | A⁴ | Y¹ |
|---|---|---|---|---|---|
| 1 | CH₃OCH₂ | cyclohexane | COO | phenyl, F | OCF₂CF₂H |
| 2 | cyclobutylmethyl | cyclohexane | COO | phenyl, F | OCF₂CF₂H |
| 3 | C₅H₁₁ | cyclohexane | COO | phenyl, F, F | OCF₂CF₂H |
| 4 | C₅H₁₁ | cyclohexane | COO | phenyl, F | OCF₂CF₂Cl |
| 5 | (CH₃)₂N | cyclohexane | COO | phenyl, F | OCF₂CFHCF₃ |
| 6 | C₃H₇ | dioxane | COO | phenyl, F | OCF₂CFHCF₃ |
| 7 | C₅H₁₁ | cyclohexane | COO | phenyl, F, F | OCF₂CFHCF₃ |
| 8 | isobutyl | cyclohexane | COO | phenyl, F | OCF₂CFHCF₃ |

Further, as to preparation of compounds not described in detail in the above description, intended compounds can be prepared by selecting and combining the above-mentioned reactions or various chemical reactions from books or known literatures.

EXAMPLES

The preparation method and the use examples of the compounds according to the invention are illustrated in more detail as follows. In Examples, C denotes crystals, N denotes nematic phase, S denotes smectic phase and I denotes isotropic liquid, and units of phase transfer temperatures are all in °C.

Example 1

Synthesis of 3-Fluoro-4-(1,1,2,2-Tetrafluoroethoxy) Phenyl=4-(Trans-4-Propylcyclohexy)Benzoate (Compound Number 10)

(the first step)

Under nitrogen atmosphere, 16.4 mL of a solution of n-butyl lithium in n-hexane (1.6 mol/L; 26.3 mmol) was added dropwise for 16 minutes to a solution of 7.28 g (25 mmol) of 3-fluoro-4-(1,1,2,2-tetrafluoroethoxy) bromobenzene in 50 mL of ether at −78° C. At the same temperature, stirring was carried out for 10 minutes. The lithiated compound thus prepared as above was added dropwise for 3 minutes to a solution of 5.17 g (27.5 mmol) of trimethyl borate in 25 mL of ether. While raising the temperature gradually to the room temperature, the reactants were stirred for one night, thereafter cooled to −20° C., and then 1.6 mL of acetic acid was added. 2.81 mL of 30 wt % aqueous hydrogen peroxide solution was diluted with 2.8 mL of water and added dropwise for 2 minutes. While raising the temperature gradually to the room temperature, the reactants were stirred for one night, thereafter added to 100 mL of 10% aqueous sodium hydrogen sulfite solution, filtered through Celite, then the filtrate was separated and extracted from an aqueous phase with ether for three times. Organic phases were combined and dried with magnesium sulfate. After filtering off magnesium sulfate, the filtrate was concentrated under reduced pressure, to obtain 6.03 g of residue. It was purified with silicon gel column chromatography (toluene:ethyl acetate=5:1), and distilled off under reduced pressure, to obtain 4.24 g (yield 74.0%) of 3-fluoro-4-(1,1,2,2-tetrafluoroethoxy)phenol.

(the second step)

2.05 g (9 mmol) of 3-fluoro-4-(1,1,2,2-tetrafluorethoxy) phenol obtained in the first step, 2.22 g (9 mmol) of 4-(trans-4-propylcyclohexy)benzoic acid, 0.33 g (2.7 mmol) of DMAP and 30 mL of dichloromethane were mixed. To the mixture, a solution of 2.23 g (10.8 mmol) of DCC in 2.23 g (10.8 mmol) of dichloromethane was added dropwise for 6 minutes at the room temperature and stirred for 8.5 hours. Crystals precipitated were filtered off, and the filtrate was concentrated under reduced pressure to obtain the residue, to which 10 mL of toluene was added. It was washed with 6 mL of 2N aqueous sodium hydroxide solution for three times, then with 10 mL of 10% aqueous sodium hydrogen carbonate once, and dried with magnesium sulfate. After filtering off magnesium sulfate, the filtrate was concentrated under reduced pressure, and then the residue was purified with silica gel column chromatography (heptane:ethyl acetate= 10:1), recrystallized from a mixed solvent of heptane and ethyl alcohol, to obtain 3.49 g (yield 85.0%) of the title compound.

The said compound shows liquid crystal phase and a transition temperatures thereof are as follows: C-N point: 109.9–110.1, N-I point: 167.0–167.1.

¹H-NMR(CDCl₃) δ (ppm): 814–6.96 (m, 7H), 6.60–5.35 (m, 1H), 2.72–0.77 (m, 22H) mass spectrometry: 456 (M⁺)

According to the method in Example 1, 3-fluoro-4-(1,1,2,2-tetrafluoroethoxy)phenyl=2,6-difluoro-4-(trans-4-pentylcyclohexy)benzoate (compound number 16) wherein at least one of $Z^1$, $Z^2$ and $Z^3$ being —COO— can be produced. Further, the compounds of compound numbers 1 to 89 can be produced according to the above-mentioned procedures.

Herein, the respective compounds are expressed by selecting parameters $R^1$, $A^1$, $Z^1$, $A^2$, $Z^2$, $A^3$, $Z^3$, $A^4$ and $Y^1$ in the general formula (1), which are similar in the following example.

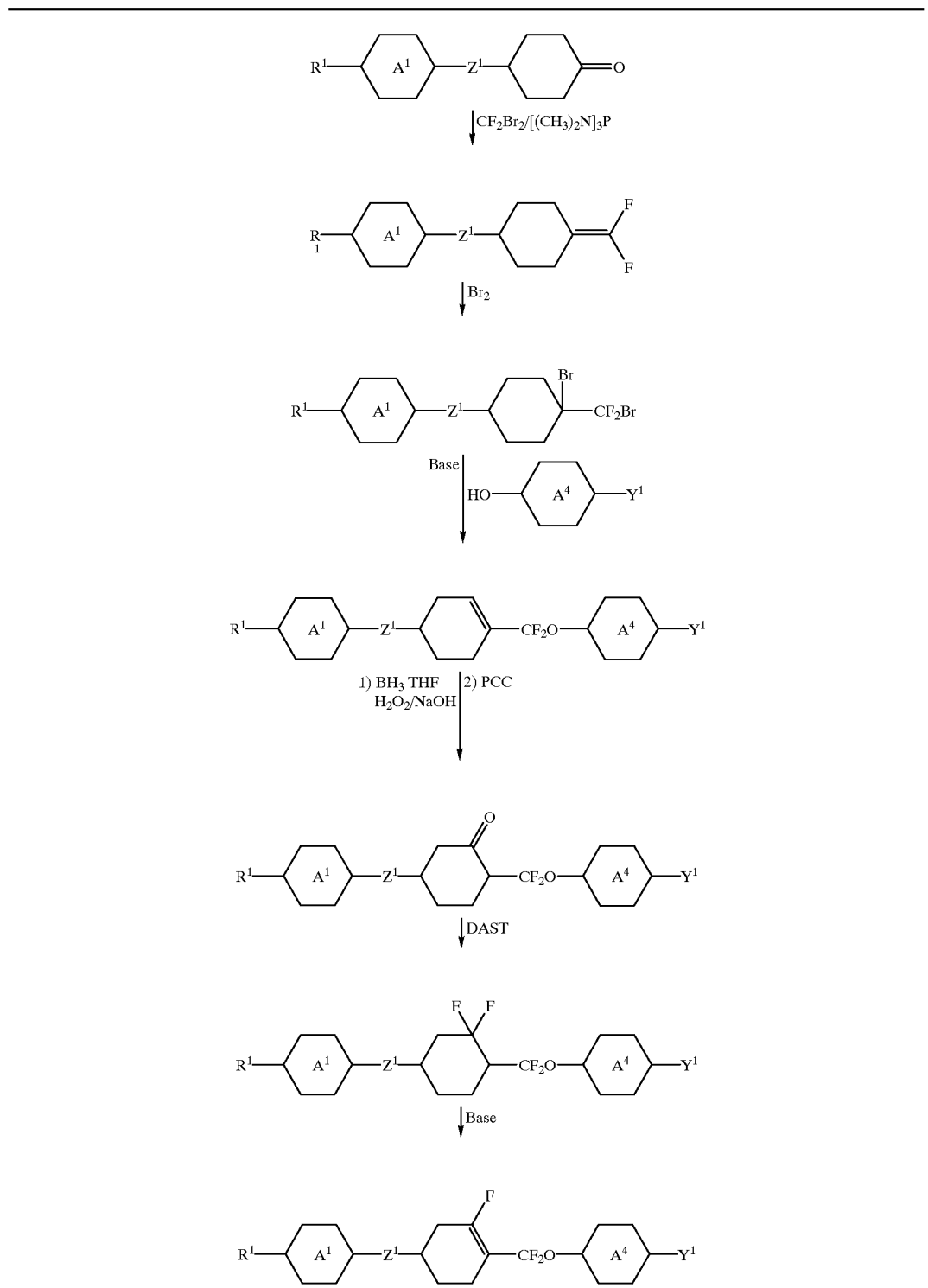

-continued
| No. | A¹ | A¹ | Z¹ | A² | Z² | A³ | Y¹ |
|---|---|---|---|---|---|---|---|
| 9 | $C_3H_7$ | 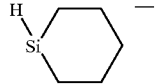 | — |  | $CO_2$ | 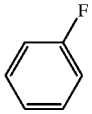 | $OCF_2CF_2H$ |
| 10 | $C_3H_7$ |  | — |  | $CO_2$ | 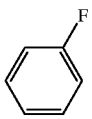 | $OCF_2CF_2H$ CN: 109.9–110.1, NI: 167.0–167.1 |
| 11 | $C_3H_7$ |  |  | — | $CO_2$ | 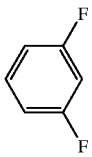 | $OCF_2CF_2H$ |
| 12 | 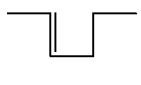 | 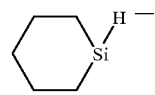 | — |  | $CO_2$ | 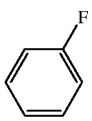 | $OCF_2CFHCF_3$ |
| 13 | $C_3H_7$ |  | — |  | $CO_2$ | 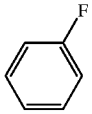 | $OCF_2CFHCF_3$ |
| 14 | $C_3H_7$ |  | — |  | $CO_2$ | 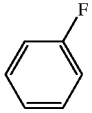 | $OCF_2CFHCF_3$ |
| 15 |  |  | — |  | $CO_2$ | 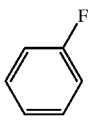 | $OCF_2CF_2H$ |
| 16 | $C_5H_{11}$ |  | — | 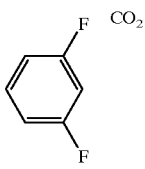 | $CO_2$ | 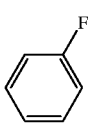 | $OCF_2CF_2H$ CN: 57.2–57.4, NI: 129.0–129.3 |
| 17 | $C_5H_{11}$ |  | — |  | $CO_2$ | 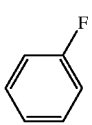 | $OCF_2CF_2H$ |

-continued
| 18 | C₅H₁₁ |  | — | 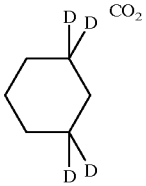CO₂ | 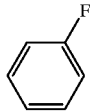F | OCF₂CFHCF₃ |
| 19 | C₅H₁₁ |  | — | CO₂ | 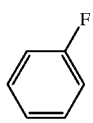F | OCF₂CFHCF₃ |
| 20 | C₅H₁₁ |  | — | CO₂ | 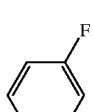F | OCF₂CFHCF₃ |
| 21 | C₃H₇ |  | 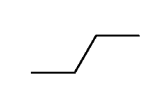 | CO₂ | 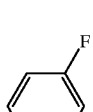F | OCF₂CF₂H |
| 22 | C₃H₇ |  | 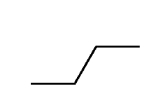 | CO₂ | 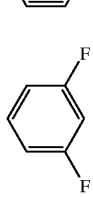F,F | OCF₂CF₂H |
| 23 | 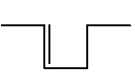 |  | 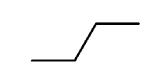 | CO₂ | 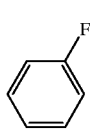F | OCF₂CF₂H |
| 24 | C₃H₇ |  | 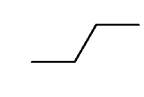 | CO₂ | 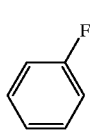F | OCF₂CFHCF₃ |
| 25 | C₃H₇ |  | 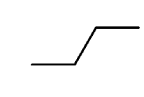 | CO₂ | 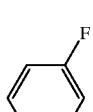F | OCF₂CFHCF₃ |
| 26 | C₃H₇ |  | 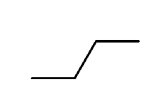 | CO₂ | 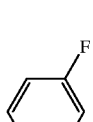F | OCF₂CFHCF₃ |
| 27 | C₃H₁₁ |  | 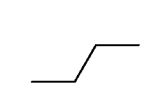 | CO₂ | 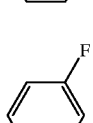F | OCF₂CF₂H |
| 28 |  |  | 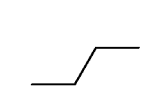 | CO₂ | 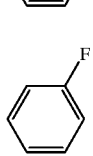F | OCF₂CF₂H |

-continued
| | | | | | | | |
|---|---|---|---|---|---|---|---|
| 29 | C$_5$H$_{11}$ |  | 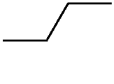 |  | CO$_2$ | 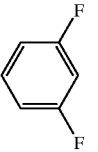 | OCF$_2$CF$_2$H |
| 30 | C$_5$H$_{11}$ |  | 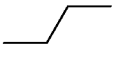 |  | CO$_2$ | 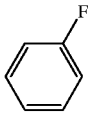 | OCF$_2$CFHCF$_3$ |
| 31 | C$_5$H$_{11}$ |  | 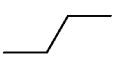 |  | CO$_2$ | 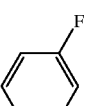 | OCF$_2$CFHCF$_3$ |
| 32 |  |  | 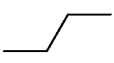 |  | CO$_2$ | 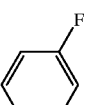 | OCF$_2$CFHCF$_3$ |
| 33 | C$_3$H$_7$ |  | 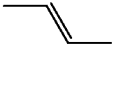 |  | CO$_2$ | 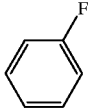 | OCF$_2$CF$_2$H |
| 34 | C$_3$H$_7$ |  | 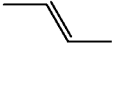 |  | CO$_2$ | 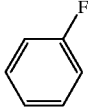 | OCF$_2$CF$_2$H |
| 35 | C$_3$H$_7$ |  | 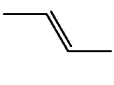 |  | CO$_2$ | 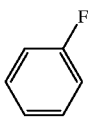 | OCF$_2$CF$_2$H |
| 36 | C$_3$H$_7$ |  | 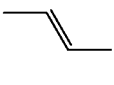 |  | CO$_2$ | 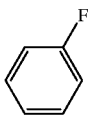 | OCF$_2$CFHCF$_3$ |
| 37 | C$_3$H$_7$ |  | 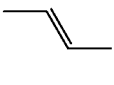 |  | CO$_2$ | 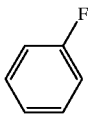 | OCF$_2$CFHCF$_3$ |
| 38 | C$_3$H$_7$ |  | 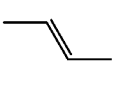 |  | CO$_2$ | 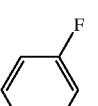 | OCF$_2$CFHCF$_3$ |
| 39 | C$_5$H$_{11}$ |  | 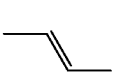 |  | CO$_2$ | 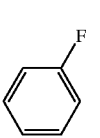 | OCF$_2$CF$_2$H |

-continued

| No. | R¹ | A¹ | Z¹ | A² | Z² | A³ | Z³ | A⁴ | Y¹ |
|---|---|---|---|---|---|---|---|---|---|
| 40 | C₅H₁₁ | cyclohexyl | CH=CH | phenyl | CO₂ | | | F-phenyl | OCF₂CF₂H |
| 41 | C₅H₁₁ | phenyl | CH=CH | phenyl | CO₂ | | | F-phenyl | OCF₂CF₂H |
| 42 | C₅H₁₁ | cyclohexyl | CH=CH | cyclohexyl | CO₂ | | | F-phenyl | OCF₂CFHCF₃ |
| 43 | C₅H₁₁ | cyclohexyl | CH=CH | phenyl | CO₂ | | | F-phenyl | OCF₂CFHCF₃ |
| 44 | C₅H₁₁ | phenyl | CH=CH | phenyl | CO₂ | | | F-phenyl | OCF₂CFHCF₃ |

| No. | R¹ | A¹ | Z¹ | A² | Z² | A³ | Z³ | A⁴ | Y¹ |
|---|---|---|---|---|---|---|---|---|---|
| 45 | C₃H₇ | dioxane | — | phenyl | CO₂ | phenyl | — | F,F-phenyl | OCF₂CF₂H |
| 46 | C₃H₇ | phenyl | — | F-phenyl | CO₂ | F-phenyl | — | F,F-phenyl | OCF₂CFHCF₃ |
| 47 | C₃H₇ | phenyl | CH₂CH₂ | phenyl | CO₂ | phenyl | — | F-phenyl | OCF₂CFHCF₃ |
| 48 | C₃H₇ | cyclohexyl | CH=CH | phenyl | CO₂ | phenyl | — | F-phenyl | OCF₂CF₂H |
| 49 | CH=CH-CH₂- | phenyl | CH=CH | F-phenyl | CO₂ | F-phenyl | — | F,F-phenyl | OCF₂CFHCF₃ |

-continued

| | R | Ring1 | Link1 | Ring2 | Link2 | Ring3 | Ring4-X |
|---|---|---|---|---|---|---|---|
| 50 | $C_5H_{11}$ | Cyclohexyl | — | Phenyl-$CO_2$ | — | Phenyl | 2-$OCF_2CF_2H$-4-F-phenyl |
| 51 | $C_5H_{11}$ | Cyclohexyl | $(CH_2)_2$ | Phenyl-$CO_2$ | — | Phenyl | 2-$OCF_2CF_2H$-phenyl |
| 52 | $C_5H_{11}$ | Cyclohexyl | $(CH_2)_2$ | Phenyl-$CO_2$ | — | Phenyl | 2-$OCF_2CFHCF_3$-phenyl |
| 53 | $CH_2=CH-$ | Cyclohexyl | $CH=CH$ | 2-F-phenyl-$CO_2$ | — | Phenyl | 2-$OCF_2CF_2H$-4-F-phenyl |
| 54 | $C_3H_7$ | Cyclohexyl | — | Cyclohexyl-$CO_2$ | — | Phenyl-$(CH_2)_2$ | 2-$OCF_2CF_2H$-phenyl |
| 55 | $CH_2=CH-$ | Cyclohexyl | $(CH_2)_2$ | Cyclohexyl-$CO_2$ | — | Phenyl-$(CH_2)_2$ | 2-$OCF_2CF_2H$-phenyl |
| 56 | $C_3H_7$ | Cyclohexyl | $CH=CH$ | Cyclohexyl-$CO_2$ | — | Phenyl | 2-$OCF_2CF_2H$-phenyl |
| 57 | $CH_2=CHCH_2-$ | Cyclohexyl | — | Cyclohexyl-$CO_2$ | — | Phenyl | 2-$OCF_2CFHCF_3$-phenyl |
| 58 | $C_3H_7$ | Cyclohexyl | $(CH_2)_2$ | Cyclohexyl-$CO_2$ | — | Phenyl-$(CH_2)_2$ | 2-$OCF_2CFHCF_3$-phenyl |
| 59 | $C_3H_7$ | Cyclohexyl | $CH=CH$ | Cyclohexyl-$CO_2$ | — | Phenyl-$(CH_2)_2$ | 2-$OCF_2CFHCF_3$-phenyl |
| 60 | $CH_2=CHCH_2-$ | Cyclohexyl | — | Cyclohexyl-$CO_2$ | — | Phenyl | 2-$OCF_2CF_2H$-phenyl |

-continued
| 61 | C$_5$H$_{11}$ |  |  | CO$_2$ |  | — |  OCF$_2$CF$_2$H |
| 62 |  |  |  | CO$_2$ |  |  |  OCF$_2$CF$_2$H |
| 63 | C$_5$H$_{11}$ |  | — |  CO$_2$ |  |  |  OCF$_2$CFHCF$_3$ |
| 64 | C$_5$H$_{11}$ |  |  | CO$_2$ |  | — |  OCF$_2$CFHCF$_3$ |
| 65 |  |  |  | CO$_2$ |  | — |  OCF$_2$CFHCF$_3$ |
| 66 |  |  | — |  | — |  CO$_2$ |  OCF$_2$CF$_2$H |
| 67 | C$_3$H$_7$ |  | — |  |  F CO$_2$ |  OCF$_2$CFHCF$_3$ |
| 68 | C$_5$H$_{11}$ |  | — |  |  CO$_2$ |  OCF$_2$CF$_2$H |
| 69 | C$_5$H$_{11}$ |  | — |  | — |  CO$_2$ |  OCF$_2$CFHCF$_3$ |
| 70 | C$_3$H$_7$ |  |  |  |  |  CO$_2$ |  OCF$_2$CF$_2$H |
| 71 |  |  |  |  |  |  CO$_2$ |  OCF$_2$CFHCF$_3$ |

-continued
| | | | | | |
|---|---|---|---|---|---|
| 72 | C$_5$H$_{11}$ |  | 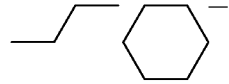 | 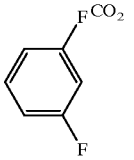 | 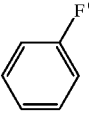 |
| 73 | C$_5$H$_{11}$ |  | 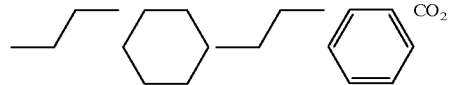 | 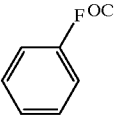 |  |
| 74 | C$_3$H$_7$ | 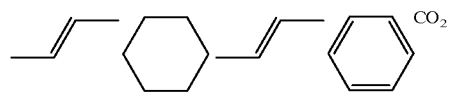 | 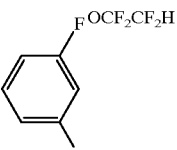 |  | 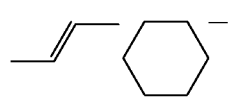 |
| 75 | C$_3$H$_7$ | 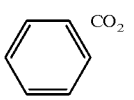 | 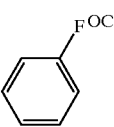 |  |  |
| 76 | 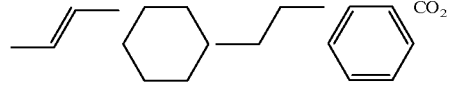 | 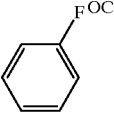 |  | 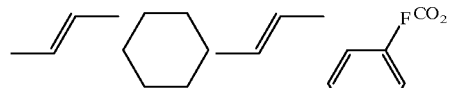 | 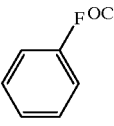 |
| 77 | C$_5$H$_{11}$ |  |  | 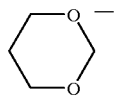 |  |
| 78 | 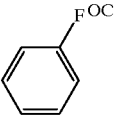 |  |  | 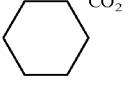 | 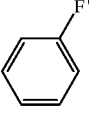 |
| 79 | C$_3$H$_7$ |  |  | 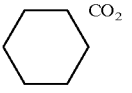 | 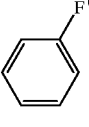 |
| 80 | C$_5$H$_{11}$ |  |  | | 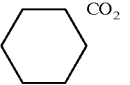 |
| 81 | C$_5$H$_{11}$ | 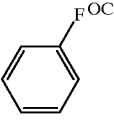 |  | |  |
| 82 | C$_3$H$_7$ | 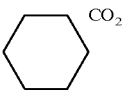 | | | 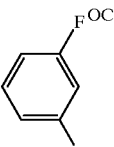 |

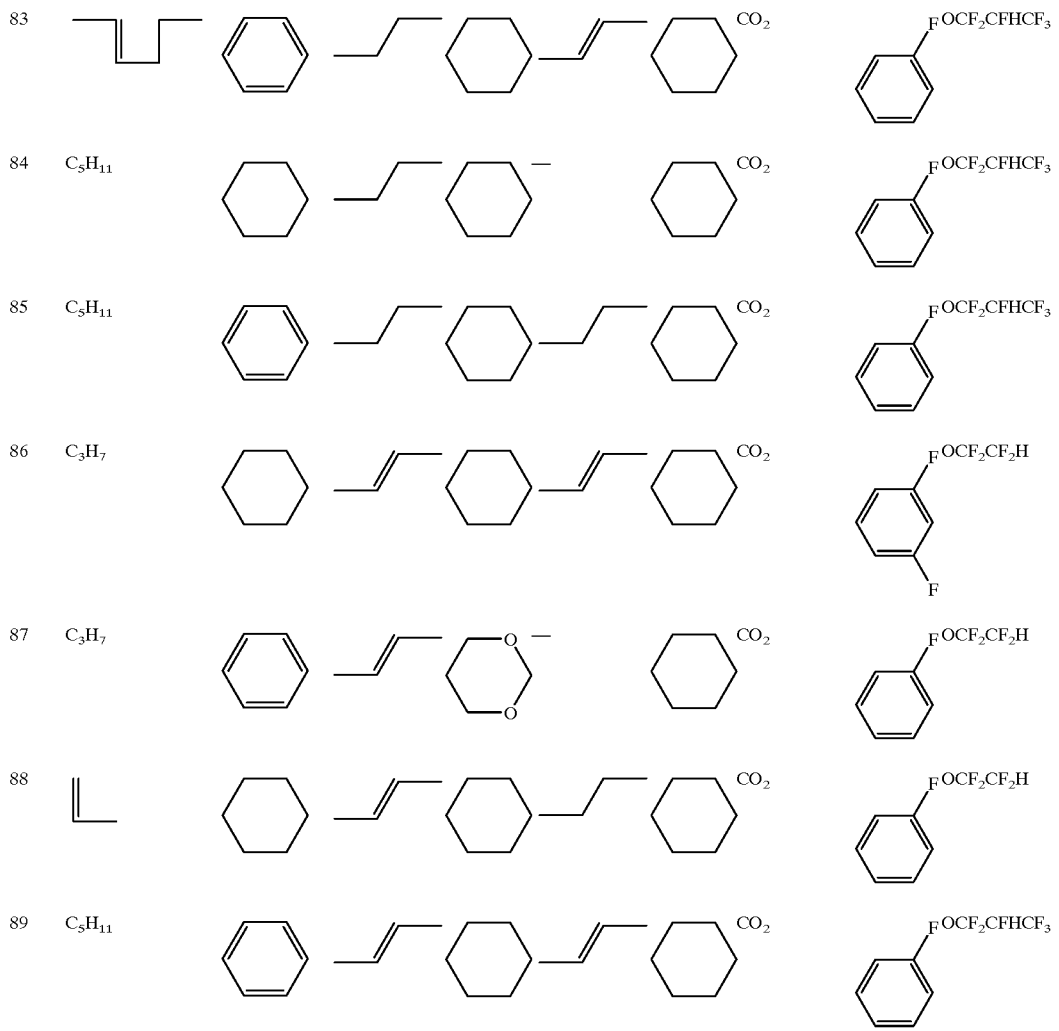

Example 2

Synthesis of 3-Fluoro-4-(1,1,2,2-Tetrafluoroethoxy)Phenyloxy-(4-(Trans-4-Propylcyclohexyl)Phenyl)Difluoromethane (Compound Number 110)

(the first step)

To a solution obtained by suspending 2.25 g (93 mmol) of magnesium in 50 mL of THF, a solution of 20.0 g (71 mmol) of 4-(trans-4-propylcyclohexyl)phenyl bromide in 100 mL of THF was added dropwise with stirring at the room temperature for 45 minutes and stirred with reflux for 30 minutes, to prepare a Grignard reagent. To the solution, 16.3 g (214 mmol) of carbon disulfide was added dropwise for 15 minutes at the room temperature and stirred for one night. To the reaction solution, 60 mL of 3M hydrochloric acid was added to stop the reaction, extracted with ether, and dried with anhydrous magnesium sulfate. After filtering off magnesium sulfate, the filtrate was concentrated under reduced pressure, to obtain 3.5 g (yield 17.7%) of 4-(trans-4-propylcyclohexy)phenyl dithiocarboxylic acid.

(the second step)

1.14 g (26.3 mmol) of 60% sodium hydride was suspended in 15 mL of THF, and a solution of 3.30 g (11.9 mmol) of 4-(trans-4-propylcyclohexyl)phenyl dithiocarboxylic acid in 10 mL of THF was added for 55 minutes, and stirred for 45 minutes. To the reaction solution, a solution of 2.5 g (9.86 mmol) of 3-fluoro-4-(1,1,2,2-tetrafluoroethoxy)phenol in 10 mL of THF was added dropwise and stirred for 1.5 hours. To the reaction solution, a solution of 6.66 g (26.2 mmol) of iodine in 15 mL of THF was added dropwise for 1.5 hours and stirred for 2 hours, and thereafter returned to the room temperature and stirred for one night at the same temperature. The reaction solution was poured into 100 mL of 3M hydrochloric acid, extracted with 100 mL of toluene, and dried with anhydrous magnesium sulfate. After filtering off magnesium sulfate, the filtrate was concentrated under reduced pressure, and the residue was purified with silica gel column chromatography (eluting solvent: heptane), to obtain 1.96 g (yield 52.1%) of 3-fluoro-4-(1,1,2,2-tetrafluoroethoxy)phenyl-4-(trans-4-propylcyclohexyl)thiobenzoate.

(the third step)

1.48 g (8.31 mmol) of N-bromosuccinimide was suspended in 10 mL of methylene chloride, to which 1.65 g of hydrogen fluoride—pyridine were added dropwise for 5 minutes at −78° C., and stirred out for 15 minutes. To the reaction solution, a solution of 1.96 g (4.15 mmol) of 3-fluoro-4-(1,1,2,2-tetrafluoroethoxy)phenyl=4-(trans-4-propylcyclohexyl)thiobenzoate in 15 mL of methylene chloride was added dropwise for 35 minutes and stirred for 2.5 hours. The reaction solution was poured into 150 mL of a saturated aqueous sodium carbonate solution to stop the reaction, and then the methylene chloride phase was separated, washed successively with 100 mL of 10% aqueous sodium hydrogen sulfite and 100 mL of water, and then dried with anhydrous magnesium sulfate. After filtering off magnesium sulfate, the filtrate was concentrated under reduced pressure, and the residue was purified twice with silica gel column chromatography (eluting solvent:heptane), to obtain 0.7 g (yield 35.5%) of the title compound.

The compound shows liquid crystal phase and the transition temperature thereof was as follows:

C-N point: 58.2, N-I point: 65.0.

$^1$H-NMR(CDCl$_3$)

δ (ppm: 7.71–7.06 (m, 7H), 6.61–5.36 (m, 1H), 2.69–0.87 (m, 17H)

$^{19}$F-NMR(CDCl$_3$)

δ (ppm: −66.2 (s, —CF$_2$O—)

mass spectrometry: 452 (M$^+$)

Example 3

Synthesis of 3,4,5-Trifluorophenyloxy-(Trans-4-(Trans-4-Propylcyclohexy)cyclohexy) Difluoromethane (Compound Number 123)

(the first step)

10.0 g (26.1 mmol) of 3,4,5-trifluorophenyl=trans-4-(trans-4-propylcyclohexy)cyclohexyl carboxylate and 11.6 g (28.8 mmol) of Lawessen's reagent were dissolved into 50 mL of toluene, and reacted in a sealed tube at 150° C. for 15 hours. After cooling to the room temperature, water was added to stop the reaction, reactants were extracted with diethyl ether and then the organic phase was dried with anhydrous magnesium sulfate. After filtering off magnesium sulfate, the filtrate was concentrated under reduced pressure, and the residue was purified with silica gel column chromatography (eluting solvent:heptane), to obtain 3.5 g (yield 33.6%) of 3,4,5-trifluorophenyl=trans-4-(trans-4-propylcyclohexyl)cyclohexyl thiocarboxylate.

(the second step)

3.13 g (17.6 mmol) of N-bromosuccinimide was suspended in 10 mL of methylene chloride, then 3.49 g of hydrogen fluoride—pyridine were added dropwise for 5 minutes at −78° C. and stirred for 15 minutes. To the reaction solution, a solution of 3.5 g (8.78 mmol) of 3,4,5-trifluorophenyl=trans-4-(trans-4-propylcyclohexyl)cyclohexyl thiocarboxylate obtained in the first step in 15 ml of methylene chloride was added dropwise for 35 minutes, and stirred for 2.5 hours. The reaction solution was poured into 150 mL, of a saturated aqueous sodium carbonate solution to stop the reaction, and the methylene chloride phase was separated, washed successively with 100 mL of 10% aqueous sodium hydrogen sulfite solution and 100 mL of water, and dried with anhydrous magnesium sulfate. After filtering off magnesium sulfate, the filtrate was concentrated under reduced pressure, and the residue was purified with silica gel column chromatography (eluting solvent:heptane), to obtain 1.5 g (yield 42.3%) of the title compound.

The compound shows liquid crystal phase and the transition temperature thereof were as follows:

C-N point: 43.5, N-I point: 103.0.

$^1$H-NMR(CDCl$_3$)

δ (ppm): 6.83 (m, 2H), 2.20–0.60 (m, 27H)

$^{19}$F-NMR(CDCl$_3$)

δ (ppm): −79.4 (s, 2F, —CF$_2$O—), −133.8(m, 2F), −165.4 (m, 1F)

mass spectrometry: 404 (M$^+$15%), 256(46), 148(18), and 83(100)

Example 4

Synthesis of 3,4,5-Trifluorophenyloxy-(Trans-4-(trans-4-Pentylcyclohexyl)Cyclohexyl) Difluoromethane (Compound Number 124)

By using 3,4,5-trifluorophenyl=trans-4-(trans-4-pentylcyclohexyl)cyclohexyl carboxylate instead of 3,4,5-trifluorophenyl=trans-4-(trans-4-propylcyclohexyl)cyclohexyl carboxylate used in Example 3, the similar procedures to Example 3 were carried out, to obtain 1.5 g of 3,4,5-trifluorophenyloxy-(trans-4-(trans-4-pentylcyclohexyl)cyclohexyl)difluoromethane.

The compound shows liquid crystal phase and the transition temperature thereof were as follows:

C-N point: 57.6, N-I point: 111.5.

$^1$H-NMR(CDCl$_3$)

δ (ppm): 6.82 (m,2H), 0.6–2.2 (m, 31H)

$^{19}$F-NMR(CDCl$_3$)

δ (ppm): −79.13 (s,2F, —CF$_2$O—), −133.69(m, 2F), −165.15(m, 1F)

mass spectrometry: 432 (M$^+$, 11.8%), 284(28.5), 213 (4.9), 173(5.6), 148(16.5), 111(29.3), 97(81.8), 83(100), 69(61.1), 55(62.6), and 41(30.6)

Example 5

Synthesis of 4-Trifluoromethoxyphenyloxy-(Trans-4-Trans-4-Pentylcyclohexyl)Cyclohexyl) Difluoromethane (Compound Number 127)

By using 4trifluoromethoxyphenyl=trans-4-(trans-4-pentylcyclohexyl)cyclohexyl) carboxylate instead of 3,4,5 trifluorophenyl=trans-4-(trans-4-propylcyclohexyl)cyclohexyl carboxylate used in Example 3, the similar procedures to Example 3 were carried out, to obtain 1.5 g of 4-trifluoromethoxyphenyloxy-(trans-4-(trans-4-pentylcyclohexyl)cyclohexyl)difluoromethane.

The compound shows liquid crystal phase and the transition temperature thereof were as follows;

C-S point: 35.1, S-N point: 116.7, N-I point: 156.9.

$^1$H-NMR(CDCl$_3$)

δ (ppm): 7.19 (bs, 4H), 0.6–2.2 (m, 31H)

$^{19}$F-NMR(CDCl$_3$)

δ (ppm): −58.68 (s,3F, —OCF$_3$), −78.77(s, 2F, —CF$_2$O—)

Example 6

Synthesis of 3,4,5-Trifluorophenyloxy-(4-(Trans-4-Pentylcyclohexyl)Cyclohexen-1-Yl) Difluoromothane (Compound Number 279)

(the first step)

Under nitrogen atmosphere, 18.9 g (89.9 mmol) of dibromodifluoromethane was dissolved in 100 ml of THF and cooled to −60° C. or less by a coolant, and a solution of 29.4 g (179.9 mmol) of hexamethylphosphorus triamide dissolved in 80 ml of THF was added dropwise with keeping the temperature at −60° C. The solution was stirred with keeping the same temperature for 2 hours and heated to the room temperature, and thereafter a solution of 11.3 g (44.9 mmol) of 4-(trans-4-pentylcyclohexyl)cyclohexanone in 50 ml of THF solution. After stirring at the room temperature for 2 hours, heating under reflux was carried out for 10 hours. The reaction solution was poured into 300 ml of water, and the reactants were extracted with 300 ml of heptane and the extracted layer was washed successively with 100 ml of a saturated aqueous sodium carbonate solution and 300 ml of a saturated aqueous sodium chloride solution, dried with anhydrous magnesium sulfate, distilled off the solvent under reduced pressure and concentrated, to obtain a pale yellow oily substance. The reactant obtained was purified with silica gel column chromatography (eluting solvent:heptane), to obtain 12.2 g of α, α-difluoromethylene-4-(trans-4-pentylcyclohexyl) cyclohexylidene as colorless oil.

(the second step)

12.2 g (43.0 mmol) of α, α(difluoromethylene-4-(trans-4-pentylcyclohexyl)cyclohexylidene obtained as above was dissolved in 50 ml of dichloromethane, cooled to 10° C. or less with stirring, and thereafter 6.8 g (43.0 mmol) of bromine was added dropwise. After stirring for 10 minutes at 10° C. or less, 50 ml of water was added to stop the reaction. The reaction solution was extracted with 150 ml of heptane, washed successively with 50 ml of 10% aqueous sodium thiosulfate solution and a saturated aqueous sodium chloride solution, and thereafter dried with anhydrous magnesium sulfate. After filtering off magnesium sulfate, the filtrate was concentrated under reduced pressure and the residue was purified with silica gel column chromatography (developing solvent:heptane), to obtain 16.3 g (36.6 mmol) of 1-bromo-1-bromodifluoromethyl-4-(trans-4-pentylcyclohexyl)cyclohexane as colorless oil.

(the third step)

16.3 g (36.6 mmol) of 1-bromo-1-bromodifluoromethyl-4-(trans-4-pentylcyclohexyl)cyclohexane obtained as above, 6.1 g (43.8 mmol) of potassium carbonate, 0.1 g (0.6 mmol) of potassium iodide and 6.5 g (43.8 mmol) of 3,4,5-trifluorophenol were suspended in 50 ml of DMF, and heated under reflux for 2 hours. 100 ml of water was added to the reaction solution, the reactants were extracted with 150 ml of heptane, and the extracted layer was washed with 200 ml of water and dried with magnesium sulfate. After filtering off magnesium sulfate, the filtrate was concentrated under reduced pressure, and the residue was purified with silica gel column chromatography (developing solvent:heptane) and then recrystallized from heptane, to obtain 4.5 g of 3,4,5-trifluorophenyloxy-4-(trans-4-pentylcyclohexyl)cyclohexen-1-yl)difluoromethane (compound number 279) as colorless needles.

The compound shows liquid crystal phase and the transition temperature thereof were as follows:

C-N point: 37.3, N-I point: 62.1.

$^1$H-NMR(CDCl$_3$)

δ (ppm): 0.6–2.5 (m, 28H), 6.34 (bs, 1H), 6.85 (m, 2H)

$^{19}$F-NMR(CDCl$_3$)

δ (ppm): −73.61 (s, 2F, —CF$_2$O—), −133.54(m, 2F), −164.97(m, 1F)

mass spectrometry: 410 (M$^+$—HF, 0.5%), 283(15.6), 263 (22.9), 243(25.0), 131(17.9), 111(36.6), 97(70.8), 83(86.5), 69(66.6), 55(100), 41(83.7), and 29(39.6)

Example 7

Synthesis of 3,4,5 Trifluorophenyloxy-(2-Fluoro-(Trans-4-Propylcyclohexyl)Cyclohexen-1-Yl) Difluoromothane (Compound Number 282)

(the first step)

15.0 g (37.27 mmol) of 3,4,5-trifluorophenyloxy-(4-(trans-4-propylcyclohexyl)cyclohexen-1-yl) difluoromethane obtained by the similar procedures in Example 4 was dissolved in 100 ml of THF and cooled to 0° C., and thereafter 41 ml of 1M solution of borane THF complex was added dropwise. Then, after raising the temperature to the room temperature with stirring, the solution was stirred for 1 hour, to which 10 ml of ethanol, 10 ml of 2N-solution of sodium hydroxide and 15 ml of 30% hydrogen peroxide solution were successively added, and stirred for 4 hours at 60° C. on a hot bath. After adding 100 ml of water to the reaction solution, the solution was extracted with 150 ml of diethyl ether, and thereafter the extracted layer was washed with 50 ml of 10% sodium hydrogen sulfate solution and 100 ml of water, dried with anhydrous magnesium sulfate and concentrated under reduced pressure, to obtain 15.5 g of the product. The concentrate was as such used for the next reaction.

(the second step)

15.5 g of the concentrate obtained in the above-mentioned reaction was dissolved in 100 ml of dichloromethane, and 10.3 g (47.9 mmol) of PCC was added and stirred for 5 hours at the room temperature. After concentrating the product, the residue was purified with silica gel column chromatography (developing solvent: toluene) and further recrystallized from heptane, to obtain 8.7 g of 3,4,5-trifluorophenyloxy-2-(2-oxo-4-(trans-4-propylcyclohexyl)cyclohexyl) difluoromethane.

(the third step)

8.7 g (20.87 mmol) of 3,4,5-trifluorophenyloxy-2-(2-oxo-4-(trans-4-propylcyclohexyl)cyclohexyl)difluoromethane obtained from the above-mentioned reaction was dissolved in 50 ml of dichloromethane, and 4.0 g (25.0 mmol) of DAST was added and refluxed for 2 hours. After the reaction solution was introduced into 50 ml of a saturated aqueous sodium carbonate solution, the solution was extracted with diethyl ether, and the extracted layer was washed with 200 ml of water and dried with anhydrous magnesium sulfate. After filtering off magnesium sulfate, the solvent was distilled off and concentrated, to obtain 8.7 g of the concentrated residue. The concentrated residue was used for the next reaction.

(the fourth step)

The above-mentioned residue was dissolved in 50 ml of DMF, and 2.3 g (20.5 mmol) of potassium-t-butoxide was added and heated at 60° C. for 4 hours with stirring. To the reaction solution 50 ml of water was added, and after the reactants were extracted with 150 ml of diethyl ether the extracted layer was washed with 200 ml of water and dried with anhydrous magnesium sulfate, After filtering off magnesium sulfate, the solvent was distilled off and concentrated, and the concentrated residue was purified with silica gel column chromatography (developing solvent: heptane) and recrystallized from heptane, to obtain 2.7 g of 3,4,5-trifluorophenyloxy-(2-fluoro-(trans-4-propylcyclohexyl) cyclohexen-1-yl)difluoromethane.

The compounds with compound numbers 90 to 504 wherein at least one of Z$^1$, Z$^2$ and Z$^3$ being —CF$_2$O— can be prepared according to the methods described in Examples 2 to 7.

| No. | R¹ | A¹ | Z¹ | A⁴ | Y¹ |
|---|---|---|---|---|---|
| 90 | (alkenyl) | 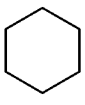 | CF$_2$O | 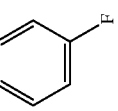 | OCF$_2$CF$_2$H |
| 91 | C$_3$H$_7$ | 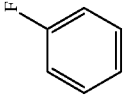 | CF$_2$O | 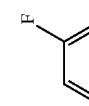 | OCF$_2$CF$_2$H |
| 92 | C$_5$H$_{11}$ | 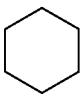 | CF$_2$O | 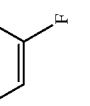 | OCF$_2$CF$_2$H |
| 93 | C$_5$H$_{11}$ | 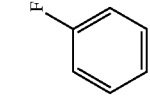 | CF$_2$O | 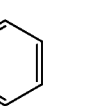 | OCF$_2$CF$_2$H |
| 94 | C$_3$H$_7$ |  | CF$_2$O |  | OCF$_2$CFHCF$_3$ |

| | | | | |
|---|---|---|---|---|
| 95 | C₃H₇ | [cyclohexane with F] | CF₂O | [benzene with 2F] OCF₂CFHCF₃ |
| 96 | C₅H₁₁ | [cyclohexane] | CF₂O | [benzene with F] OCF₂CFHCF₃ |
| 97 | [alkene fragment] | [cyclohexane with F] | CF₂O | [benzene with F] OCF₂CFHCF₃ |
| 98 | C₃H₇ | [cyclohexane] | CF₂O | [benzene] F |
| 99 | C₃H₇ | [cyclohexane] | CF₂O | [benzene with F] F |
| 100 | C₅H₁₁ | [cyclohexane] | CF₂O | [benzene with 2F] F |

-continued

| | | | | |
|---|---|---|---|---|
| 101 | C₅H₁₁ | ⬡ | CF₂O | 3,5-F₂-C₆H₃-CF₃ |
| 102 | C₃H₇ | ⬡ | CF₂O | 3-F-C₆H₄-CF₃ |
| 103 | C₃H₇ | ⬡ | CF₂O | C₆H₅-CF₃ |
| 104 | C₅H₁₁ | ⬡ | CF₂O | 3,5-F₂-C₆H₃-OCF₃ |
| 105 | C₅H₁₁ | ⬡ | CF₂O | 3-F-C₆H₄-OCF₃ |
| 106 | C₃H₇ | ⬡ | CF₂O | C₆H₅-OCF₃ |
| 107 | C₃H₇ | ⬡ | CF₂O | 3,5-F₂-C₆H₃-OCF₂H |

-continued
| No. | R¹ | A¹ | Z¹ | A² | Z² | A³ | Y¹ |
|-----|----|----|----|----|----|----|----|
| 108 | C₅H₁₁ |  | — |  | CF₂O |  | CN |
| No. | R¹ | A¹ | Z¹ | A² | Z² | A³ | Y¹ |
|-----|----|----|----|----|----|----|----|
| 109 | C₃H₇ |  | — | 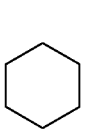 | CF₂O |  | OCF₂CF₂H |
| 110 | C₃H₇ |  | — | 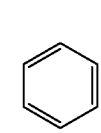 | CF₂O |  | OCF₂CF₂H  CN: 58.2, NI: 65.0 |
| 111 | C₃H₇ |  | 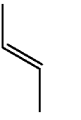 | 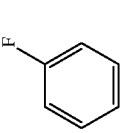 | CF₂O |  | OCF₂CF₂H |
| 112 | C₅H₁₁ |  | — | 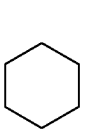 | CF₂O |  | OCF₂CF₂H |

| | | | | | | |
|---|---|---|---|---|---|---|
| 113 | C₅H₁₁ | 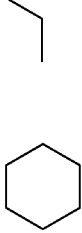 |  | 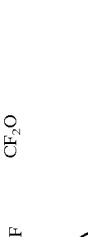 CF₂O |  | OCF₂CF₂H |
| 114 | C₅H₁₁ | 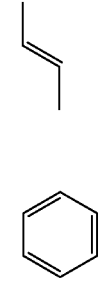 |  |  CF₂O |  | OCF₂CF₂H |
| 115 | C₃H₇ | 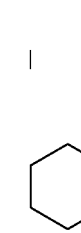 | — |  CF₂O |  | OCF₂CF₂H |
| 116 | C₃H₇ |  |  |  CF₂O | 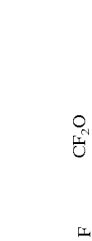 | OCF₂CFHCF₃ |
| 117 | C₃H₇ |  |  |  CF₂O |  | OCF₂CFHCF₃ |
| 118 | C₅H₁₁ |  | — | 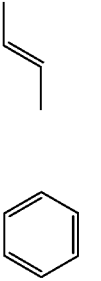 CF₂O |  | OCF₂CFHCF₃ |

-continued

| No. | R¹–A¹–Z¹– | –A²–Z²– | –A³–Z³– | –A⁴–Y¹ | |
|---|---|---|---|---|---|
| 119 | C₅H₁₁–[cyclohexyl]– | –[phenyl(F)]–CF₂O– | –[phenyl(F,F)]– | OCF₂CFHCF₃ | |
| 120 | C₅H₁₁–CH=CH– | –[phenyl(F)]–CF₂O– | –[phenyl(F)]– | OCF₂CFHCF₃ | |

| No. | R¹–A¹–Z¹– | –A²–Z²– | –A³–Z³– | –A⁴–Y¹ | |
|---|---|---|---|---|---|
| 121 | C₃H₇–[cyclohexyl]– | –[cyclohexyl]–CF₂O– | — | –[phenyl(F)] | |
| 122 | C₃H₇–[cyclohexyl]– | –[cyclohexyl]–CF₂O– | — | –[phenyl(F,F)] | |
| 123 | C₃H₇–[cyclohexyl]– | –[cyclohexyl]–CF₂O– | — | –[phenyl(F,F,F)] | CN: 43.5, NI: 103.0 |

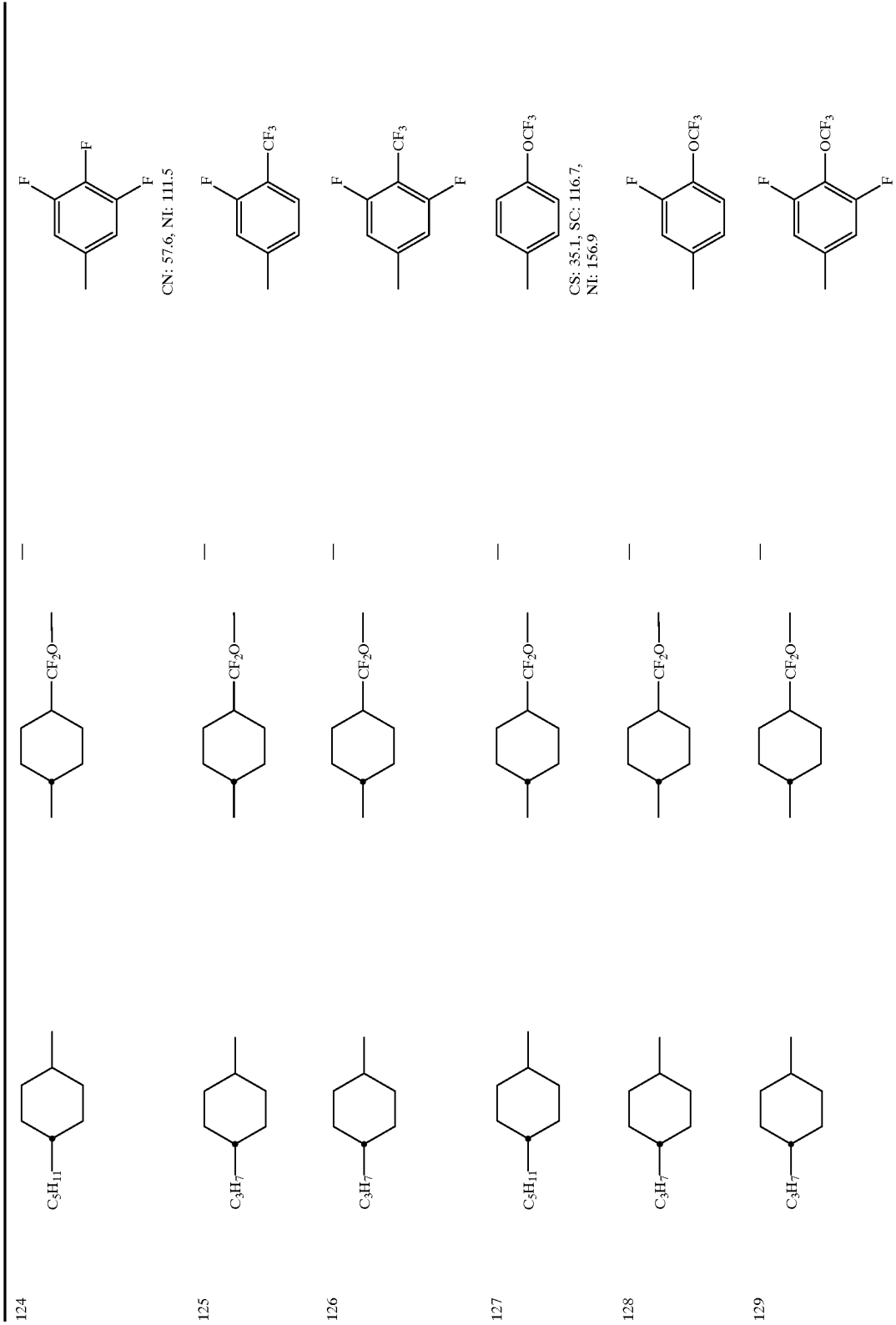

-continued

| No. | R¹ | A¹ | Z¹ | A² | Z² | A³ | Y¹ |
|-----|-----|-----|-----|-----|-----|-----|-----|
| 132 | C₃H₇ | cyclohexyl | (chain) | cyclohexyl | CF₂O | phenyl | F |
| 133 | C₃H₇ | cyclohexyl | (chain) | cyclohexyl | CF₂O | fluorophenyl | F |
| 134 | C₃H₇ | cyclohexyl | (chain) | cyclohexyl | CF₂O | difluorophenyl | F |
| 135 | C₅H₁₁ | cyclohexyl | (chain) | cyclohexyl | CF₂O | phenyl | CF₃ |

-continued

| | | | | | |
|---|---|---|---|---|---|
| 136 | C₅H₁₁ | ⬡ | ⌐ | ⬡ | CF₂O | [F-phenyl-CF₃] |
| 137 | C₅H₁₁ | ⬡ | ⌐ | ⬡ | CF₂O | [3,5-F₂-phenyl-CF₃] |
| 138 | C₃H₇ | ⬡ | ⌐ | ⬡ | CF₂O | [3,5-F₂-phenyl-OCF₃] |
| 139 | C₃H₇ | ⬡ | ⌐ | ⬡ | CF₂O | [F-phenyl-OCF₃] |
| 140 | C₃H₇ | ⬡ | ⌐ | ⬡ | CF₂O | [phenyl-OCF₃] |
| 141 | C₅H₁₁ | ⬡ | ⌐ | ⬡ | CF₂O | [3,5-F₂-phenyl-OCF₂H] |

| | | | | | |
|---|---|---|---|---|---|
| 142 | C$_5$H$_{11}$ | ⬡ | ∿ | ⬡ | CF$_2$O | 3,5-F$_2$-C$_6$H$_3$-CN |
| 143 | C$_3$H$_7$ | ⬡ | ∿ | ⬡ | CF$_2$O | C$_6$H$_5$-F |
| 144 | C$_3$H$_7$ | ⬡ | ∿ | ⬡ | CF$_2$O | 3-F-C$_6$H$_4$-F |
| 145 | C$_3$H$_7$ | ⬡ | ∿ | ⬡ | CF$_2$O | 3,5-F$_2$-C$_6$H$_3$-F |
| 146 | C$_5$H$_{11}$ | ⬡ | ∿ | ⬡ | CF$_2$O | C$_6$H$_5$-CF$_3$ |
| 147 | C$_5$H$_{11}$ | ⬡ | ∿ | ⬡ | CF$_2$O | 3-F-C$_6$H$_4$-CF$_3$ |
| 148 | C$_5$H$_{11}$ | ⬡ | ∿ | ⬡ | CF$_2$O | 3,5-F$_2$-C$_6$H$_3$-CF$_3$ |

-continued

| | | | | | | |
|---|---|---|---|---|---|---|
| 149 | C₃H₇ | ⬡ | ⟋ | ⬡ | CF₂O | ⌬(F,F) | OCF₃ |
| 150 | C₃H₇ | ⬡ | ⟋ | ⬡ | CF₂O | ⌬(F) | OCF₃ |
| 151 | C₃H₇ | ⬡ | ⟋ | ⬡ | CF₂O | ⌬ | OCF₃ |
| 152 | C₅H₁₁ | ⬡ | ⟋ | ⬡ | CF₂O | ⌬(F,F) | OCF₂H |
| 153 | C₅H₁₁ | ⬡ | ⟋ | ⬡ | CF₂O | ⌬(F,F) | CN |
| 154 | C₃H₇ | ⬡ | CF₂O | ⌬ | — | ⌬ | F |

| | | | | |
|---|---|---|---|---|
| 155 | C₃H₇ |  | CF₂O | 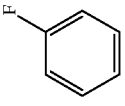 | — | 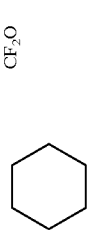 | F |
| 156 | C₃H₇ | 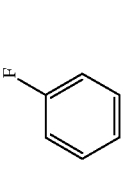 | CF₂O |  | — | 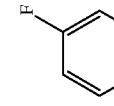 | F |
| 157 | C₅H₁₁ | 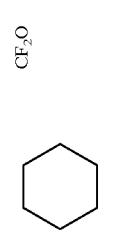 | CF₂O | 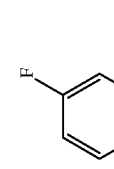 | — | 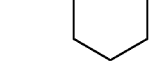 | CF₃ |
| 158 | C₅H₁₁ | 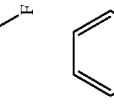 | CF₂O | 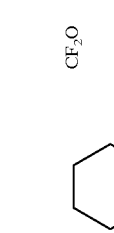 | — | 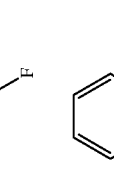 | CF₃ |
| 159 | C₅H₁₁ |  | CF₂O | 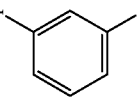 | — | 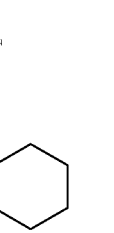 | OCF₃ |

| No. | R¹ | A¹ | Z¹ | A² | Z² | A³ | Z³ | A³ | Y¹ |
|-----|-----|-----|-----|-----|-----|-----|-----|-----|-----|
| 164 | C₃H₇ | 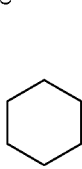 | — | 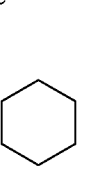 | CF₂O | 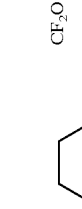 | — |  | F |

-continued
| | | | | | | |
|---|---|---|---|---|---|---|
| 165 | C$_3$H$_7$ |  | — |  CF$_2$O |  | — |  F, F |
| 166 | C$_3$H$_7$ |  | — |  CF$_2$O |  | — |  F, F, F |
| 167 | C$_5$H$_{11}$ |  | — |  CF$_2$O |  | — |  CF$_3$ |
| 168 | C$_5$H$_{11}$ |  | — |  CF$_2$O |  | — |  F, F, CF$_3$ |
| 169 | C$_5$H$_{11}$ |  | — |  CF$_2$O |  | — |  OCF$_3$ |

| | | | | | | | |
|---|---|---|---|---|---|---|---|
| 170 | C_5H_{11} | ⬡ | — | ⬡ | CF_2O | ⏣(F,F) | — | ⏣(F) OCF_3 |
| 171 | C_5H_{11} | ⬡ | — | ⬡ | CF_2O | ⏣(F,F) | — | ⏣(F,F) OCF_3 |
| 172 | C_3H_7 | ⬡ | — | ⬡ | CF_2O | ⏣(F,F) | — | ⏣(F) CN |
| 173 | C_3H_7 | ⬡ | — | ⬡ | CF_2O | ⏣(F,F) | — | ⏣(F,F) CN |
| 174 | C_3H_7 | ⬡ | CH_2CH_2 | ⬡ | CF_2O | ⏣ | — | ⏣(F) F |
| 175 | C_3H_7 | ⬡ | CH_2CH_2 | ⬡ | CF_2O | ⏣(F,F) | — | ⏣(F) F |

| | | | | | | |
|---|---|---|---|---|---|---|
| 176 | C$_3$H$_7$ |  |  |  | CF$_2$O |  — 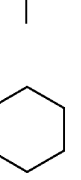 F |
| 177 | C$_5$H$_{11}$ |  |  | 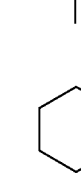 | CF$_2$O |  —  CF$_3$ |
| 178 | C$_5$H$_{11}$ | 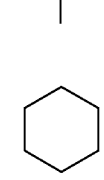 |  |  | CF$_2$O | 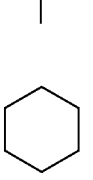 —  CF$_3$ |
| 179 | C$_5$H$_{11}$ |  | 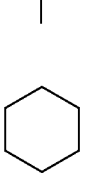 |  | CF$_2$O |  —  OCF$_3$ |
| 180 | C$_3$H$_7$ |  |  |  | CF$_2$O |  —  OCF$_3$ |

-continued
| | | | | | | |
|---|---|---|---|---|---|---|
| 181 | C₃H₇ |  | 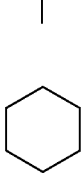 |  | CF₂O |  | — | 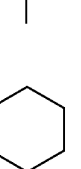 OCF₃ |
| 182 | C₃H₇ |  |  | 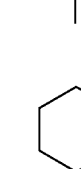 | CF₂O |  | — |  CN |
| 183 | C₃H₇ |  |  |  | CF₂O | 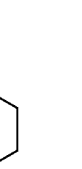 | — |  CN |
| 184 | C₃H₇ |  | 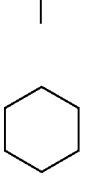 |  | CF₂O |  | — | 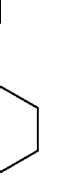 F |
| 185 | C₃H₇ |  |  | 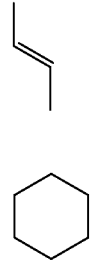 | CF₂O |  | — |  F |
| 186 | C₃H₇ |  |  |  | CF₂O |  | — |  F |

-continued
| | | | | | | | | | |
|---|---|---|---|---|---|---|---|---|---|
| 187 | $C_5H_{11}$ | 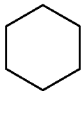 | 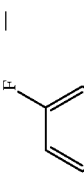 |  | $CF_2O$ | 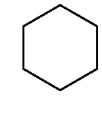 | — | 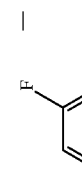 | $CF_3$ |
| 188 | $C_5H_{11}$ |  | 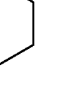 | 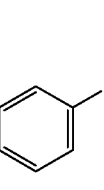 | $CF_2O$ |  | — |  | $CF_3$ |
| 189 | $C_5H_{11}$ |  |  |  | $CF_2O$ |  | — |  | $OCF_3$ |
| 190 | $C_3H_7$ | | | | $CF_2O$ | | — | | $OCF_3$ |
| 191 | $C_3H_7$ | | | | $CF_2O$ | | — | | $OCF_3$ |

| | | | | | | | |
|---|---|---|---|---|---|---|---|
| 192 | $C_3H_7$ |  |  | $CF_2O$ |  | — |  | CN |
| 193 | $C_3H_7$ |  |  | $CF_2O$ |  | — |  | CN |
| 194 | $C_3H_7$ |  | — | $CF_2O$ |  | — |  | $OCF_2CF_2H$ |
| 195 | $C_3H_7$ |  |  | $CF_2O$ |  |  |  | $OCF_2CF_2H$ |
| 196 | $C_3H_7$ |  |  | $CF_2O$ |  |  |  | $OCF_2CF_2H$ |
| 197 | $C_5H_{11}$ |  | — | $CF_2O$ |  | — |  | $OCF_2CF_2H$ |

-continued
| | | | | | | | |
|---|---|---|---|---|---|---|---|
| 198 | C$_5$H$_{11}$ |  |  |  | CF$_2$O |  |  |  | OCF$_2$CF$_2$H |
| 199 | C$_5$H$_{11}$ |  |  |  | CF$_2$O |  |  |  | OCF$_2$CF$_2$H |
| 200 | C$_3$H$_7$ |  | — |  | CF$_2$O |  | — |  | OCF$_2$CFHCF$_3$ |
| 201 | C$_3$H$_7$ |  |  |  | CF$_2$O |  |  |  | OCF$_2$CFHCF$_3$ |
| 202 | C$_3$H$_7$ |  |  |  | CF$_2$O |  |  |  | OCF$_2$CFHCF$_3$ |
| 203 | C$_5$H$_{11}$ |  | — |  | CF$_2$O |  | — |  | OCF$_2$CFHCF$_3$ |
| 204 | C$_5$H$_{11}$ |  |  |  | CF$_2$O |  |  |  | OCF$_2$CFHCF$_3$ |

-continued
| | | | | | | | |
|---|---|---|---|---|---|---|---|
| 205 | C₅H₁₁ | ⌬ | ╱ | ⌬(F) | CF₂O | ⌬ | ╱ | ⌬(F) | OCF₂CFHCF₃ |
| 206 | ╱╲ | ⌬ | — | dioxane | — | ⌬ | CF₂O | ⌬(F) | OCF₂CF₂H |
| 207 | C₅H₁₁ | ⌬ | — | ⌬ | — | ⌬ | CF₂O | ⌬(F,F) | OCF₂CFHCF₃ |
| 208 | C₃H₇ | ⌬ | ╱ | ⌬ | ╱ | ⌬ | CF₂O | ⌬(F) | OCF₂CF₂H |
| 209 | C₅H₁₁ | ⌬ | ╱ | ⌬ | — | ⌬ | CF₂O | ⌬(F) | OCF₂CFHCF₃ |
| 210 | C₃H₇ | ⌬ | ╱ | ⌬ | ╱ | ⌬ | CF₂O | ⌬(F) | OCF₂CF₂H |

-continued

| No. | R1 | Ring A | L1 | Ring B | L2 | Ring C | L3 | Ring D | R2 |
|---|---|---|---|---|---|---|---|---|---|
| 211 | (CH=CH-) | phenyl | CH=CH (trans) | cyclohexyl | CH=CH (trans) | cyclohexyl | CF$_2$O | 3,5-difluorophenyl | OCF$_2$CFHCF$_3$ |
| 212 | C$_3$H$_7$ | 1,3-dioxane | — | phenyl | — | cyclohexyl | CF$_2$O | 3-fluorophenyl | OCF$_2$CF$_2$H |
| 213 | C$_5$H$_{11}$ | phenyl | — | phenyl | — | cyclohexyl | CF$_2$O | 2-fluorophenyl | OCF$_2$CFHCF$_3$ |
| 214 | C$_3$H$_7$ | cyclohexyl | CH$_2$CH$_2$ | phenyl | CH$_2$CH$_2$ | cyclohexyl | CF$_2$O | 3-fluorophenyl | OCF$_2$CF$_2$H |
| 215 | C$_5$H$_{11}$ | phenyl | CH$_2$CH$_2$ | pyrimidine | CH=CH (trans) | cyclohexyl | CF$_2$O | 3,5-difluorophenyl | OCF$_2$CFHCF$_3$ |
| 216 | C$_3$H$_7$ | cyclohexyl | CH=CH (trans) | phenyl | CH=CH (trans) | cyclohexyl | CF$_2$O | 2-fluorophenyl | OCF$_2$CF$_2$H |

| | | | | | | | | |
|---|---|---|---|---|---|---|---|---|
| 217 | C$_5$H$_{11}$ | ⬡(benzene) | —CH=CH— | ⬡(benzene) | — | ⬡(cyclohexane) | CF$_2$O | ⬡(3,5-difluorophenyl) | OCF$_2$CFHCF$_3$ |
| 218 | C$_3$H$_7$ | ⬡(cyclohexane) | — | ⬡(cyclohexane) | —C$_2$H$_4$— | ⬡(benzene) | CF$_2$O | ⬡(2-fluorophenyl) | OCF$_2$CF$_2$H |
| 219 | C$_5$H$_{11}$ | ⬡(benzene) | — | dioxane | —CH=CH— | ⬡(benzene) | CF$_2$O | ⬡(3,5-difluorophenyl) | OCF$_2$CFHCF$_3$ |
| 220 | CH=CH$_2$ | ⬡(cyclohexane) | —C$_2$H$_4$— | ⬡(cyclohexane) | — | ⬡(benzene) | CF$_2$O | ⬡(2-fluorophenyl) | OCF$_2$CF$_2$H |
| 221 | C$_5$H$_{11}$ | ⬡(benzene) | —C$_2$H$_4$— | ⬡(cyclohexane) | — | ⬡(benzene) | CF$_2$O | ⬡(2-fluorophenyl) | OCF$_2$CFHCF$_3$ |
| 222 | C$_3$H$_7$ | ⬡(cyclohexane) | —CH=CH— | ⬡(cyclohexane) | — | ⬡(benzene) | CF$_2$O | ⬡(2-fluorophenyl) | OCF$_2$CF$_2$H |

| No. | R1 | Ring A | L1 | Ring B | L2 | Ring C | L3 | Ring D | R2 |
|---|---|---|---|---|---|---|---|---|---|
| 223 | CH=CH- | phenyl | -CH=CH- | cyclohexyl | -CH=CH- | phenyl | CF$_2$O | phenyl | OCF$_2$CFHCF$_3$ (3,5-diF) |
| 224 | C$_3$H$_7$ | cyclohexyl | — | phenyl | — | phenyl | CF$_2$O | phenyl | OCF$_2$CF$_2$H (3-F) |
| 225 | C$_5$H$_{11}$ | pyrimidinyl | — | phenyl | — | phenyl | CF$_2$O | phenyl | OCF$_2$CFHCF$_3$ (3-F) |
| 226 | C$_3$H$_7$ | cyclohexyl | -CH=CH- | phenyl | -CH=CH- | phenyl | CF$_2$O | phenyl | OCF$_2$CF$_2$H (3-F) |
| 227 | C$_5$H$_{11}$ | phenyl | — | phenyl | — | phenyl (F) | CF$_2$O | phenyl | OCF$_2$CFHCF$_3$ (3,5-diF) |
| 228 | CH=CH- | cyclohexyl | -CH=CH- | phenyl | -CH=CH- | phenyl | CF$_2$O | phenyl | OCF$_2$CF$_2$H (3-F) |

| | | | | | | | |
|---|---|---|---|---|---|---|---|
| 229 | C$_5$H$_{11}$ |  |  | 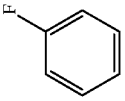 | 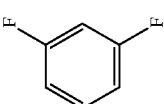 | CF$_2$O | 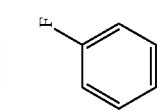 OCF$_2$CFHCF$_3$ |
| 230 | C$_3$H$_7$ |  | — |  | — | CF$_2$O |  F |
| 231 | C$_3$H$_7$ |  | — |  | — | CF$_2$O |  F |
| 232 | C$_3$H$_7$ |  | — |  | — | CF$_2$O |  F |
| 233 | C$_5$H$_{11}$ |  | — |  | — | CF$_2$O |  CF$_3$ |
| 234 | C$_5$H$_{11}$ |  | — |  | — | CF$_2$O |  CF$_3$ |
| 235 | C$_5$H$_{11}$ |  | — |  | — | CF$_2$O |  CF$_3$ |

-continued

| No. | R¹-A¹-Z¹- | -A²-Z²- | -A³-Z³- | -A⁴-Y¹ |
|---|---|---|---|---|
| 236 | C₅H₁₁ — Cy — | Cy — | Cy — $CF_2O$ | Ph — $OCF_3$ |
| 237 | C₃H₇ — Cy — | Cy — | Cy — $CF_2O$ | Ph(F) — $OCF_3$ |
| 238 | C₃H₇ — Cy — | Cy — | Cy — $CF_2O$ | Ph(F,F) — $OCF_3$ |
| 239 | C₃H₇ — Cy — | Cy — | Cy — $CF_2O$ | Ph(F,F) — $OCF_2H$ |
| 240 | C₃H₇ — Cy — | Cy — | Cy — $CF_2O$ | Ph(F,F) — CN |

-continued

| | | |
|---|---|---|
| 241 | ![structure](propyl-cyclohexene-CF2O-phenyl-F) | |
| 242 | | |
| 243 | | |
| 244 | | |
| 245 | | |
| 246 | | |
| 247 | | |

-continued
| | | |
|---|---|---|
| 248 | 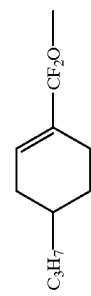 | 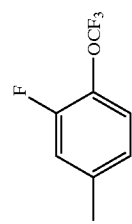 |
| 249 | 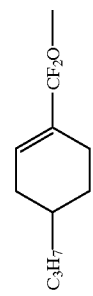 | 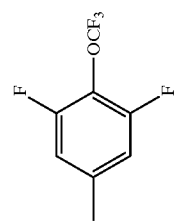 |
| 250 | 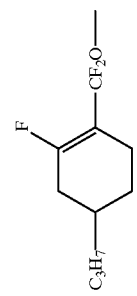 | 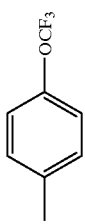 |
| 251 | 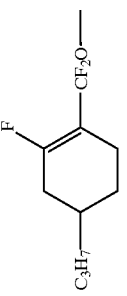 | 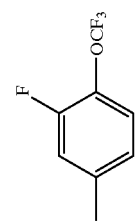 |
| 252 | 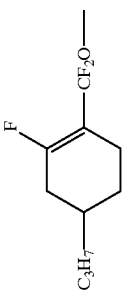 | 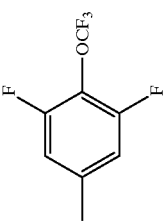 |
| 253 | 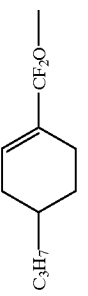 | 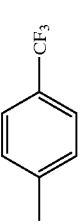 |
| 254 | 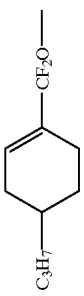 | 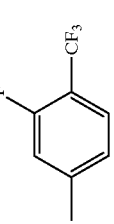 |

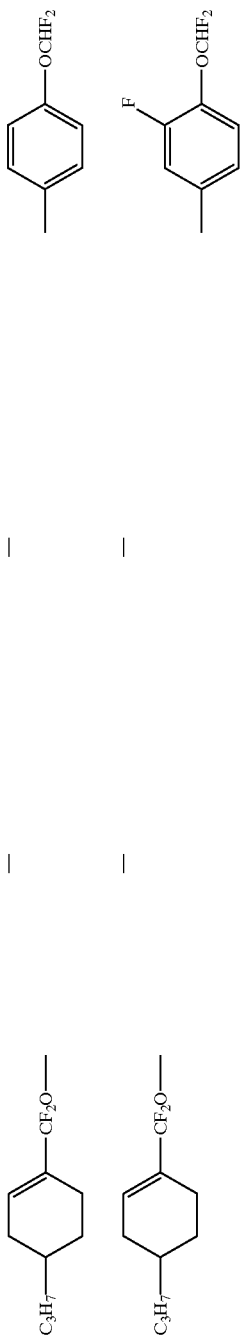

-continued

| No. | Structure 1 | Structure 2 |
|---|---|---|
| 261 | 4-propyl-1-(OCF$_2$-) cyclohexene | 4-methylphenyl-OCHF$_2$ (3,5-difluoro) |
| 262 | 4-propyl-2-fluoro-1-(OCF$_2$-) cyclohexene | 4-methylphenyl-OCHF$_2$ |
| 263 | 4-propyl-2-fluoro-1-(OCF$_2$-) cyclohexene | 4-methylphenyl-OCHF$_2$ (2-fluoro) |
| 264 | 4-propyl-2-fluoro-1-(OCF$_2$-) cyclohexene | 4-methylphenyl-OCHF$_2$ (2,6-difluoro) |
| 265 | 4-propyl-1-(OCF$_2$-) cyclohexene | 4-methylphenyl-OCF$_2$CFHCF$_3$ |
| 266 | 4-propyl-1-(OCF$_2$-) cyclohexene | 4-methylphenyl-OCF$_2$CFHCF$_3$ (2-fluoro) |

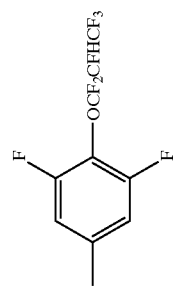
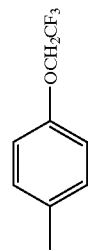
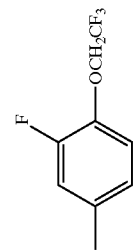
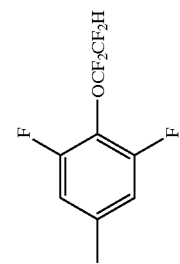
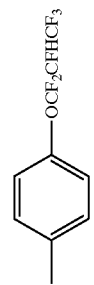
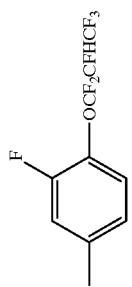
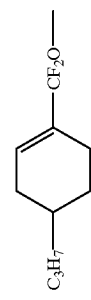
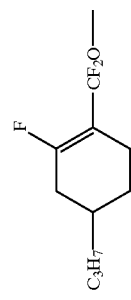
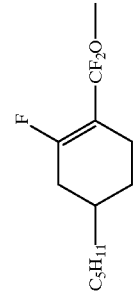
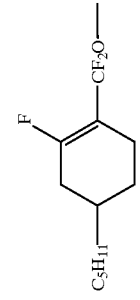
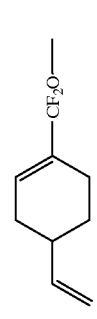
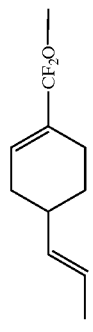

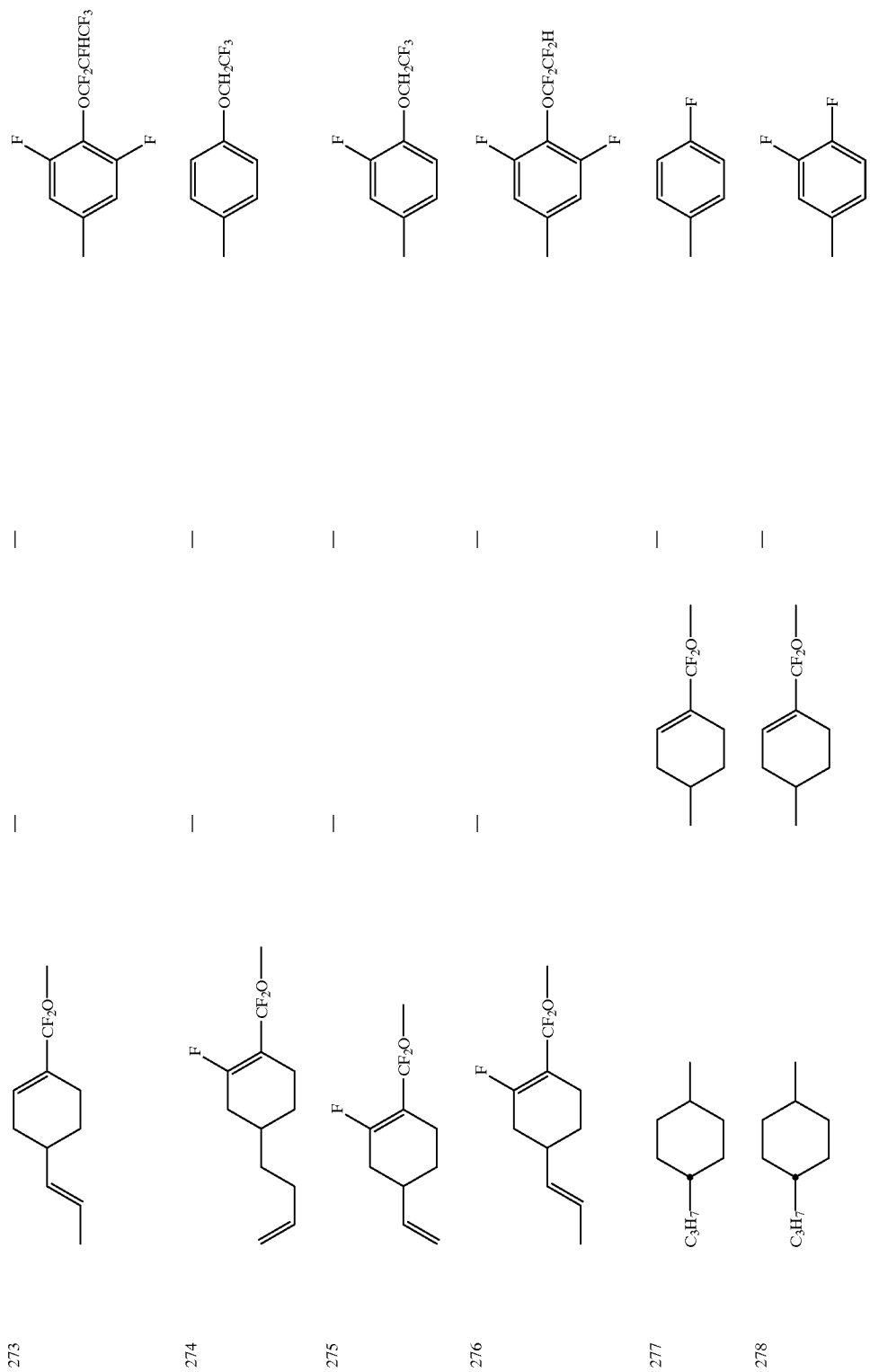

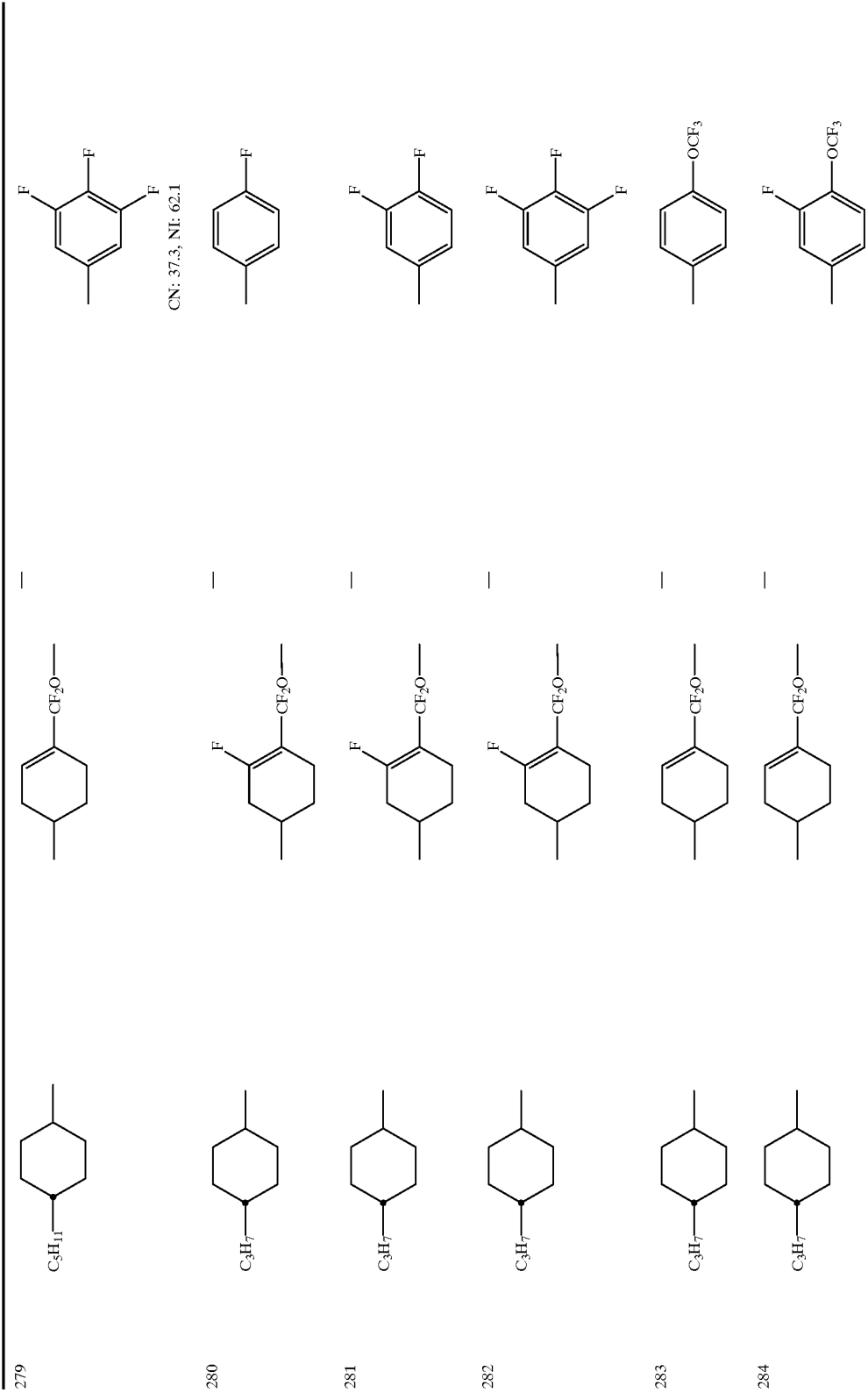

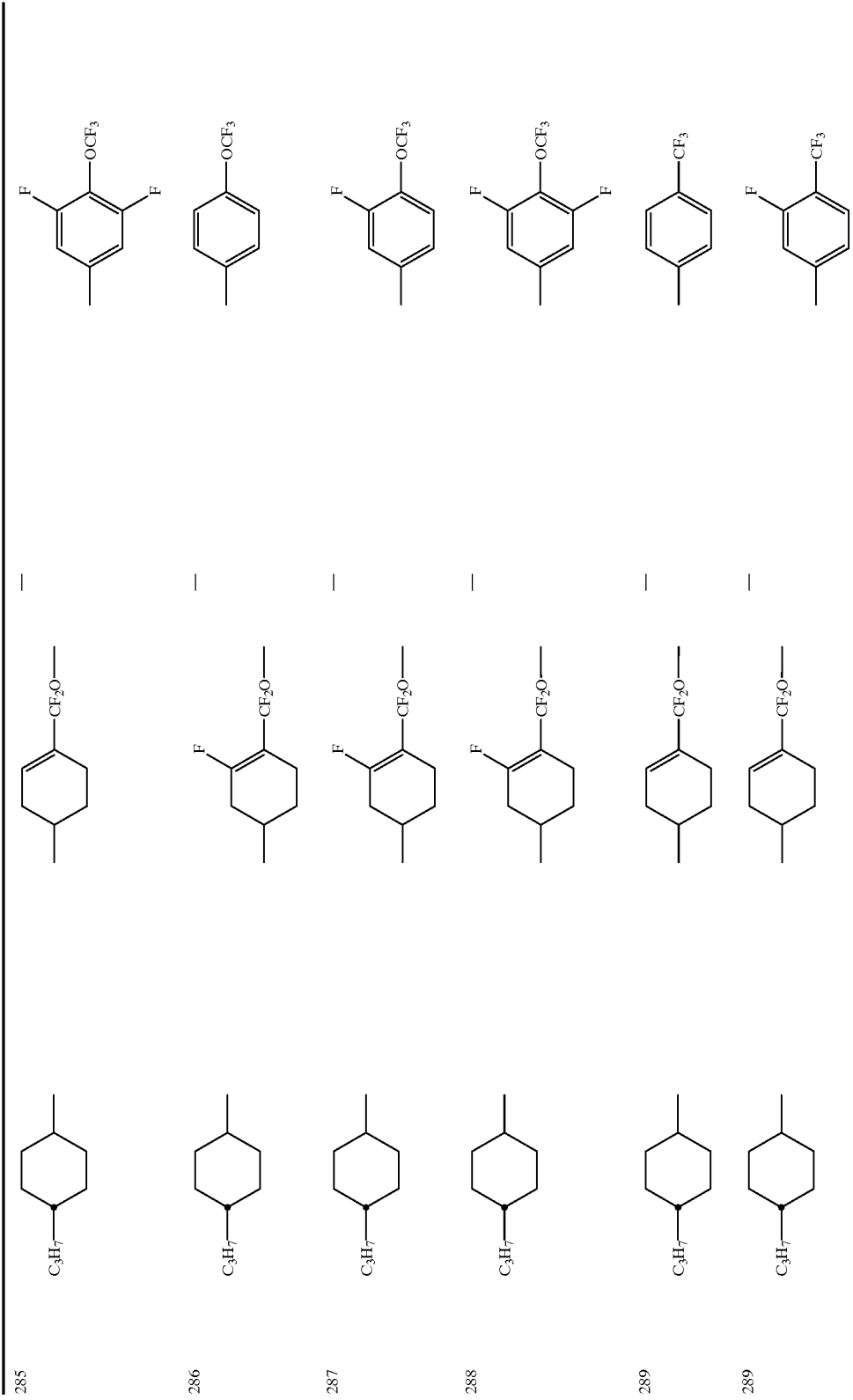

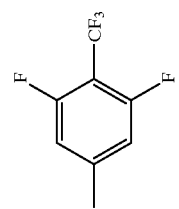
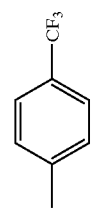
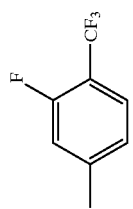
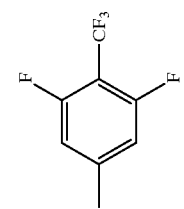
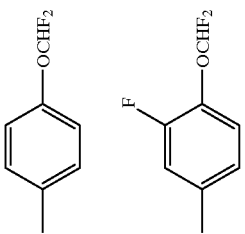
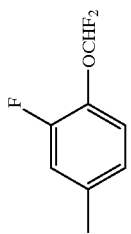
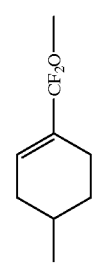
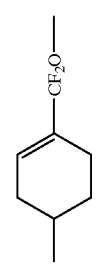
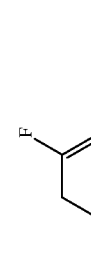
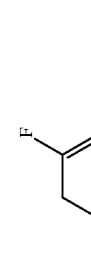
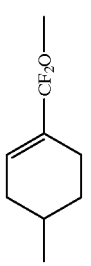
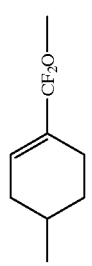
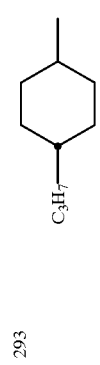
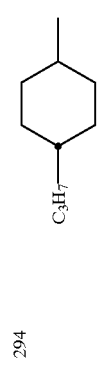
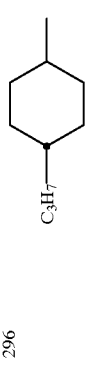

| | | |
|---|---|---|
| 297 | 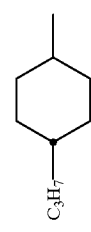 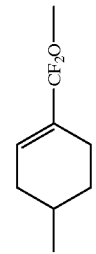 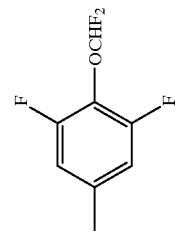 | |
| 298 | 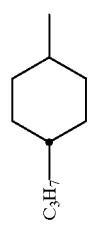 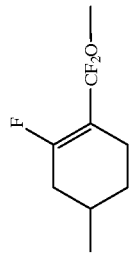 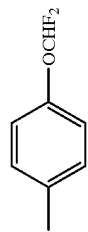 | |
| 299 | 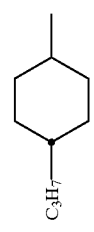 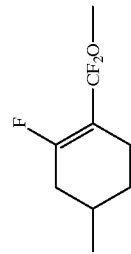 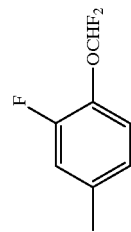 | |
| 300 | 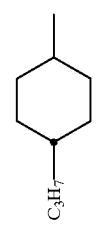 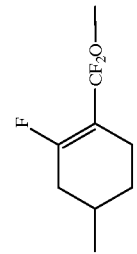 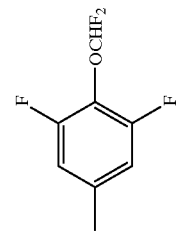 | |
| 301 | 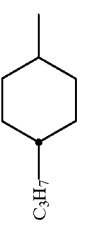 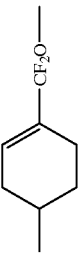 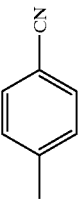 | |
| 302 | 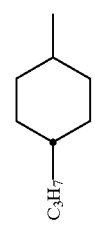 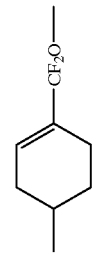 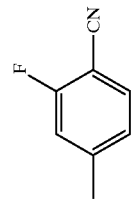 | |

-continued
| | | |
|---|---|---|
| 303 | 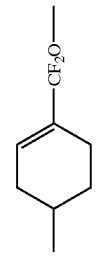 | 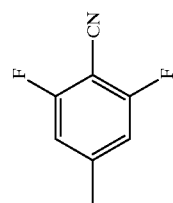 |
| 304 | 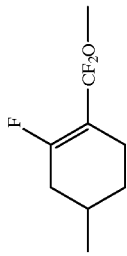 | 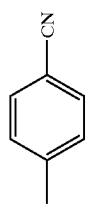 |
| 305 | 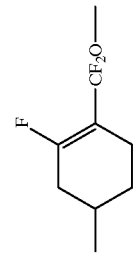 | 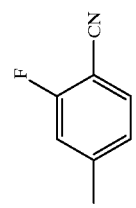 |
| 306 | 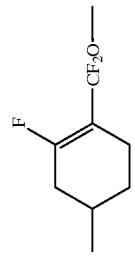 | 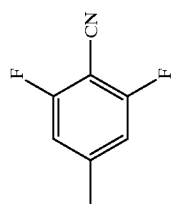 |
| 307 | 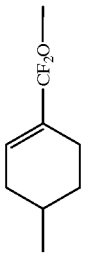 | 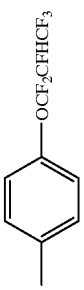 |
| 308 | 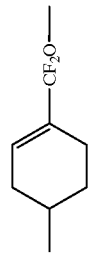 | 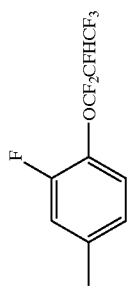 |

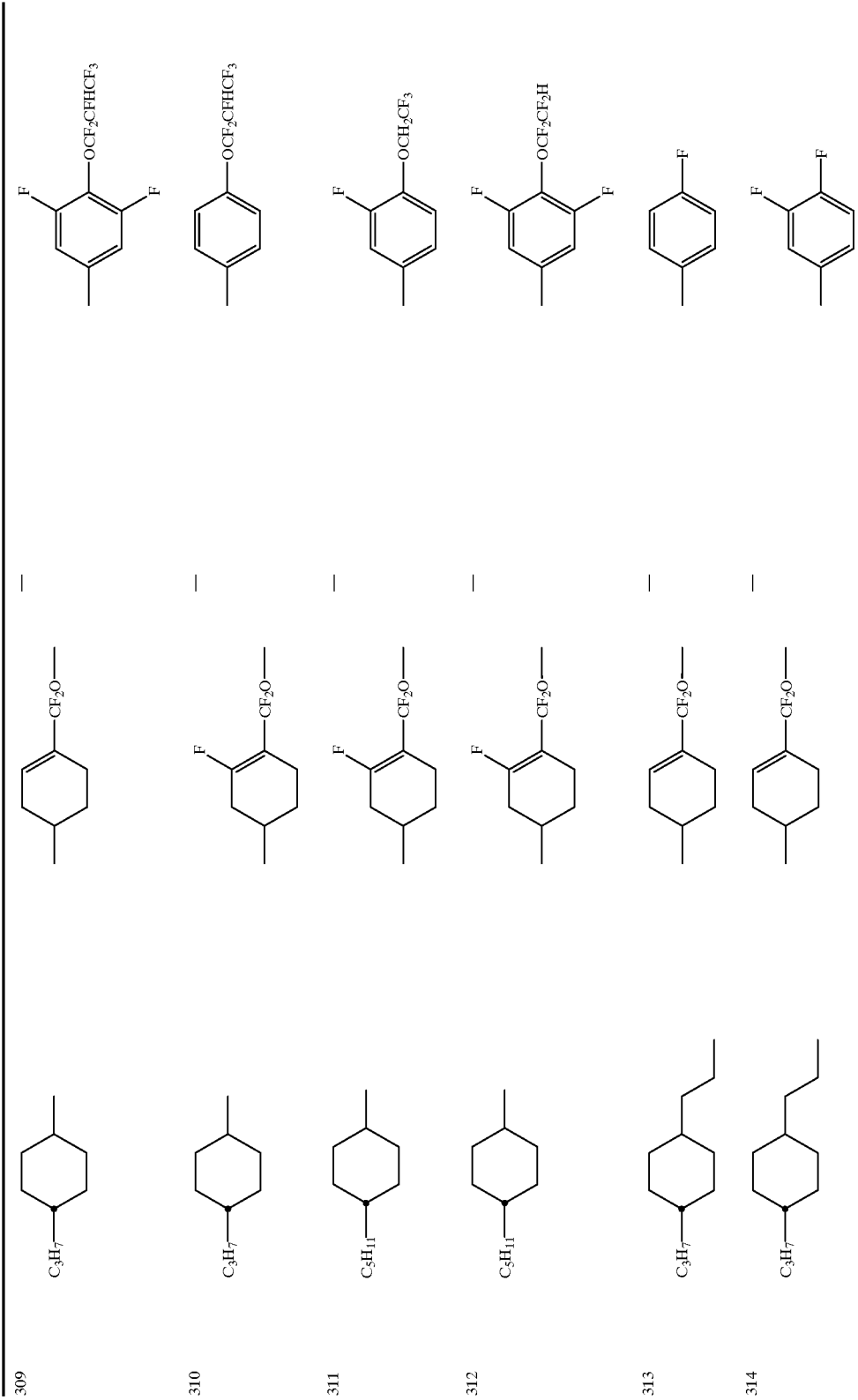

-continued
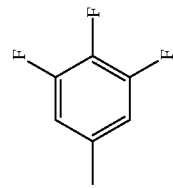 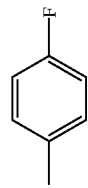 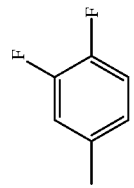 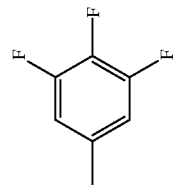 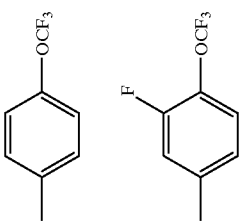
315
316
317
318
319
320

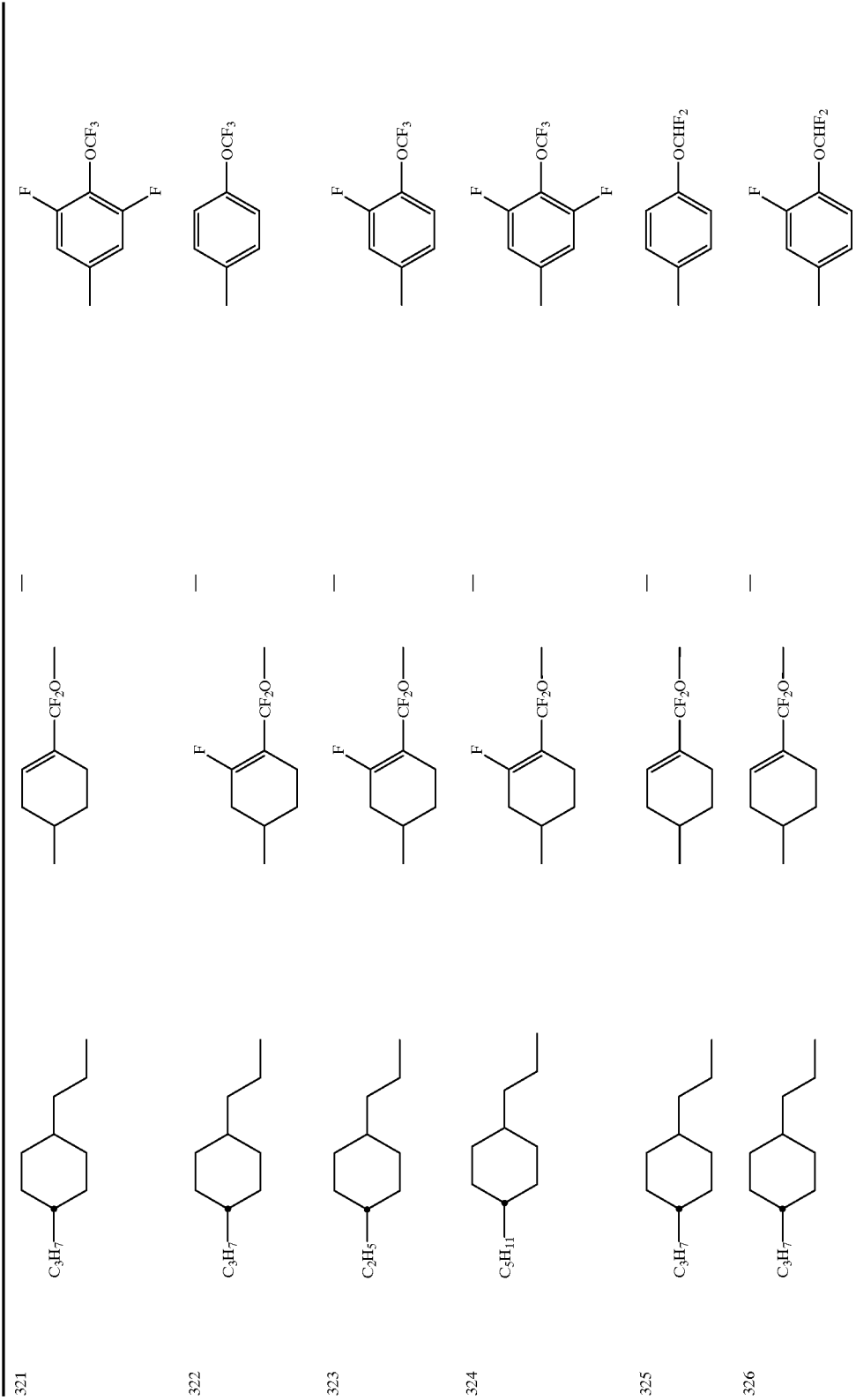

| | | |
|---|---|---|
| 327 | 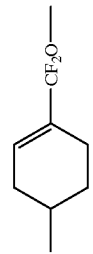—CF$_2$O— | 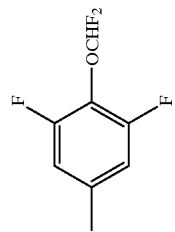 |
| 328 | 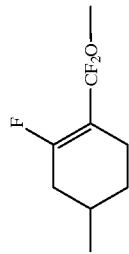—CF$_2$O— | 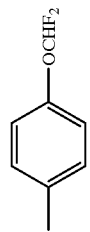 |
| 329 | 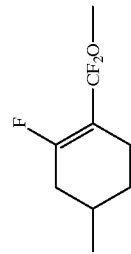—CF$_2$O— | 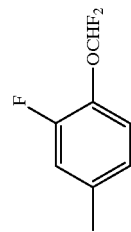 |
| 330 | 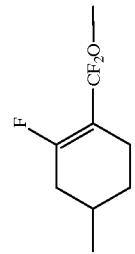—CF$_2$O— | 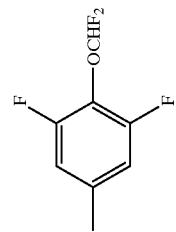 |
| 331 | 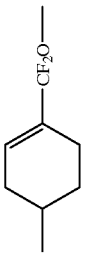—CF$_2$O— | 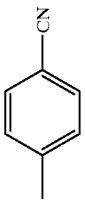 |
| 332 | 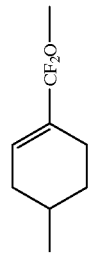—CF$_2$O— | 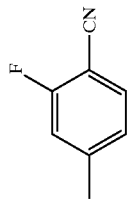 |

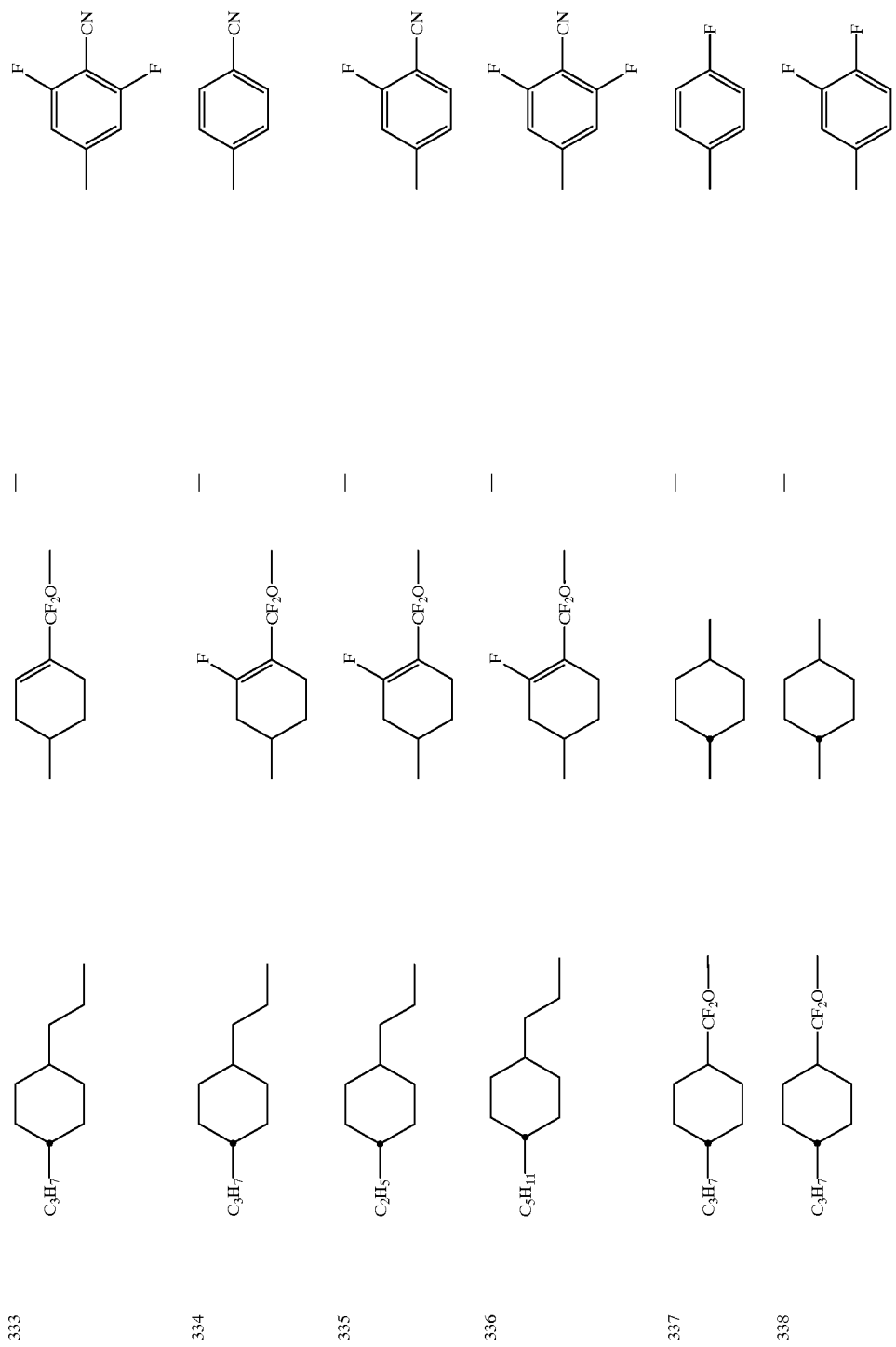

-continued
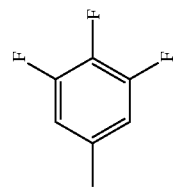
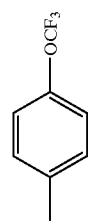
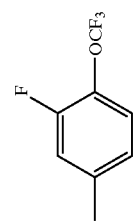
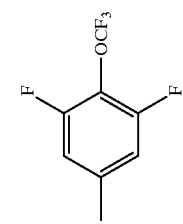
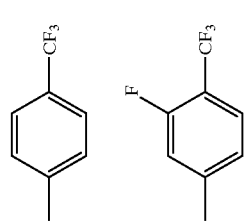
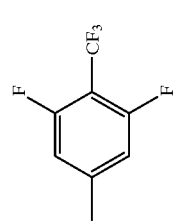
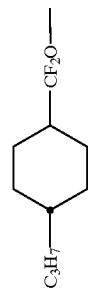
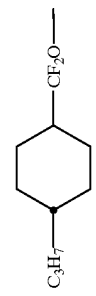
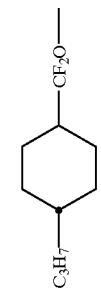
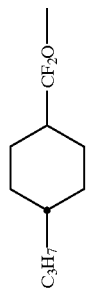
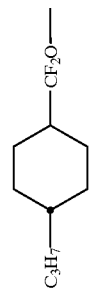
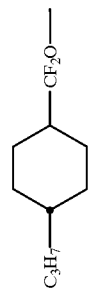
339
340
341
342
343
344
345

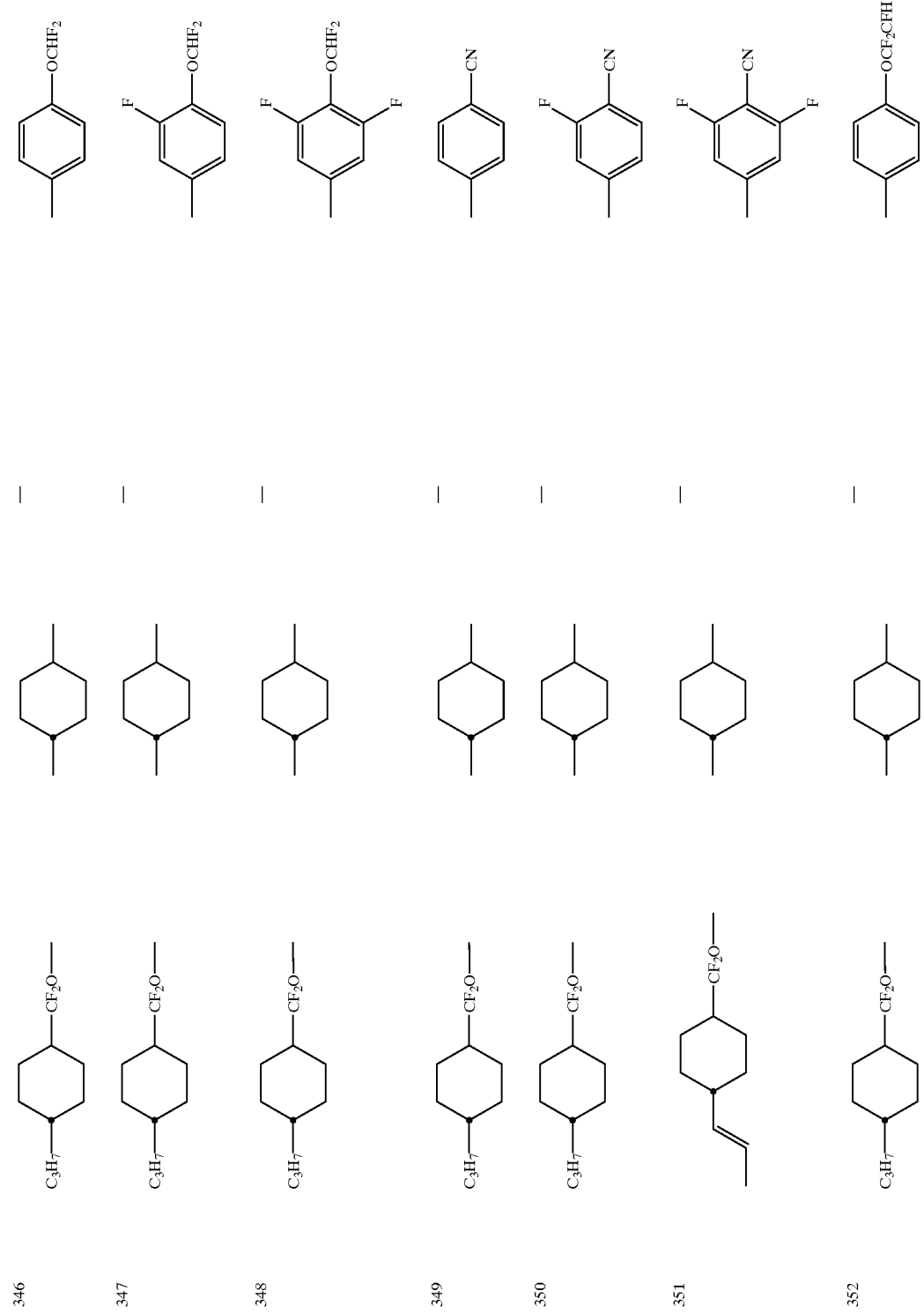

-continued

| No. | | | |
|---|---|---|---|
| 353 | C₃H₇-Cy-CF₂O- | -Cy- | -Ph(2-F)-OCF₂CFHCF₃ |
| 354 | C₃H₇-Cy-CF₂O- | -Cy- | -Ph(2,6-F₂)-OCF₂CFHCF₃ |
| 355 | C₃H₇-Cy-CF₂O- | -Cy- | -Ph-OCF₂CFHCF₃ |
| 356 | C₃H₇-Cy-CF₂O- | -Cy- | -Ph(2-F)-OCF₂CFHCF₃ |
| 357 | C₃H₇-Cy-CF₂O- | -Cy- | -Ph(2,6-F₂)-OCF₂CFHCF₃ |
| 358 | C₃H₇-Cy-CF₂O- | -Cy- | -Ph-OCH₂CF₃ |
| 359 | C₃H₇-Cy-CF₂O- | -Cy- | -Ph(2-F)-OCH₂CF₃ |

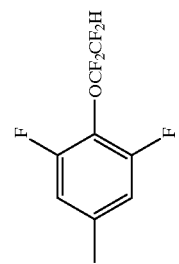
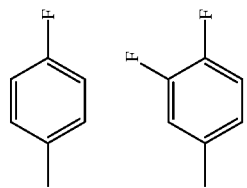
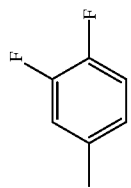
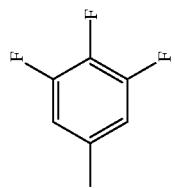
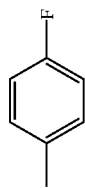
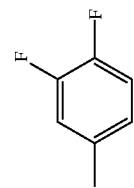
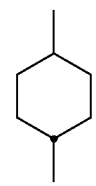
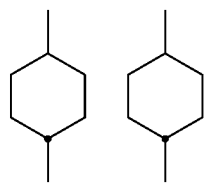
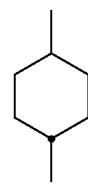
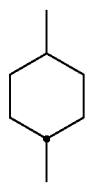
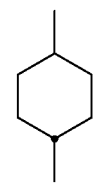

-continued

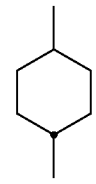 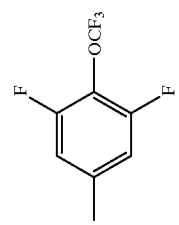 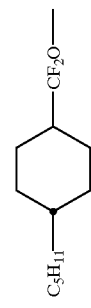
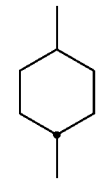 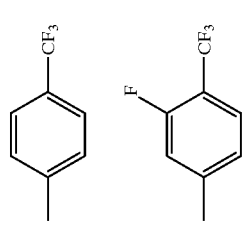 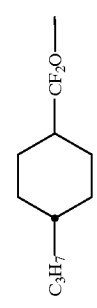
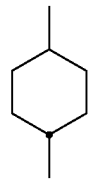 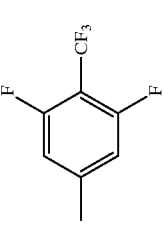 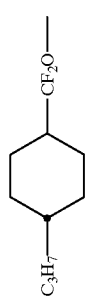
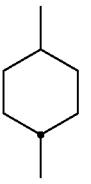 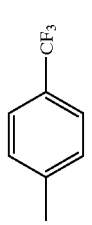 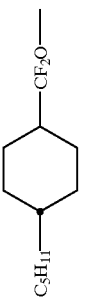
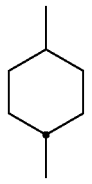 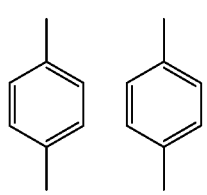 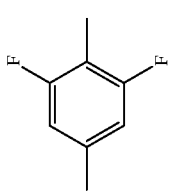 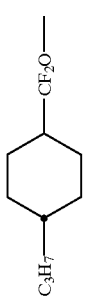
 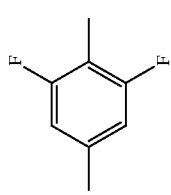 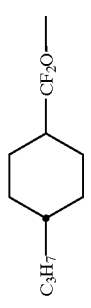

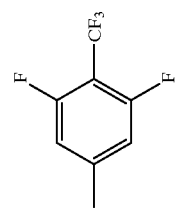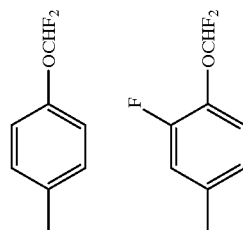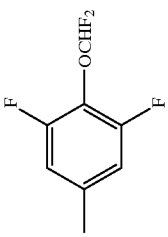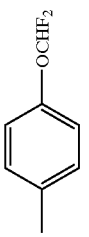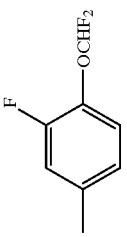
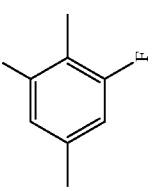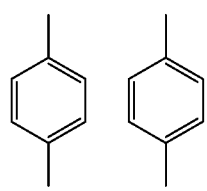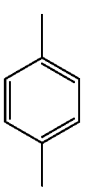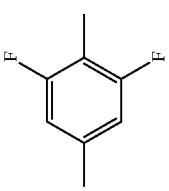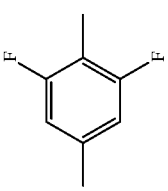
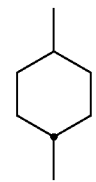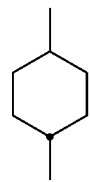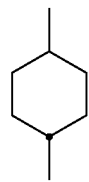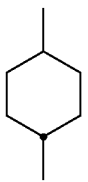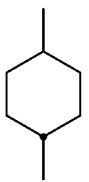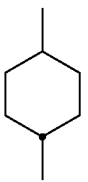
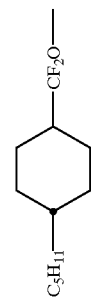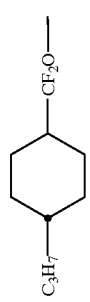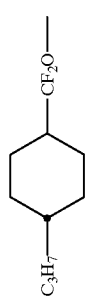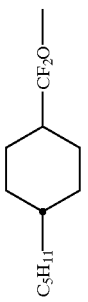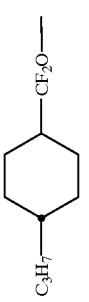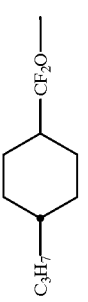

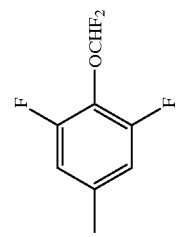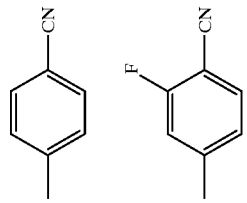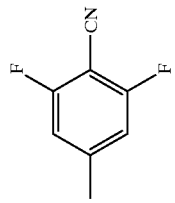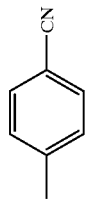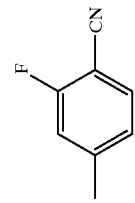
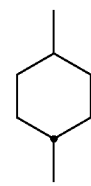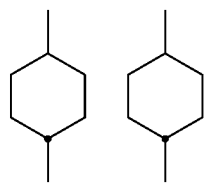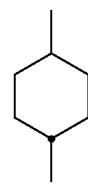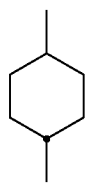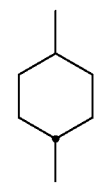
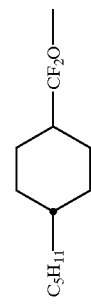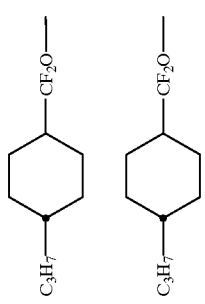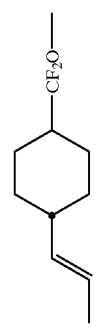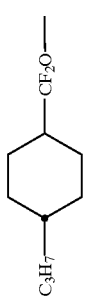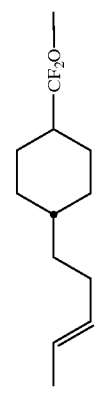

-continued
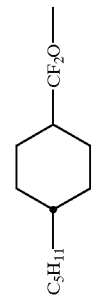
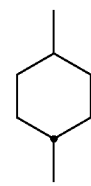
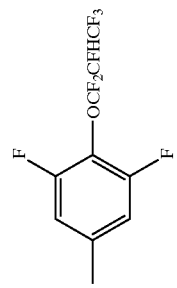
396
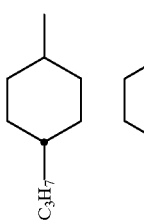
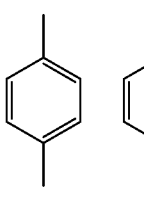
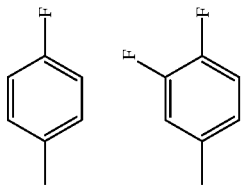
397
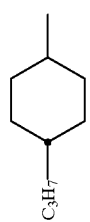
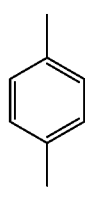
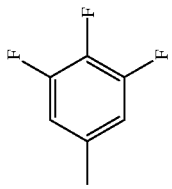
398
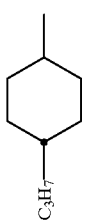
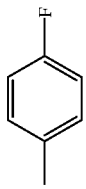
399
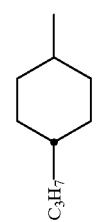
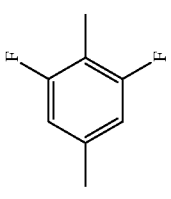
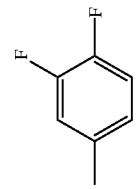
400
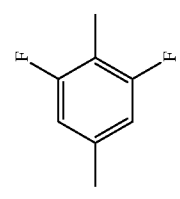
401

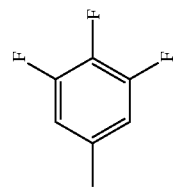
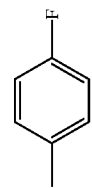
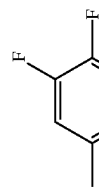
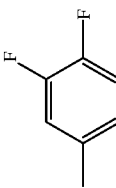
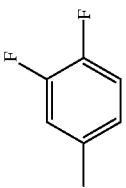
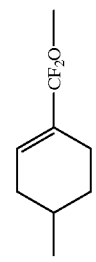
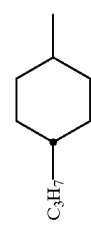
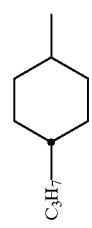
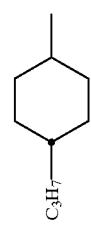
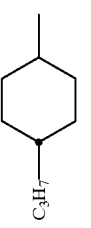
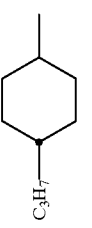
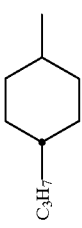

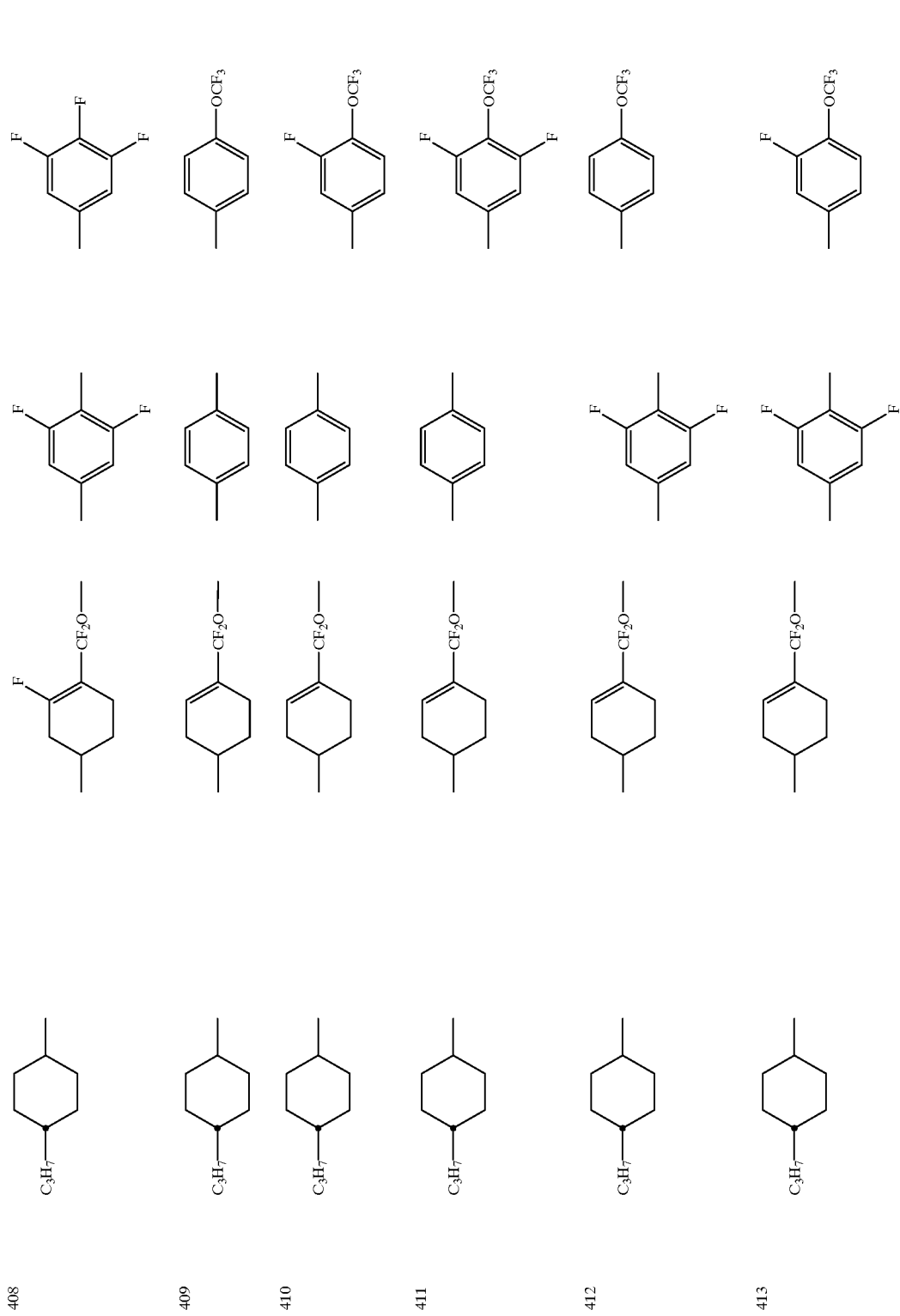

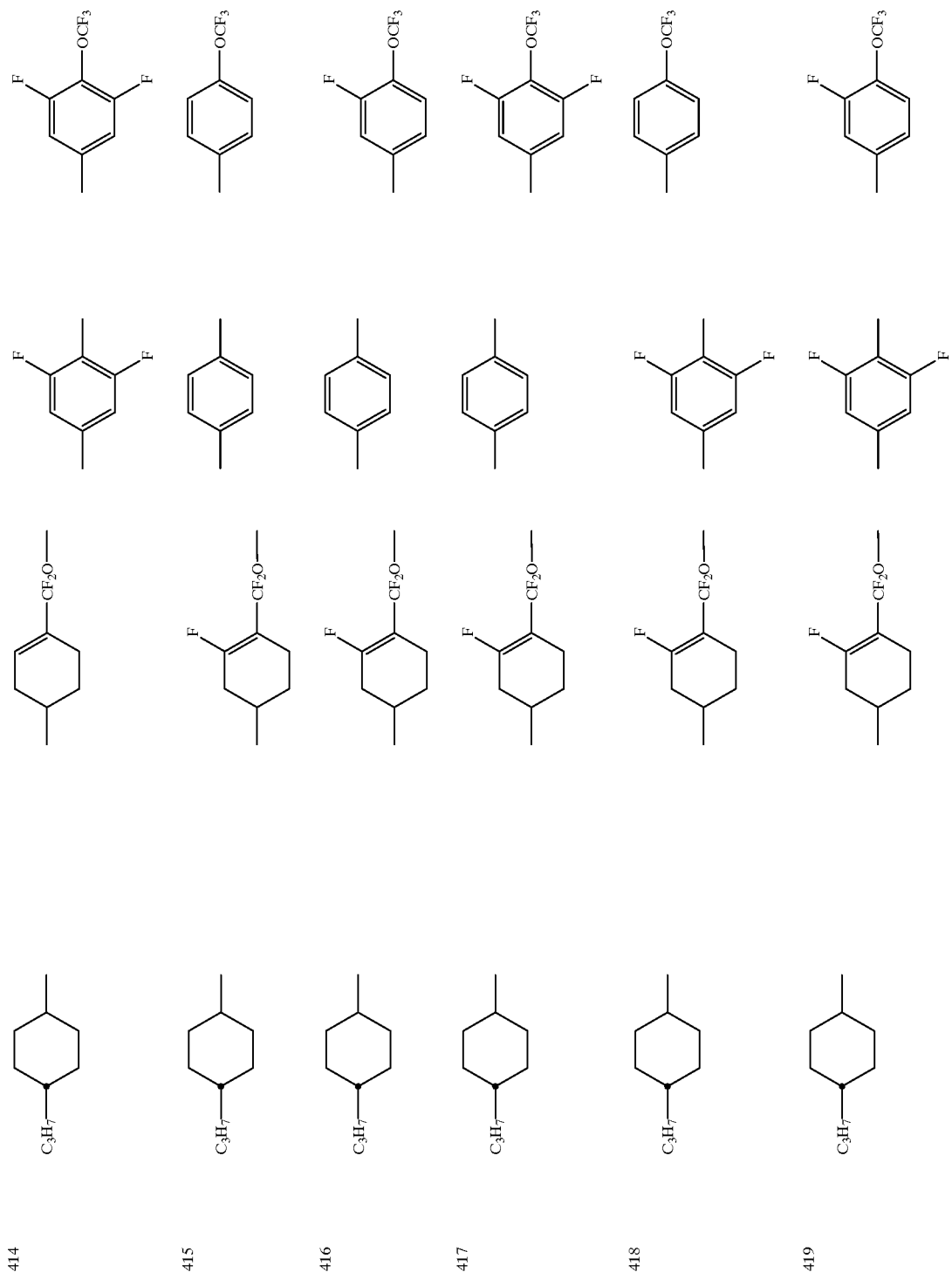

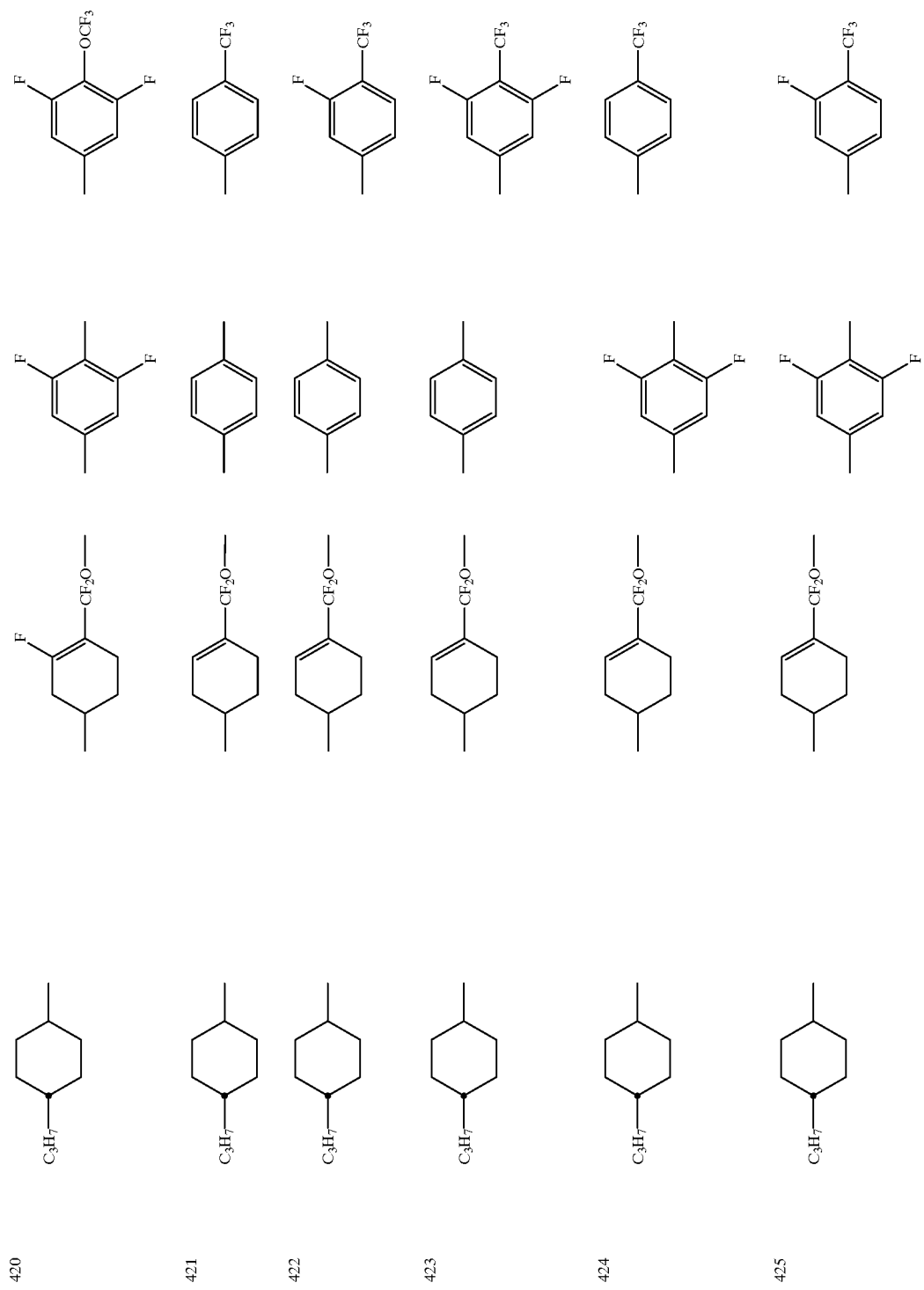

-continued
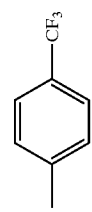
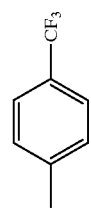
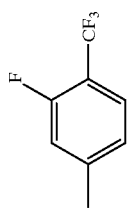
426
427
428
429
430
431

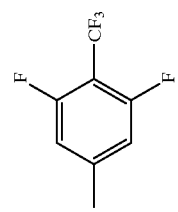
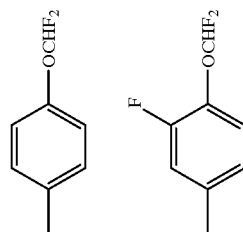
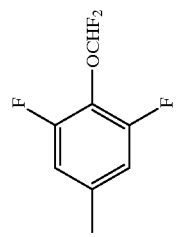
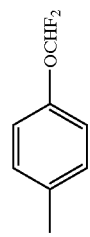
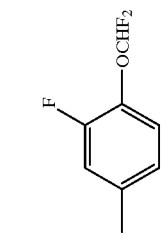
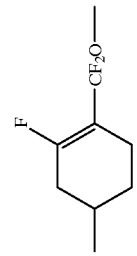
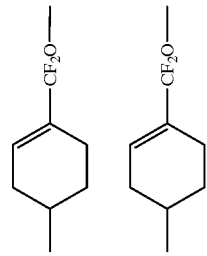
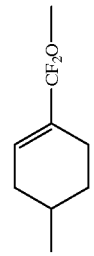
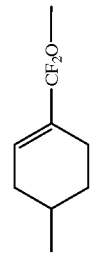
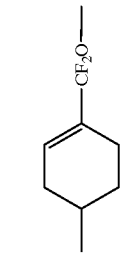

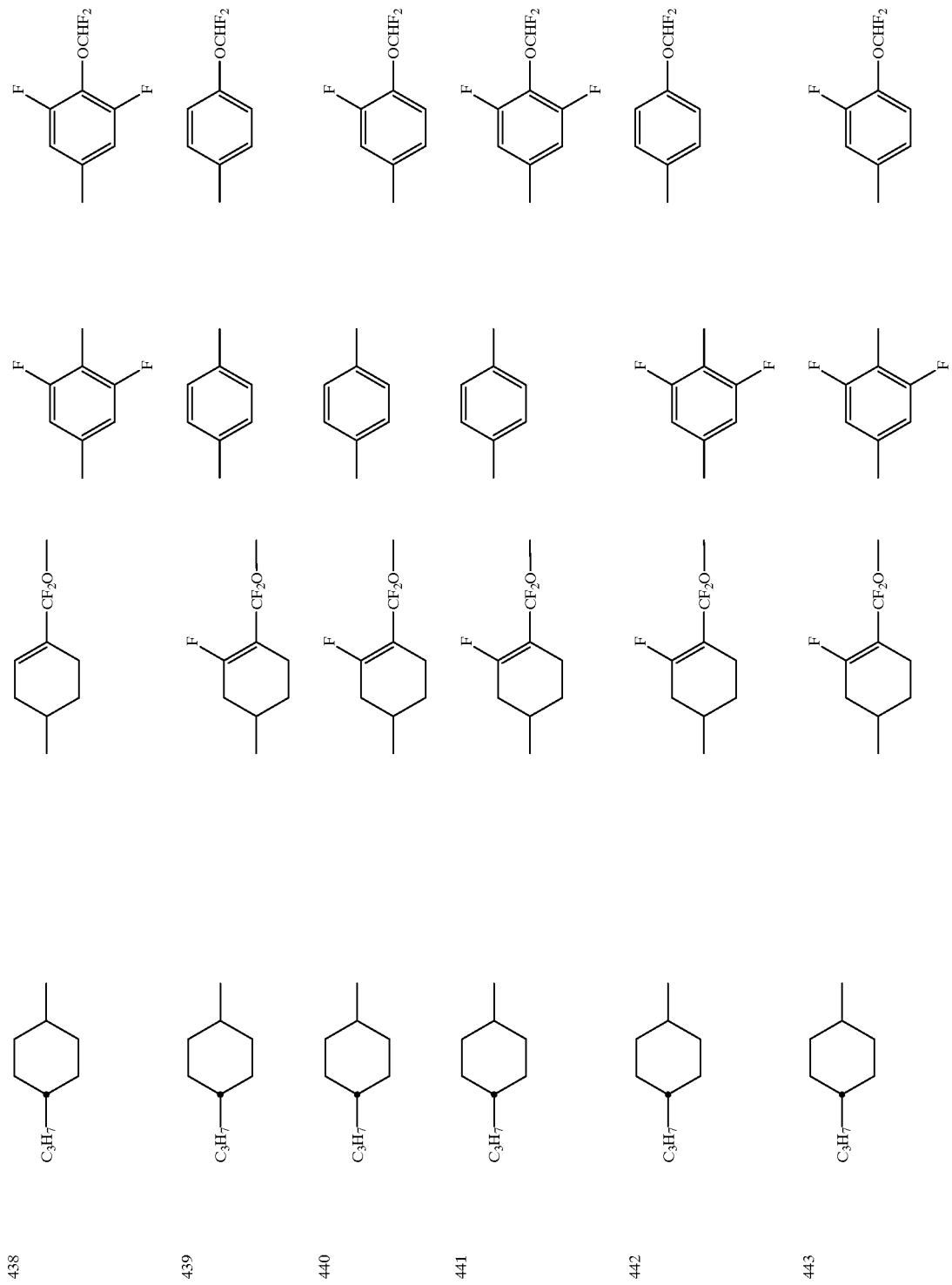

-continued
| | | | | |
|---|---|---|---|---|
|444|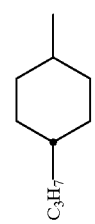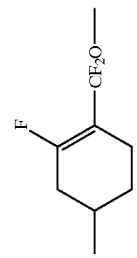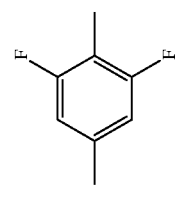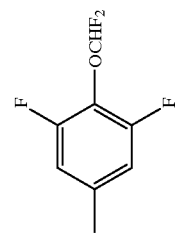|
|445|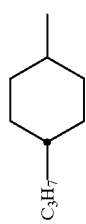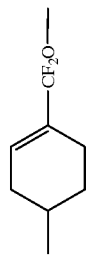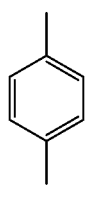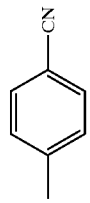|
|446|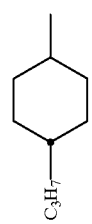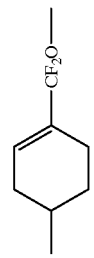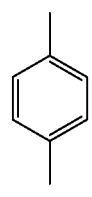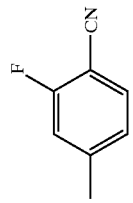|
|447|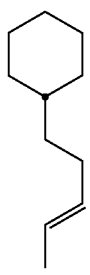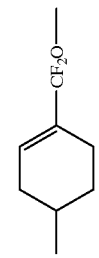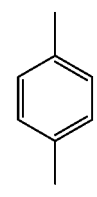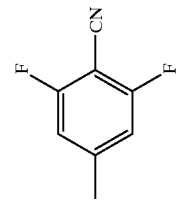|
|448|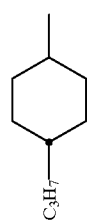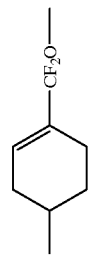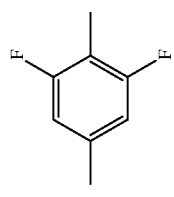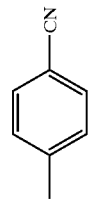|
|449|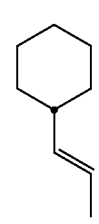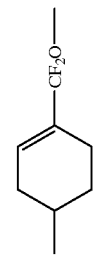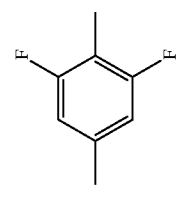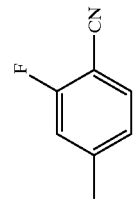|

-continued
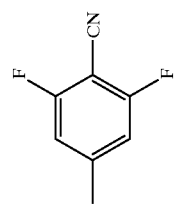 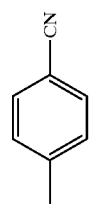 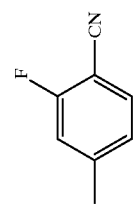 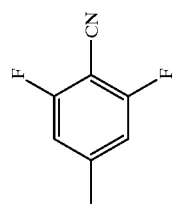 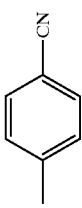 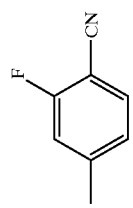
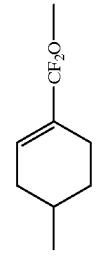 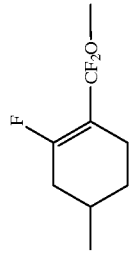 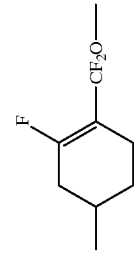 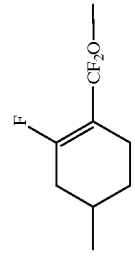 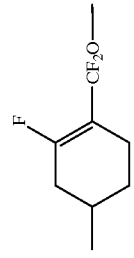
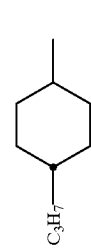 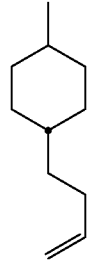 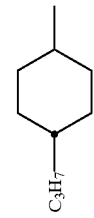 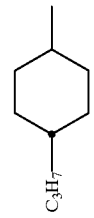 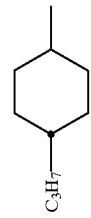
450
451
452
453
454
455

-continued

| | | | | |
|---|---|---|---|---|
| 456 | | | | |
| 457 | | | | |
| 458 | | | | |
| 459 | | | | |
| 460 | | | | |
| 461 | | | | |

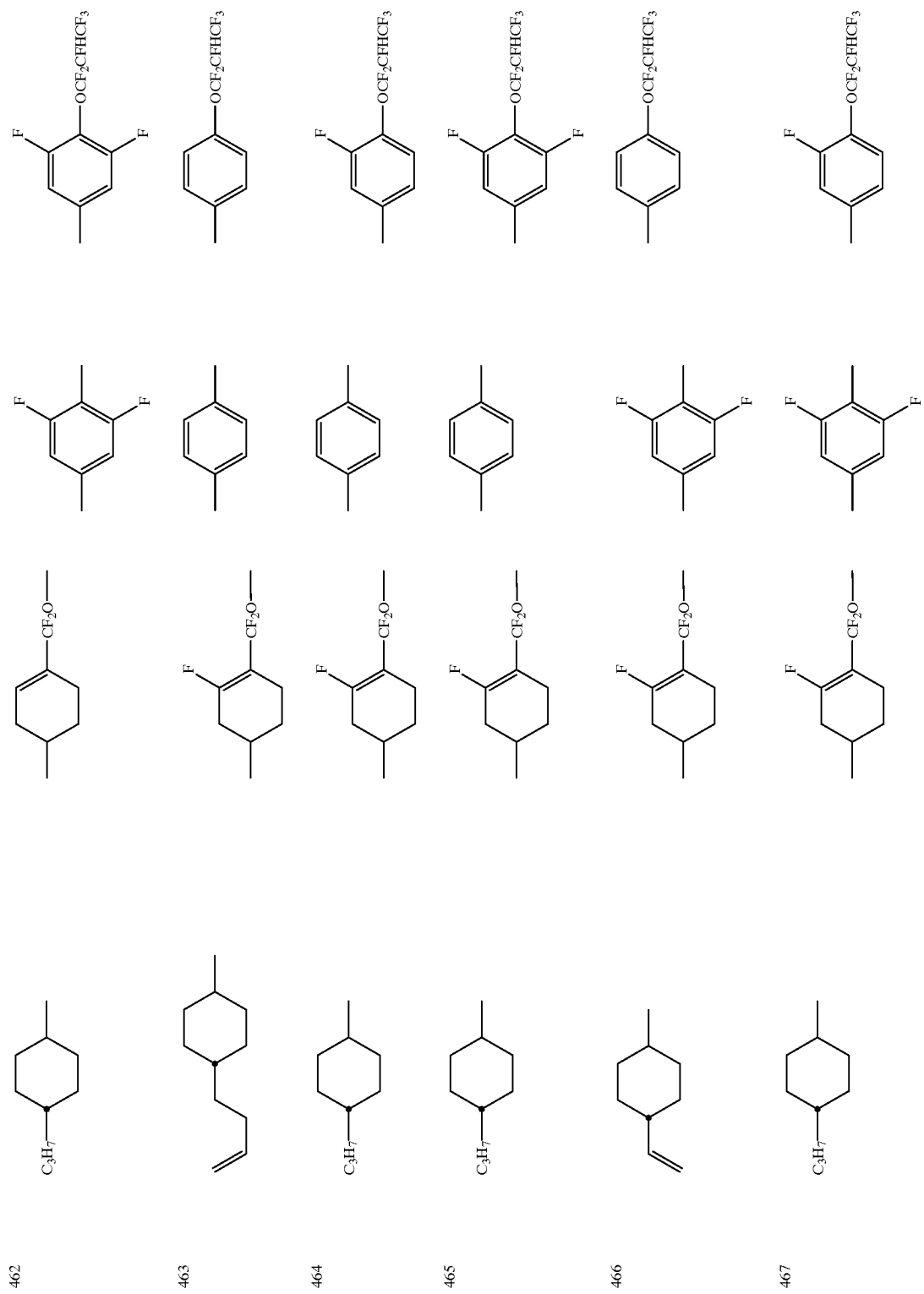

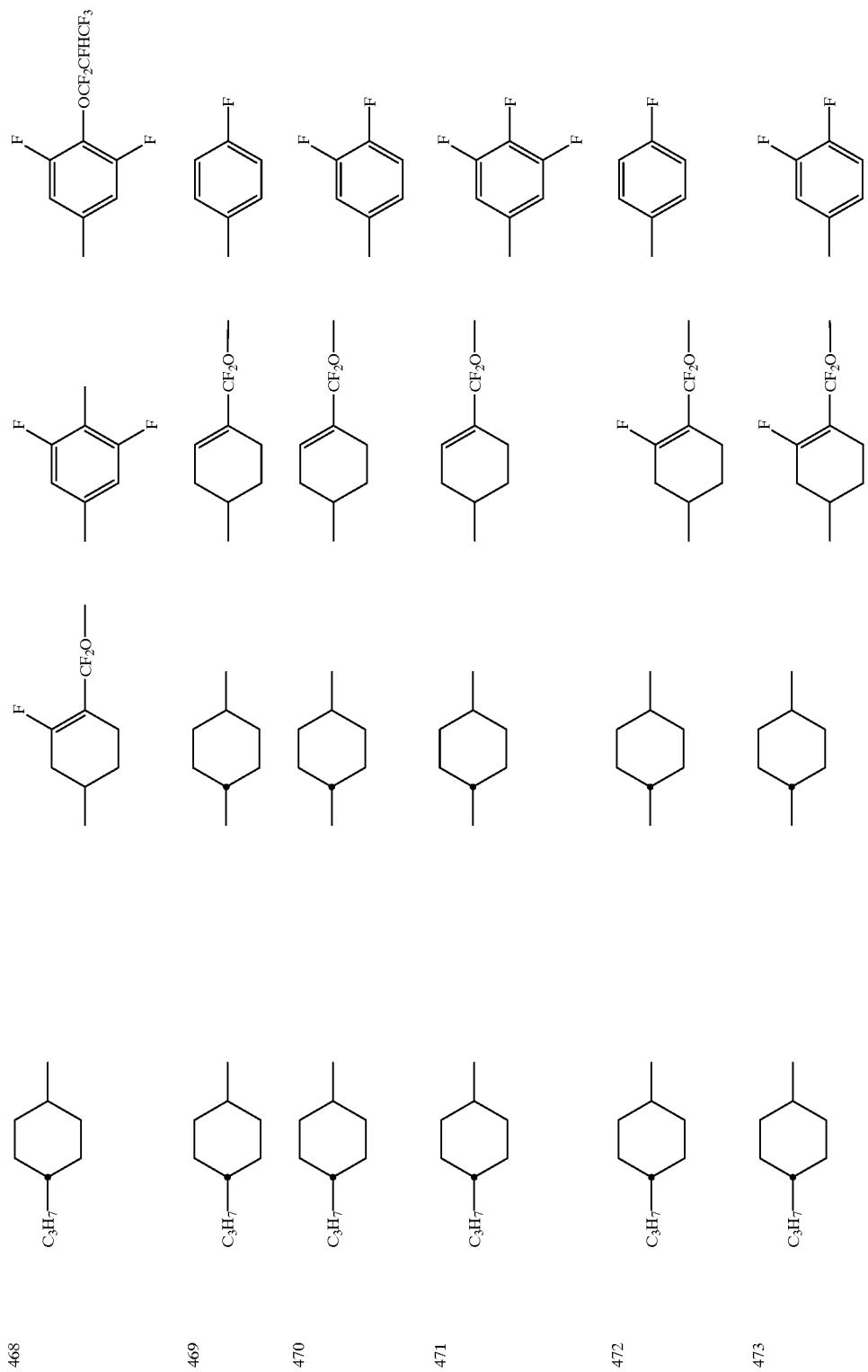

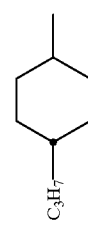 474 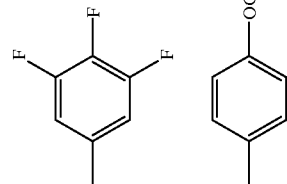
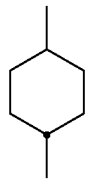 475 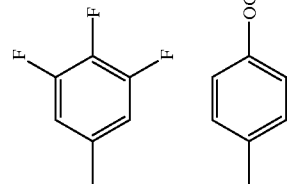
476 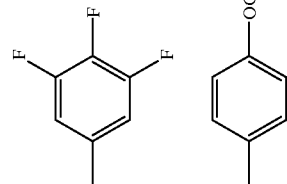
477 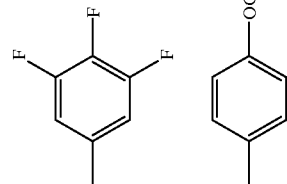
478
479

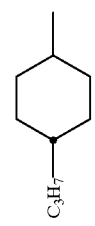 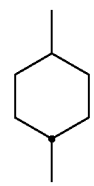 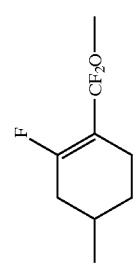 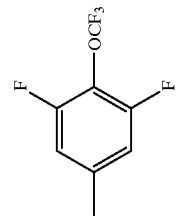
480
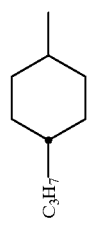 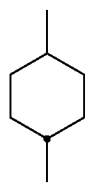 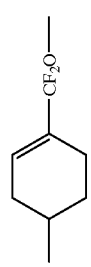 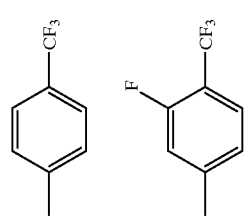
481
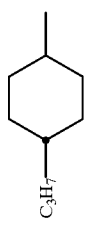 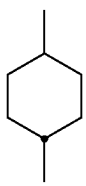 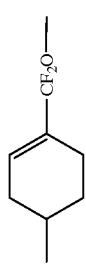 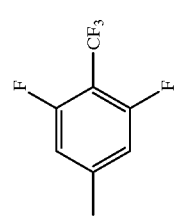
482
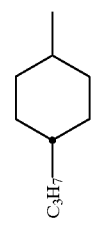 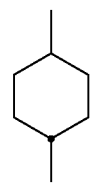 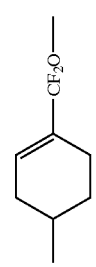 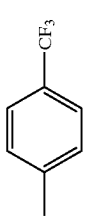
483
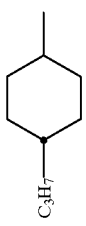 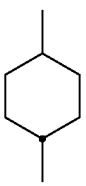 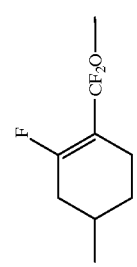 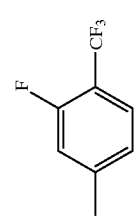
484
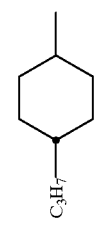 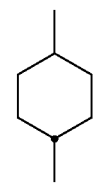 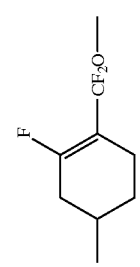 
485

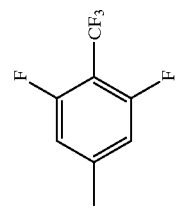
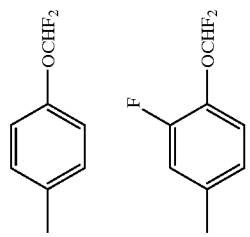
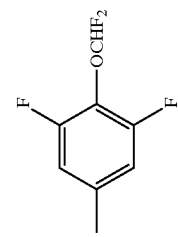
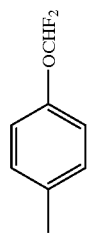
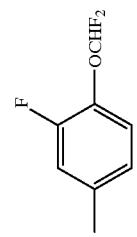
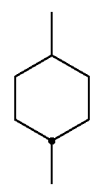
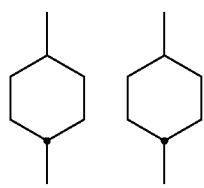
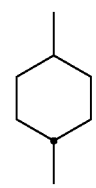
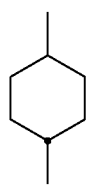
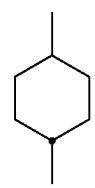
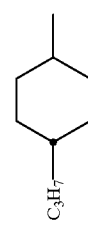
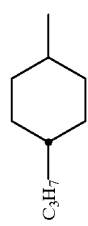
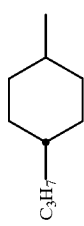
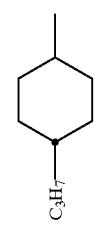
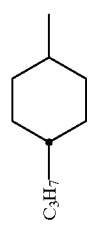
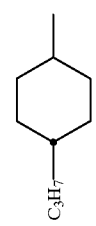

-continued

| | | | | |
|---|---|---|---|---|
| 492 | Cy-C3H7 | Cy | Cy-CF2O- | Ph(2,6-F)-OCHF2 |
| 493 | Cy-C3H7 | Cy | Cy-CF2O- | Ph-CN |
| 494 | Cy-CH2CH2CH=CH- | Cy | Cy-CF2O- | Ph(2-F)-CN |
| 495 | Cy-C3H7 | Cy | Cy-CF2O- | Ph(2,6-F)-CN |
| 496 | Cy-C3H7 | Cy | Cy(2-F)-CF2O- | Ph-CN |
| 497 | Cy-C3H7 | Cy | Cy(2-F)-CF2O- | Ph(2-F)-CN |

| | | | | |
|---|---|---|---|---|
| 498 | 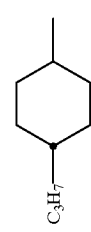 | 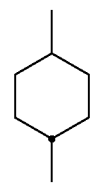 | | 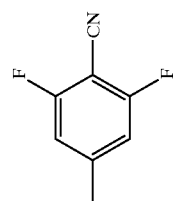 |
| 499 | 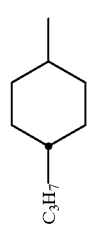 | 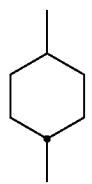 | | 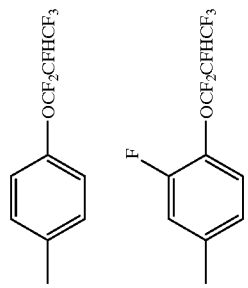 |
| 500 | 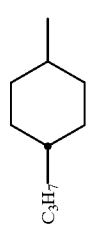 | 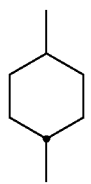 | | 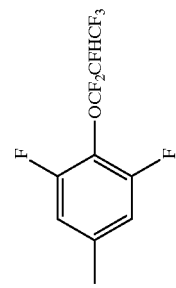 |
| 501 | 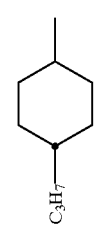 | 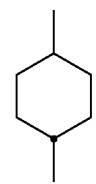 | | 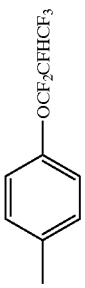 |
| 502 | 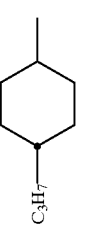 | 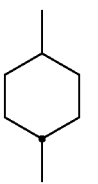 | | 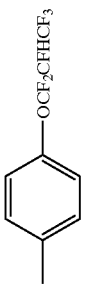 |

| | | | |
|---|---|---|---|
| 503 | 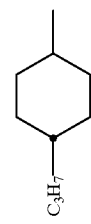 | 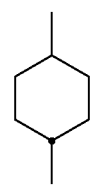 | 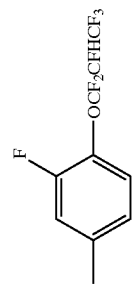 |
| 504 | 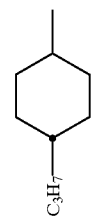 | 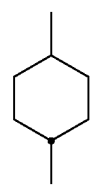 | 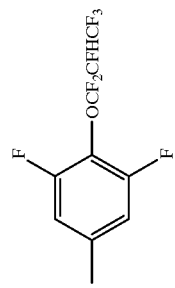 |

USE EXAMPLES

The compounds in use examples are shown by abbreviations according to definitions shown in Table 1. Threshold voltage Vth, refractive anisotropic value $\Delta n$ and dielectric anisotropic value $\Delta \epsilon$ were determined at 25° C. by sealing into TN cell (twist nematic cell) with cell thickness of 9.2 μm, and viscosity η was determined at 20° C.

Example 8 (Use Example 1)

Clear point (Cp) of a liquid crystal composition consisting of 24% (by weight, hereinafter referred to the same) of 4-(trans-4-propylcyclohexyl)benzonitrile, 36% of 4-(trans-4-pentylcyclohexyl)benzonitrile, 25% of 4-(trans-4-heptylcyclohexyl)benzonitrile, and 15% of 4-(4-propylphenyl)benzonitrile was 71.7° C. As to the liquid crystal composition sealed into TN cell, $\Delta \epsilon$ was 11.0, $\Delta n$ was 0.137, η was 26.7 mPa.s, and Vth was 1.78V.

85% by weight of the liquid crystal composition considered to be mother liquid crystals (hereinafter abbreviated as mother liquid crystals A) was mixed with 15% by weight of 3-fluoro-4-(1,1,2,2-tetrafluoroethoxy)phenyl=4-(trans-4-propylcyclohexyl)benzoate (compound number 10) and then values of physical properties were determined. From the results, the said compound had Cp: 122.4° C., $\Delta \epsilon$: 13.0, $\Delta n$: 0.137, η: 75.0, and Vth: 1.65V as extrapolative values. Further, after the said liquid crystal composition was allowed to stand for 20 days in a freezer at -20° C., precipitation of crysals or expression of a smectic phase has not been found.

Example 9 (Use Example 2)

90% by weight of mother liquid crystals A shown in Example 4 was mixed with 10% by weight of 3-fluoro-4-(1,1,2,2-tetrafluoroethoxy)phenyl=2,6-difluoro-4-(trans-4-pentylcyclohexyl)benzoate (compound number 16) shown in Example 1 and then values of physical properties were determined. From the results, the said compound had Cp: 82.4° C., $\Delta \epsilon$: 14.3, $\Delta n$: 0.117, η: 67.3, and Vth: 1.62V as extrapolative values.

Example 10 (Use Example 3)

85% by weight of mother liquid crystals A shown in Example 4 was mixed with 15% by weight of 3-fluoro-4-(1,1,2,2-tetrafluoroethoxy)phenyloxy (4-trans-4-propylcyclohexyl)phenyl)difuluolomethane (compound number 110) shown in Example 2 and then values of physical properties were determined. From the results, the said compound had Cp: 53.7, $\Delta \epsilon$: 7.7, $\Delta n$: 0.097, η: 36.8, and Vth: 1.60V as extrapolative values.

Example 11 (Use Example 4)

85% by weight of mother liquid crystals A shown in Example 4 was mixed with 15% by weight of 3,4,5-trifluorophenyloxy-(trans-(4-(trans-4-propylcyclohexyl)cyclohexyl)difuluolomethane (compound number 123) and then values of physical properties were determined. From the results, the said compound had Cp: 85.0, $\Delta \epsilon$: 15.0, $\Delta n$: 0.077and Vth: 1.71V as extrapolative values.

Example 12 (Use Example 5)

85% by weight of mother liquid crystals A shown in Example 8 was mixed with 15% by weight of 3,4,5trifluorophenyloxy-(trans-(4-(trans-4-pentylcyclohexyl)cyclohexyl)difuluolomethane (compound number 124) and then values of physical properties were determined. From the results, the said compound had Cp: 91.0, $\Delta \epsilon$: 13.67, $\Delta n$: 0.077, η: 31.9, and Vth: 1.73V as extrapolative values.

Example 13 (Use Example 6)

85% by weight of mother liquid crystals A shown in Example 8 was mixed with 15% by weight of 3,4,5trifluorophenyloxy-(4-(trans-4-pentylcyclohexyl)cyclohexen-1-yl)difuluolomethane (compound number 279) and then values of physical properties were determined. From the results, the said compound had Cp: 50.4, $\Delta \epsilon$: 13.7, $\Delta n$: 0.070, η: 30.2, and Vth: 1.68V as extrapolative values.

Example 14 (Use Example 7)

Values of physical properties of the liquid crystal composition shown in Composition Example 1 were determined. The following results were obtained; Cp: 90.6, $\Delta \epsilon$: 7.6, $\Delta n$: 0.163, η: 17.0, and Vth: 2.01V.

Example 15 (Use Example 8)

Values of physical properties of the liquid crystal composition shown in Composition Example 2 were determined. The following results were obtained; Cp: 84.8, $\Delta \epsilon$: 9.3, $\Delta n$: 0.146, η: 19.4, and Vth: 1.90V.

Example 16 (Use Example 9)

Values of physical properties of the liquid crystal composition shown in Composition Example 3 were determined. The following results were obtained; Cp: 87.8, $\Delta \epsilon$: 31.3, $\Delta n$: 0.148, η: 87.6, and Vth: 0.85V.

Example 17 (Use Example 10)

Values of physical properties of the liquid crystal composition shown in Composition Example 4 were determined. The following results were obtained; Cp: 89.5, $\Delta \epsilon$: 7.2, $\Delta n$: 0.192, η: 38.8, and Vth: 2.10V.

Example 18 (Use Example 11)

Values of physical properties of the liquid crystal composition shown in Composition Example 5 were determined. The following results were obtained; Cp: 62.9, $\Delta \epsilon$: 12.0, $\Delta n$: 0.118, η: 43.4, and Vth: 1.24V.

Example 19 (Use Example 12)

Values of physical properties of the liquid crystal composition shown in Composition Example 6 were determined. The following results were obtained; Cp: 70.4, $\Delta \epsilon$: 9.0, $\Delta n$: 0.134, η: 23.0, and Vth: 1.66V.

Example 20 (Use Example 13)

Values of physical properties of the liquid crystal composition shown in Composition Example 7 were determined. The following results were obtained; Cp: 74.1, $\Delta \epsilon$: 24.2, $\Delta n$: 0.116, η: 39.0, and Vth: 0.98V.

Example 21 (Use Example 14)

Values of physical properties of the liquid crystal composition shown in Composition Example 8 were determined. The following results were obtained; Cp: 85.2, $\Delta \epsilon$: 5.7, $\Delta n$: 0.115, η: 17.5, and Vth: 2.22V.

Example 22 (Use Example 15)

Values of physical properties of the liquid crystal composition shown in Composition Example 9 were determined.

The following results were obtained; Cp: 82.6, Δε: 28.9, Δn: 0.142, η: 47.2, and Vth: 0.95V.

Example 23 (Use Example 16)

Values of physical properties of the liquid crystal composition shown in Composition Example 10 were determined. The following results were obtained; Cp: 63.4, Δε: 10.8, Δn: 0.116, η: 30.2, and Vth: 1.31V.

Example 24 (Use Example 17)

Values of physical properties of the liquid crystal composition shown in Composition Example 11 were determined. The following results were obtained; Cp: 62.6, Δε: 7.4, Δn: 0.160, η: 25.0, and Vth: 1.70V.

Example 25 (Use Example 18)

Values of physical properties of the liquid crystal composition shown in Composition Example 12 were determined. The following results were obtained; Cp: 93.5, Δε: 8.9, Δn: 0.127, η: 22.2, and Vth: 1.98V.

Example 26 (Use Example 19)

Values of physical properties of the liquid crystal composition shown in Composition Example 13 were determined. The following results were obtained; Cp: 94.7, Δε: 7.7, Δn: 0.204, η: 20.3, and Vth: 2.01V.

Example 27 (Use Example 20)

Values of physical properties of the liquid crystal composition shown in Composition Example 14 were determined. The following results were obtained; Cp: 79.2, Δε: 7.1, Δn: 0.123, η: 13.4, and Vth: 2.01V.

Example 28 (Use Example 21)

Values of physical properties of the liquid crystal composition shown in Composition Example 15 were determined. The following results were obtained; Cp: 91.7, Δε: 6.1, Δn: 0.100, η: 27.1, and Vth: 2.30V.

Example 29 (Use Example 22)

Values of physical properties of the liquid crystal composition shown in Composition Example 16 were determined. The following results were obtained; Cp: 100.0, Δε: 5.9, Δn: 0.097, η: 29.8, and Vth: 2.11V.

Example 30 (Use Example 23)

Values of physical properties of the liquid crystal composition shown in Composition Example 17 were determined. The following results were obtained; Cp: 84.6, Δε: 4.2, Δn: 0.088, η: 20.3, and Vth: 2.46V.

Example 31 (Use Example 24)

Values of physical properties of the liquid crystal composition shown in Composition Example 18 were determined. The following results were obtained; Cp: 79.5, Δε: 7.4, Δn: 0.110, η: 30.3, and Vth: 1.83V.

Example 32 (Use Example 25)

Values of physical properties of the liquid crystal composition shown in Composition Example 19 were determined. The following results were obtained; Cp: 70.0, Δε: 9.6, Δn: 0.092, η: 32.0, and Vth: 1.46V.

Example 33 (Use Example 26)

Values of physical properties of the liquid crystal composition shown in Composition Example 20 were determined. The following results were obtained; Cp: 76.3, Δε: 13.1, Δn: 0.089, η: 38.0, and Vth: 1.39V.

Example 34 (Use Example 27)

Values of physical properties of the liquid crystal composition shown in Composition Example 21 were determined. The following results were obtained; Cp: 86.9, Δε: 6.0, Δn: 0.124, η: 21.6, and Vth: 2.19V.

Example 35 (Use Example 28)

Values of physical properties of the liquid crystal composition shown in Composition Example 22 were determined. The following results were obtained; Cp: 97.8, Δε: 10.1, Δn: 0.118, η: 42.3, and Vth: 1.60V.

Example 36 (Use Example 29)

Values of physical properties of the liquid crystal composition shown in Composition Example 23 were determined. The following results were obtained; Cp: 84.5, Δε: 5.1, Δn: 0.093, η: 18.4, and Vth: 2.29V.

Example 37 (Use Example 30)

Values of physical properties of the liquid crystal composition shown in Composition Example 24 were determined. The following results were obtained; Cp: 68.5, Δε: 9.4, Δn: 0.097, η: 32.1, and Vth: 1.56V.

Example 38 (Use Example 31)

Values of physical properties of the liquid crystal composition shown in Composition Example 25 were determined. The following results were obtained; Cp: 95.2, Δε: 7.5, Δn: 0.134, η: 37.0, and Vth: 1.87V.

Example 39 (Use Example 32)

Values of physical properties of the liquid crystal composition shown in Composition Example 26 were determined. The following results were obtained; Cp: 70.3, Δε: 4.6, Δn: 0.087, η: 17.4, and Vth: 2.11V.

Example 40 (Use Example 33)

Values of physical properties of the liquid crystal composition shown in Composition Example 27 were determined. The following results were obtained; Cp: 90.2, Δε: 7.9, Δn: 0.092, η: 36.1, and Vth: 1.81V.

Example 41 (Use Example 34)

Values of physical properties of the liquid crystal composition shown in Composition Example 28 were determined. The following results were obtained; Cp: 93.4, Δε: 9.1, Δn: 0.128, η: 19.4, and Vth: 2.06V.

Example 42 (Use Example 35)

Values of physical properties of the liquid crystal composition shown in Composition Example 29 were determined. The following results were obtained; Cp: 76.3, Δε: 11.8, Δn: 0.097, η: 34.9, and Vth: 1.63V.

Further, use examples of compositions may be illustrated as follows. Herein, the compounds in the following use examples of the compositions are shown by abbreviations according to definitions shown in Table 1.

Use Example 1

| | |
|---|---|
| 3-HchCF2OB(F,F)-F | 2.0% |
| 3-HchCF2OB(F,F)-OCF3 | 2.0% |
| 3-HchCF2OB(F,F)-CF3 | 2.0% |
| 3-HchCF2OB(F,F)-OCF2H | 2.0% |
| 3-H2HB(F,F)-F | 7.0% |
| 3-HHB(F,F)-F | 10.0% |
| 4-HHB(F,F)-F | 5.0% |
| 3-HH2B(F,F)-F | 9.0% |
| 5-HH2B(F,F)-F | 9.0% |
| 3-HBB(F,F)-F | 15.0% |
| 5-HBB(F,F)-F | 15.0% |
| 3-HBEB(F,F)-F | 2.0% |
| 4-HBEB(F,F)-F | 2.0% |
| 5-HBEB(F,F)-F | 2.0% |
| 3-HHEB(F,F)-F | 10.0% |
| 4-HHEB(F,F)-F | 3.0% |
| 5-HHEB(F,F)-F | 3.0% |

NI = 78.7 (° C.)
$\eta$ = 32.6 (mPa · s)
$\Delta n$ = 0.093
$\Delta \epsilon$ = 11.9
Vth = 1.68 (V)

Use Example 2

| | |
|---|---|
| 3-Hch(F)CF2OB-F | 2.0% |
| 3-Hch(F)CF2OB-OCF3 | 2.0% |
| 3-Hch(F)CF2OB-CF3 | 2.0% |
| 3-Hch(F)CF2OB-OCF2H | 2.0% |
| 3-H2HB(F,F)-F | 7.0% |
| 3-HHB(F,F)-F | 10.0% |
| 4-HHB(F,F)-F | 5.0% |
| 3-HH2B(F,F)-F | 9.0% |
| 5-HH2B(F,F)-F | 9.0% |
| 3-HBB(F,F)-F | 15.0% |
| 5-HBB(F,F)-F | 15.0% |
| 3-HBEB(F,F)-F | 2.0% |
| 4-HBEB(F,F)-F | 2.0% |
| 5-HBEB(F,F)-F | 2.0% |
| 3-HHEB(F,F)-F | 10.0% |
| 4-HHEB(F,F)-F | 3.0% |
| 5-HHEB(F,F)-F | 3.0% |

NI = 80.2 (° C.)
$\eta$ = 32.7 (mPa · s)
$\Delta n$ = 0.094
$\Delta \epsilon$ = 11.94
Vth = 1.70 (V)

Use Example 3

| | |
|---|---|
| 3-HCF2OHB-F | 2.0% |
| 3-HCF2OHB-OCF3 | 2.0% |
| 3-HCF2OHB-CF3 | 2.0% |
| 3-HCF2OHB-OCF2H | 2.0% |
| 5-HB-F | 12.0% |
| 6-HB-F | 9.0% |
| 7-HB-F | 7.0% |
| 3-HHB-OCF3 | 6.0% |
| 4-HHB-OCF3 | 7.0% |
| 5-HHB-OCF3 | 5.0% |
| 3-HH2B-OCF3 | 4.0% |
| 5-HH2B-OCF3 | 4.0% |
| 3-HHB(F,F)-OCF3 | 5.0% |
| 3-HHB(F)-F | 10.0% |
| 5-HHB(F)-F | 10.0% |
| 3-HH2B(F)-F | 3.0% |
| 3-HB(F)BH-3 | 3.0% |
| 5-HBBH-3 | 3.0% |
| 3-HHB(F,F)-OCF2H | 4.0% |

NI = 87.1 (° C.)
$\eta$ = 15.9 (mPa · s)
$\Delta n$ = 0.092
$\Delta \epsilon$ = 4.3
Vth = 2.48 (V)

Use Example 4

| | |
|---|---|
| 3-HCF2OHB(F)—F | 2.0% |
| 3-HCF2OHB(F)—OCF3 | 2.0% |
| 3-HCF2OHB(F)—CF3 | 2.0% |
| 3-HCF2OHB(F)—OCF2H | 2.0% |
| 5-HHB(F)—F | 2.0% |
| 2-HBB(F)—F | 6.0% |
| 3-HBB(F)—F | 6.0% |
| 5-HBB(F)—F | 6.0% |
| 2-H2BB(F)—F | 9.0% |
| 3-H2BB(F)—F | 9.0% |
| 3-HBB(F,F)—F | 25.0% |
| 5-HBB(F,F)—F | 19.0% |
| 101-HBBH-4 | 5.0% |
| 101-HBBH-5 | 5.0% |

NI = 96.3(° C.)
$\eta$ = 35.6(mPa · s)
$\Delta n$ = 0.135
$\Delta \epsilon$ = 7.4
Vth = 1.89(V)

Use Example 5

| | |
|---|---|
| 3-HCF2OHB(F,F)—F | 2.0% |
| 3-HCF2OHB(F,F)—OCF3 | 2.0% |
| 3-HCF2OHB(F,F)—CF3 | 2.0% |
| 3-HCF2OHB(F,F)—OCF2H | 2.0% |
| 3-HHB(F,F)—F | 9.0% |
| 4-H2HB(F,F)—F | 8.0% |
| 5-H2HB(F,F)—F | 8.0% |
| 3-HBB(F,F)—F | 21.0% |
| 5-HBB(F,F)—F | 20.0% |
| 3-H2BB(F,F)—F | 10.0% |
| 5-HHBB(F,F)—F | 3.0% |
| 5-HHEBB—F | 2.0% |
| 3-HH2BB(F,F)—F | 3.0% |
| 101-HBBH-4 | 4.0% |
| 101-HBBH-5 | 4.0% |

NI = 100.7(° C.)
$\eta$ = 36.6(mPa · s)
$\Delta n$ = 0.118
$\Delta \epsilon$ = 9.4
Vth = 1.74(V)

Use Example 6

| | |
|---|---|
| 3-HchCF2OB—F | 2.0% |
| 3-HchCF2OB—OCF3 | 2.0% |
| 3-HchCF2OB—CF3 | 2.0% |
| 3-HchCF2OB—OCF2H | 2.0% |
| 5-HB—F | 12.0% |
| 6-HB—F | 9.0% |
| 7-HB—F | 7.0% |
| 3-HHB—OCF3 | 6.0% |
| 4-HHB—OCF3 | 7.0% |
| 5-HHB—OCF3 | 5.0% |
| 3-HH2B—OCF3 | 4.0% |

-continued

| | |
|---|---|
| 5-HH2B—OCF3 | 4.0% |
| 3-HBB(F,F)—OCF3 | 5.0% |
| 3-HBB(F)—F | 10.0% |
| 5-HBB(F)—F | 10.0% |
| 3-HH2B(F)—F | 3.0% |
| 3-HB(F)BH-3 | 3.0% |
| 5-HBBH-3 | 3.0% |
| 3-HHB(F,F)—OCF2H | 4.0% |
| NI = 83.5(° C.) | |
| η = 15.9(mPa · s) | |
| Δn = 0.092 | |
| Δε = 4.3 | |
| Vth = 2.38(V) | |

Use Example 7

| | |
|---|---|
| 3-HchCF20B(F)—F | 2.0% |
| 3-HchCF20B(F)—OCF3 | 2.0% |
| 3-HchCF20B(F)—CF3 | 2.0% |
| 3-HchCF20B(F)—OCF2H | 2.0% |
| 5-HHB(F)—F | 2.0% |
| 2-HBB(F)—F | 6.0% |
| 3-HBB(F)—F | 6.0% |
| 5-HBB(F)—F | 6.0% |
| 2-H2BB(F)—F | 9.0% |
| 3-H2BB(F)—F | 9.0% |
| 3-HBB(F,F)—F | 25.0% |
| 5-HBB(F,F)—F | 19.0% |
| 101-HBBH-4 | 5.0% |
| 101-HBBH-5 | 5.0% |
| NI = 94.5(° C.) | |
| η = 35.7(mPa · s) | |
| Δn = 0.135 | |
| Δε = 7.5 | |
| Vth = 1.87(V) | |

Use Example 8

| | |
|---|---|
| 3-HHCF20B(F,F)—F | 10.0% |
| 5-HHCF20B(F,F)—F | 5.0% |
| 5-HchCF20B(F,F)—F | 8.0% |
| 2-HHB(F)—F | 17.0% |
| 3-HHB(F)—F | 17.0% |
| 5-HHB(F)—F | 16.0% |
| 5-H2HB(F)—F | 2.0% |
| 2-HBB(F)-3 | 6.0% |
| 3-HBB(F)-3 | 6.0% |
| 5-HBB(F)-3 | 13.0% |
| NI = 96.4(° C.) | |
| η = 25.9(mPa · s) | |
| Δn = 0.097 | |
| Δε = 7.0 | |
| Vth = 2.01(V) | |

When 0.3 parts of CN was added to 100 parts of the above-mentioned composition, pitch was 78.0 μm.

Use Example 9

| | |
|---|---|
| 3-HHCF20B(F,F)—F | 10.0% |
| 5-HchCF20B(F,F)—F | 5.0% |
| 5-HHCF20B—OCF3 | 5.0% |
| 7-HB(F,F)—F | 3.0% |
| 3-HB-02 | 7.0% |

-continued

| | |
|---|---|
| 5-HHB(F)—F | 10.0% |
| 2-HBB(F)—F | 9.0% |
| 3-HBB(F)—F | 9.0% |
| 5-HBB(F)—F | 16.0% |
| 2-HBB—F | 4.0% |
| 3-HBB—F | 4.0% |
| 5-HBB—F | 3.0% |
| 3-HBB(F,F)—F | 5.0% |
| 5-HBB(F,F)—F | 10.0% |
| NI = 82.3(° C.) | |
| η = 25.1(mPa · s) | |
| Δn = 0.113 | |
| Δε = 6.8 | |
| Vth = 1.77(V) | |

Use Example 10

| | |
|---|---|
| 5-HCF20B—F | 2.0% |
| 5-HCF20B—OCF3 | 2.0% |
| 5-HCF20B—CF3 | 2.0% |
| 5-HCF20B—OCF2H | 2.0% |
| 3-HB—CL | 10.0% |
| 101-HH-5 | 5.0% |
| 2-HBB(F)—F | 8.0% |
| 3-HBB(F)—F | 8.0% |
| 5-HBB(F)—F | 14.0% |
| 4-HHB—CL | 8.0% |
| 5-HHB—CL | 8.0% |
| 3-H2HB(F)—CL | 4.0% |
| 3-HBB(F,F)—F | 10.0% |
| 5-H2BB(F,F)—F | 9.0% |
| 3-HB(F)VB-2 | 4.0% |
| 3-HB(F)VB-3 | 4.0% |
| NI = 89.7(° C.) | |
| η = 22.2(mPa · s) | |
| Δn = 0.125 | |
| Δε = 4.8 | |
| Vth = 2.17(V) | |

Use Example 11

| | |
|---|---|
| 3-HHCF20B—F | 2.0% |
| 3-HHCF20B(F)—F | 2.0% |
| 3-HHCF20B—CF3 | 2.0% |
| 3-HHCF20B—OCF2H | 2.0% |
| 2-HHB(F)—F | 17.0% |
| 3-HHB(F)—F | 17.0% |
| 5-HHB(F)—F | 16.0% |
| 3-H2HB(F)—F | 7.0% |
| 5-H2HB(F)—F | 10.0% |
| 2-HBB(F)—F | 6.0% |
| 3-HBB(F)—F | 6.0% |
| 5-HBB(F)—F | 13.0% |
| NI = 106.2(° C.) | |
| η = 25.9(mPa · s) | |
| Δn = 0.097 | |
| Δε = 5.4 | |
| Vth = 2.21(V) | |

Use Example 12

| | |
|---|---|
| 3-HHCF20B(F)—OCF3 | 2.0% |
| 3-HHCF20B(F)—CF3 | 2.0% |

-continued

| | |
|---|---|
| 3-HHCF2OB(F)—OCF2H | 2.0% |
| 7-HB(F,F)—F | 3.0% |
| 3-HB-02 | 7.0% |
| 2-HHB(F)—F | 4.0% |
| 3-HHB(F)—F | 10.0% |
| 5-HHB(F)—F | 10.0% |
| 2-HBB(F)—F | 9.0% |
| 3-HBB(F)—F | 9.0% |
| 5-HBB(F)—F | 16.0% |
| 2-HBB—F | 4.0% |
| 3-HBB—F | 4.0% |
| 5-HBB—F | 3.0% |
| 3-HBB(F,F)—F | 5.0% |
| 5-HBB(F,F)—F | 10.0% |
| NI = 87.0(° C.) | |
| η = 25.7(mPa · s) | |
| Δn = 0.116 | |
| Δε = 6.0 | |
| Vth = 2.00(V) | |

Use Example 13

| | |
|---|---|
| 5-HCF2OB(F)—F | 2.0% |
| 5-HCF2OB(F)—OCF3 | 2.0% |
| 5-HCF2OB(F)—CF3 | 2.0% |
| 5-HCF2OB(F)—OCF2H | 2.0% |
| 3-HB—CL | 10.0% |
| 101-HH-5 | 5.0% |
| 2-HBB(F)—F | 8.0% |
| 3-HBB(F)—F | 8.0% |
| 5-HBB(F)—F | 14.0% |
| 4-HHB—CL | 8.0% |
| 5-HHB—CL | 8.0% |
| 3-H2HB(F)—CL | 4.0% |
| 3-HBB(F,F)—F | 10.0% |
| 5-H2BB(F,F)—F | 9.0% |
| 3-HB(F)VB-2 | 4.0% |
| 3-HB(F)VB-3 | 4.0% |
| NI = 88.0(° C.) | |
| η = 22.9(mPa · s) | |
| Δn = 0.124 | |
| Δε = 5.0 | |
| Vth = 2.15(V) | |

Use Example 14

| | |
|---|---|
| 3-Hch(F)CF2OB(F)—F | 2.0% |
| 3-Hch(F)CF2OB(F)—OCF3 | 2.0% |
| 3-Hch(F)CF2OB(F,F)—F | 2.0% |
| 3-Hch(F)CF2OB(F,F)—OCF3 | 2.0% |
| 2-HHB(F)—F | 17.0% |
| 3-HHB(F)—F | 17.0% |
| 5-HHB(F)—F | 16.0% |
| 2-H2HB(F)—F | 10.0% |
| 5-H2HB(F)—F | 7.0% |
| 2-HBB(F)—F | 6.0% |
| 3-HBB(F)—F | 6.0% |
| 5-HBB(F)—F | 13.0% |
| NI = 97.4(° C.) | |
| η = 28.0(mPa · s) | |
| Δn = 0.095 | |
| Δε = 5.5 | |
| Vth = 2.09(V) | |

Use Example 15

| | |
|---|---|
| 5-ch(F)CF2OB(F)—CF3 | 2.0% |
| 5-ch(F)CF2OB(F)—CF2H | 2.0% |
| 5-ch(F)CF2OB(F,F)—CF3 | 2.0% |
| 5-ch(F)CF2OB(F,F)—OCF2H | 2.0% |
| 7-HB(F,F)—F | 3.0% |
| 3-HB-02 | 3.0% |
| 2-HHB(F)—F | 6.0% |
| 3-HHB(F)—F | 10.0% |
| 5-HHB(F)—F | 10.0% |
| 2-HBB(F)—F | 9.0% |
| 3-HBB(F)—F | 9.0% |
| 5-HBB(F)—F | 16.0% |
| 2-HBB—F | 4.0% |
| 3-HBB—F | 4.0% |
| 5-HBB—F | 3.0% |
| 3-HBB(F,F)—F | 5.0% |
| 5-HBB(F,F)—F | 10.0% |
| NI = 80.5(° C.) | |
| η = 27.7(mPa · s) | |
| Δn = 0.113 | |
| Δε = 6.2 | |
| Vth = 1.75(V) | |

Use Example 16

| | |
|---|---|
| 5-ch(F)CF2OB—F | 1.0% |
| 5-ch(F)CF2OB—OCF3 | 1.0% |
| 5-ch(F)CF2OB(F)—F | 1.0% |
| 5-ch(F)CF2OB(F)—OCF3 | 1.0% |
| 5-ch(F)CF2OB(F,F)—F | 1.0% |
| 5-ch(F)CF2OB(F,F)—OCF3 | 1.0% |
| 5-ch(F)CF2OB—CF3 | 1.0% |
| 5-ch(F)CF2OB—OCF2H | 1.0% |
| 3-HB—CL | 10.0% |
| 101-HH-5 | 5.0% |
| 2-HBB(F)—F | 8.0% |
| 3-HBB(F)—F | 8.0% |
| 5-HBB(F)—F | 14.0% |
| 4-HHB—CL | 8.0% |
| 5-HHB—CL | 8.0% |
| 3-H2HB(F)—CL | 4.0% |
| 3-HBB(F,F)—F | 10.0% |
| 5-H2BB(F,F)—F | 9.0% |
| 3-HB(F)—VB-2 | 4.0% |
| 3-HB(F)—VB-3 | 4.0% |
| NI = 85.6(° C.) | |
| η = 24.2(mPa · s) | |
| Δn = 0.124 | |
| Δε = 4.9 | |
| Vth = 2.12(V) | |

Use Example 17

| | |
|---|---|
| 3-Hch(F)CF2OB(F)—CF3 | 2.0% |
| 3-Hch(F)CF2OB(F)—OCF2H | 2.0% |
| 3-Hch(F)CF2OB(F,F)—CF3 | 2.0% |
| 3-Hch(F)CF2OB(F,F)—OCF2H | 2.0% |
| 3-H2HB(F,F)—F | 7.0% |
| 3-HHB(F,F)—F | 10.0% |
| 4-HHB(F,F)—F | 5.0% |
| 3-HH2B(F,F)—F | 9.0% |
| 5-HH2B(F,F)—F | 9.0% |
| 3-HBB(F,F)—F | 15.0% |
| 5-HBB(F,F)—F | 15.0% |
| 3-HBEB(F,F)—F | 2.0% |
| 4-HBEB(F,F)—F | 2.0% |
| 5-HBEB(F,F)—F | 2.0% |
| 3-HHEB(F,F)—F | 10.0% |

-continued

| | |
|---|---|
| 4-HHEB(F,F)—F | 3.0% |
| 5-HHEB(F,F)—F | 3.0% |
| NI = 77.8(° C.) | |
| η = 34.6(mPa · s) | |
| Δn = 0.094 | |
| Δε = 11.8 | |
| Vth = 1.67(V) | |

Use Example 18

| | |
|---|---|
| 3-HHCF2OBB—F | 2.0% |
| 3-HHCF2OBB—OCF3 | 2.0% |
| 3-HHCF2OBB—CF3 | 2.0% |
| 3-HHCF2OBB—OCF2H | 2.0% |
| 3-HHB(F,F)—F | 5.0% |
| 3-H2HB(F,F)—F | 8.0% |
| 4-H2HB(F,F)—F | 8.0% |
| 5-H2HB(F,F)—F | 8.0% |
| 3-HBB(F,F)—F | 21.0% |
| 5-HBB(F,F)—F | 20.0% |
| 3-H2BB(F,F)—F | 10.0% |
| 5-HHBB(F,F)—F | 3.0% |
| 5-HHEBB—F | 2.0% |
| 3-HH2BB(F,F)—F | 3.0% |
| 101-HBBH-5 | 4.0% |
| NI = 99.0(° C.) | |
| η = 35.0(mPa · s) | |
| Δn = 0.113 | |
| Δε = 9.2 | |
| Vth = 1.80(V) | |

Use Example 19

| | |
|---|---|
| 5-HCF2OB(F,F)—F | 2.0% |
| 5-HCF2OB(F,F)—OCF3 | 2.0% |
| 5-HCF2OB(F,F)—CF3 | 2.0% |
| 5-HCF2OB(F,F)—OCF2H | 2.0% |
| 5-HB—F | 12.0% |
| 6-HB—F | 8.0% |
| 2-HHB—OCF3 | 7.0% |
| 3-HHB—OCF3 | 7.0% |
| 4-HHB—OCF3 | 7.0% |
| 5-HHB—OCF3 | 5.0% |
| 3-HH2B—OCF3 | 4.0% |
| 5-HH2B—OCF3 | 4.0% |
| 3-HHB(F,F)—OCF3 | 5.0% |
| 3-HBB(F)—F | 10.0% |
| 5-HBB(F)—F | 10.0% |
| 3-HH2B(F)—F | 3.0% |
| 3-HB(F)BH-3 | 3.0% |
| 5-HBBH-3 | 3.0% |
| 3-HHB(F,F)—OCF2H | 4.0% |
| NI = 82.6(° C.) | |
| η = 18.1(mPa · s) | |
| Δn = 0.090 | |
| Δε = 5.3 | |
| Vth = 2.12(V) | |

Use Example 20

| | |
|---|---|
| 3-HHCF2OBB(F)—F | 1.0% |
| 3-HHCF2OBB(F)—OCF3 | 1.0% |
| 3-HHCF2OBB(F,F)—F | 1.0% |
| 3-HHCF2OBB(F,F)—OCF3 | 1.0% |
| 3-HHCF2OBB(F)—CF3 | 1.0% |

| | |
|---|---|
| 2-HHB(F)—F | 2.0% |
| 3-HHB(F)—F | 2.0% |
| 5-HHB(F)—F | 2.0% |
| 2-HBB(F)—F | 6.0% |
| 3-HBB(F)—F | 6.0% |
| 5-HBB(F)—F | 10.0% |
| 2-H2BB(F)—F | 9.0% |
| 3-H2BB(F)—F | 9.0% |
| 3-HBB(F,F)—F | 25.0% |
| 5-HBB(F,F)—F | 19.0% |
| 101-HBBH-5 | 5.0% |
| NI = 96.3(° C.) | |
| η = 35.9(mPa · s) | |
| Δn = 0.131 | |
| Δε = 7.7 | |
| Vth = 1.88(V) | |

Use Example 21

| | |
|---|---|
| 3-HHCF2OBB(F)—OCF2H | 1.0% |
| 3-HHCF2OBB(F,F)—CF3 | 1.0% |
| 3-HHCF2OBB(F,F)OCF2H | 1.0% |
| 3-Hch(F)CF2OBB—F | 1.0% |
| 3-HHB(F,F)—F | 9.0% |
| 3-H2HB(F,F)—F | 8.0% |
| 4-H2HB(F,F)—F | 8.0% |
| 5-H2HB(F,F)—F | 8.0% |
| 3-HBB(F,F)—F | 21.0% |
| 5-HBB(F,F)—F | 20.0% |
| 3-H2BB(F,F)—F | 10.0% |
| 5-HHBB(F,F)—F | 3.0% |
| 5-HHEBB—F | 2.0% |
| 3-HH2BB(F.F)—F | 3.0% |
| 101-HBBH-5 | 4.0% |
| NI = 97.5(° C.) | |
| η = 35.9(mPa · s) | |
| Δn = 0.112 | |
| Δε = 9.3 | |
| Vth = 1.70(V) | |

Use Example 22

| | |
|---|---|
| 3-Hch(F)CF2OBB—OCF3 | 1.0% |
| 3-Hch(F)CF2OBB(F)—F | 1.0% |
| 3-Hch(F)CF2OBB(F)—OCF3 | 1.0% |
| 3-Hch(F)CF2OBB(F,F)—F | 1.0% |
| 3-Hch(F)CF2OBB(F,F)—OCF3 | 1.0% |
| 2-HHB(F)—F | 2.0% |
| 3-HHB(F)—F | 2.0% |
| 5-HHB(F)—F | 2.0% |
| 2-HBB(F)—F | 6.0% |
| 3-HBB(F)—F | 6.0% |
| 5-HBB(F)—F | 10.0% |
| 2-H2BB(F)—F | 9.0% |
| 3-H2BB(F)—F | 9.0% |
| 3-HBB(F,F)—F | 25.0% |
| 5-HBB(F,F)—F | 19.0% |
| 101-HBBH-4 | 5.0% |
| NI = 94.1(° C.) | |
| η = 36.6(mPa · s) | |
| Δn = 0.131 | |
| Δε = 7.7 | |
| Vth = 1.85(V) | |

Use Example 23

| | |
|---|---|
| 3-Hch(F)CF2OBB—CF3 | 1.0% |
| 3-Hch(F)CF2OBB—OCF2H | 1.0% |
| 3-Hch(F)CF2OBB(F)—CF3 | 1.0% |
| 3-Hch(F)CF2OBB(F)—OCF2H | 1.0% |
| 3-Hch(F)CF2OBB(F,F)—CF3 | 1.0% |
| 3-Hch(F)CF2OBB(F,F)—OCF2H | 1.0% |
| 2-HHB(F)—F | 2.0% |
| 3-HHB(F)—F | 2.0% |
| 5-HHB(F)—F | 2.0% |
| 2-HBB(F)—F | 6.0% |
| 3-HBB(F)—F | 6.0% |
| 5-HBB(F)—F | 10.0% |
| 2-H2BB(F)—F | 9.0% |
| 3-H2BB(F)—F | 9.0% |
| 3-HBB(F,F)—F | 25.0% |
| 5-HBB(F,F)—F | 19.0% |
| 101-HBBH-5 | 4.0% |

NI = 92.4(° C.)
$\eta$ = 37.4(mPa · s)
$\Delta n$ = 0.130
$\Delta \epsilon$ = 7.8
Vth = 1.85(V)

Use Example 24

| | |
|---|---|
| 3-HHCF2OB(F,F)—F | 11.0% |
| 1V2-BEB(F,F)—C | 5.0% |
| 3-HB—C | 25.0% |
| 1-BTB-3 | 5.0% |
| 2-BTB-1 | 10.0% |
| 3-HH-4 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |

NI = 82.8(° C.)
$\eta$ = 14.3(mPa · s)
$\Delta n$ = 0.158
$\Delta \epsilon$ = 8.3
Vth = 1.98(V)

When 0.8 parts of CM33 was added to 100 parts of the above-mentioned composition, pitch was 12.0 $\mu$m.

Use Example 25

| | |
|---|---|
| 5-HHCF2OB—OCF3 | 8.0% |
| 201-BEB(F)—C | 5.0% |
| 301-BEB(F)—C | 15.0% |
| 401-BEB(F)—C | 13.0% |
| 501-BEB(F)—C | 13.0% |
| 2-HHB(F)—C | 15.0% |
| 3-HHB(F)—C | 15.0% |
| 3-HB(F)TB-2 | 4.0% |
| 3-HB(F)TB-3 | 4.0% |
| 3-HB(F)TB-4 | 4.0% |
| 3-HHB-01 | 4.0% |

NI = 90.1(° C.)
$\eta$ = 86.0(mPa · s)
$\Delta n$ = 0.148
$\Delta \epsilon$ = 31.3
Vth = 0.84(V)

Use Example 26

| | |
|---|---|
| 5-HHCF2OB(F,F)—F | 5.0% |
| 3-BEB(F)—C | 8.0% |
| 3-HB—C | 8.0% |
| V-HB—C | 8.0% |
| 1V-HB—C | 8.0% |
| 3-HB-02 | 3.0% |
| 3-HH-2V | 14.0% |
| 3-HH-2V1 | 7.0% |
| V2-HHB-1 | 15.0% |
| 3-HHB-1 | 5.0% |
| 3-HHEB—F | 2.0% |
| 3-H2BTB-2 | 6.0% |
| 3-H2BTB-3 | 6.0% |
| 3-H2BTB-4 | 5.0% |

NI = 95.6(° C.)
$\eta$ = 15.7(mPa · s)
$\Delta n$ = 0.133
$\Delta \epsilon$ = 9.0
Vth = 2.12(V)

Use Example 27

| | |
|---|---|
| 3-HCF2OBB—F | 2.0% |
| 3-HCF2OBB(F)—F | 2.0% |
| 3-HCF2OBB(F,F)—F | 2.0% |
| 3-HCF2OBB(F)B—F | 2.0% |
| 3-HCF2OB(F)B(F)—F | 2.0% |
| 3-HCF2OB(F)B(F,F)—F | 2.0% |
| 3-HCF2OB(F,F)B—F | 2.0% |
| 3-HCF2OB(F,F)B(F)—F | 2.0% |
| 3-HCF2OB(F,F)B(F,F)—F | 2.0% |
| 7-HB(F,F)—F | 12.0% |
| 3-H2HB(F,F)—F | 3.0% |
| 4-H2HB(F,F)—F | 10.0% |
| 5-H2HB(F,F)—F | 10.0% |
| 3-HHB(F,F)—F | 10.0% |
| 4-HHB(F,F)—F | 5.0% |
| 3-HH2B(F,F)—F | 8.0% |
| 3-HBB(F,F)—F | 12.0% |
| 5-HBB(F,F)—F | 12.0% |

Use Example 28

| | |
|---|---|
| 3-HCF2OBB—OCF3 | 2.0% |
| 3-HCF2OBB(F)—OCF3 | 2.0% |
| 3-HCF2OBB(F,F)—OCF3 | 2.0% |
| 3-HCF2OB(F)B—OCF3 | 2.0% |
| 3-HCF2OB(F)B(F)—OCF3 | 2.0% |
| 3-HCF2OB(F)B(F,F)—OCF3 | 2.0% |
| 3-HCF2OB(F,F)B—OCF3 | 2.0% |
| 3-HCF2OB(F,F)B(F)—OCF3 | 2.0% |
| 3-HCF2OB(F,F)B(F,F)—OCF3 | 2.0% |
| 7-HB(F,F)—F | 12.0% |
| 3-H2HB(F,F)—F | 3.0% |
| 4-H2HB(F,F)—F | 10.0% |
| 5-H2HB(F,F)—F | 10.0% |
| 3-HHB(F,F)—F | 10.0% |
| 4-HHB(F,F)—F | 5.0% |
| 3-HH2B(F,F)—F | 8.0% |
| 3-HBB(F,F)—F | 12.0% |
| 5-HBB(F,F)—F | 12.0% |

Use Example 29

| | |
|---|---|
| 3-HCF2OBB—CF3 | 2.0% |
| 3-HCF2OBB(F)—CF3 | 2.0% |
| 3-HCF2OBB(F,F)—CF3 | 2.0% |
| 3-HCF2OB(F)B—CF3 | 2.0% |
| 3-HCF2OB(F)B(F)—CF3 | 2.0% |
| 3-HCF2OB(F)B(F,F)—CF3 | 2.0% |
| 3-HCF2OB(F,F)B—CF3 | 2.0% |
| 3-HCF2OB(F,F)B(F)—CF3 | 2.0% |
| 3-HCF2OB(F,F)B(F,F)—CF3 | 2.0% |
| 7-HB(F,F)—F | 12.0% |
| 3-H2HB(F,F)—F | 3.0% |
| 4-H2HB(F,F)—F | 10.0% |
| 5-H2HB(F,F)—F | 10.0% |
| 3-HHB(F,F)—F | 10.0% |
| 4-HHB(F,F)—F | 5.0% |
| 3-HH2B(F,F)—F | 8.0% |
| 3-HBB(F,F)—F | 12.0% |
| 5-HBB(F,F)—F | 12.0% |

Use Example 30

| | |
|---|---|
| 3-HCF2OBB—OCF2H | 2.0% |
| 3-HCF2OBB(F)—OCF2H | 2.0% |
| 3-HCF2OBB(F,F)—OCF2H | 2.0% |
| 3-HCF2OB(F)B—OCF2H | 2.0% |
| 3-HCF2OB(F)B(F)—OCF2H | 2.0% |
| 3-HCF2OB(F)B(F,F)—OCF2H | 2.0% |
| 3-HCF2OB(F,F)B—OCF2H | 2.0% |
| 3-HCF2OB(F,F)B(F)—OCF2H | 2.0% |
| 3-HCF2OB(F,F)B(F,F)—OCF2H | 2.0% |
| 7-HB(F,F)—F | 12.0% |
| 3-H2HB(F,F)—F | 3.0% |
| 4-H2HB(F,F)—F | 10.0% |
| 5-H2HB(F,F)—F | 10.0% |
| 3-HHB(F,F)—F | 10.0% |
| 4-HHB(F,F)—F | 5.0% |
| 3-HH2B(F,F)—F | 8.0% |
| 3-HBB(F,F)—F | 12.0% |
| 5-HBB(F,F)—F | 12.0% |

Use Example 31

| | |
|---|---|
| 3-H2HCF2OB(F,F)—F | 2.0% |
| 3-H2HCF2OB(F,F)—CF3 | 2.0% |
| 3-H2HCF2OB(F,F)—OCF3 | 2.0% |
| 3-H2HCF2OB(F,F)—OCF2H | 2.0% |
| 3-HCF2OHCF2OB(F,F)—F | 2.0% |
| 3-HCF2OHCF2OB(F,F)—CF3 | 2.0% |
| 3-HCF2OHCF2OB(F,F)—OCF3 | 2.0% |
| 3-HCF2OHCF2OB(F,F)—OCF2H | 2.0% |
| 7-HB(F,F)—F | 12.0% |
| 3-H2HB(F,F)—F | 5.0% |
| 4-H2HB(F,F)—F | 10.0% |
| 5-H2HB(F,F)—F | 10.0% |
| 3-HHB(F,F)—F | 10.0% |
| 4-HHB(F,F)—F | 5.0% |
| 3-HH2B(F,F)—F | 8.0% |
| 3-HBB(F,F)—F | 12.0% |
| 5-HBB(F,F)—F | 12.0% |

Use Example 32

| | |
|---|---|
| 3-HHHCF2OB(F,F)—F | 2.0% |
| 3-HHHCF2OB(F,F)—OCF3 | 2.0% |
| 3-HHHCF2OB(F,F)—CF3 | 2.0% |
| 3-HHHCF2OB(F,F)—OCF2H | 2.0% |
| 7-HB(F,F)—F | 13.0% |
| 3-H2HB(F,F)—F | 12.0% |
| 4-H2HB(F,F)—F | 10.0% |
| 5-H2HB(F,F)—F | 10.0% |
| 3-HHB(F,F)—F | 10.0% |
| 4-HHB(F,F)—F | 5.0% |
| 3-HH2B(F,F)—F | 13.0% |
| 3-HBB(F,F)—F | 15.0% |
| 3-HHBB(F,F)—F | 4.0% |

Use Example 33

| | |
|---|---|
| 3O1-HHCF2OB(F,F)—F | 5.0% |
| IV2-HHCF2OB(F,F)—F | 5.0% |
| F4-HHCF2OB(F,F)—F | 5.0% |
| 7-HB(F,F)—F | 13.0% |
| 3-H2HB(F,F)—F | 12.0% |
| 4-H2HB(F,F)—F | 3.0% |
| 5-H2HB(F,F)—F | 10.0% |
| 3-HHB(F,F)—F | 10.0% |
| 4-HHB(F,F)—F | 5.0% |
| 3-HH2B(F,F)—F | 13.0% |
| 3-HBB(F,F)—F | 15.0% |
| 5-HHBB(F,F)—F | 4.0% |

Use Example 34

| | |
|---|---|
| 2-HHCF2OB(F,F)—F | 10.0% |
| 3-HHCF2OB(F,F)—F | 10.0% |
| 4-HHCF2OB(F,F)—F | 10.0% |
| 5-HHCF2OB(F,F)—F | 10.0% |
| 7-HB(F,F)—F | 13.0% |
| 3-H2HB(F,F)—F | 10.0% |
| 4-H2HB(F,F)—F | 3.0% |
| 5-H2HB(F,F)—F | 10.0% |
| 4-HHB(F,F)—F | 5.0% |
| 3-HBB(F,F)—F | 15.0% |
| 5-HHBB(F,F)—F | 4.0% |

Use Example 35

| | |
|---|---|
| 2-HHCF2OB(F,F)—F | 8.0% |
| 3-HHCF2OB(F,F)—F | 8.0% |
| 4-HHCF2OB(F,F)—F | 8.0% |
| 5-HHCF2OB(F,F)—F | 8.0% |
| 2-HHCF2OB(F)—OCF3 | 7.0% |
| 3-HHCF2OB(F)—OCF3 | 7.0% |
| 4-HHCF2OB(F)—OCF3 | 7.0% |
| 5-HHCF2OB(F)—OCF3 | 7.0% |
| 7-HB(F,F)—F | 13.0% |
| 5-H2HB(F,F)—F | 8.0% |
| 3-HBB(F,F)—F | 15.0% |
| 3-HHBB(F,F)—F | 4.0% |

Comparative Example

Amongst of the compound (13) shown in the column of the prior arts, the compound wherein R being n-pentyl group (hereinafter referred to comparative compound (13-1)) was synthesized according to the description in the said specification.

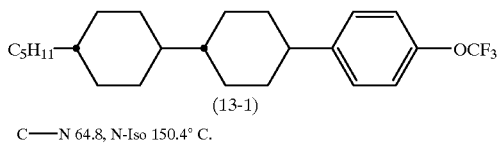

(13-1)

C——N 64.8, N-Iso 150.4° C.

15% by weight of the comparative compound (13-1) was mixed with 85% by weight of mother liquid crystals A shown in the above-mentioned Example 8 (Use Example 1) to determine values of physical properties. Also, the compound according to the present invention (compound number 127) described in Example 5 was determined similarly. Results of physical properties determined as to both compounds are shown in Table 2.

Δε, superior stability and superior compatibility, as well as a superior liquid crystal display element by use of them.

What is claimed is:

1. A compound expressed by the general formula (1):

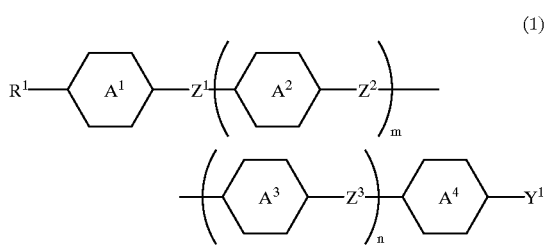

(1)

wherein $R^1$ denotes an alkyl group having from 1 to 20 carbon atoms in which one or more methylene groups in said group may be replaced by oxygen atoms or —CH=CH—

TABLE 2

| structure | NI(° C.) | Δε | η(mPa · s) | Vth(V) |
|---|---|---|---|---|
| C₅H₁₁—⬡—⬡—⌬—OCF₃ (13-1) | 78.4 | 10.5 | 26.3 | 1.88 |
| | (116.4) | (7.67) | (29.1) | |
| C₅H₁₁—⬡—⬡—CF₂O—⌬—OCF₃ compound No. 127 | 82.5 | 10.8 | 25.8 | 1.81 |
| | (143.7) | (9.7) | (23.5) | |

(In the table, numerical values in parentheses are extrapolated from mother liquid crystals A.)

As seen from the table, the compound according to the present invention shows larger dielectric anisotropy than the comparative compound (13-1), and also the former shows the clear point of about 143.7° C. by extrapolation, which being about 27° C. higher than the compound (13-1). Further, it should be mentioned specially that the former shows about 19% lower viscosity as an extrapolative value than the compound (13-1). Thus, the compounds according to the present application have a wider liquid crystal phase temperature range, a lower viscosity and a lower threshold voltage than the prior compounds, as well as shows superior characteristics which are not present in the prior compounds.

Compounds according to the present invention have a very high voltage holding ratio, low threshold voltage, quite low temperature-dependency and large Δε, and the said compound can be mixed easily with any of various liquid crystal materials, and also the said compound has good solubility even at a low temperature. Further, the liquid crystal compounds according to the present invention can be provided novel liquid crystalline compounds having desired physical properties by selecting (a) substituent(s) and (a) bonding group(s) suitablly.

Therefore, by using liquid crystalline compounds according to the present invention as a component of a liquid crystal composition, there can be provided novel liquid crystal compositions having a quite high voltage holding ratio, low threshold voltage, a quite narrow temperature range, low threshold voltage, suitable magnitude of Δn and and one or more hydrogen atoms in said group may be replaced by fluorine or chlorine atoms, with the proviso that two or more methylene groups may not be continuously replaced by oxygen atoms, $Y^1$ denotes an alkoxy group having 2 to 5 carbon atoms, in which at least one hydrogen atom is replaced by a fluorine atom and one or more hydrogen atoms may be further replaced by chlorine atoms, $Z^1$, $Z^2$ and $Z^3$ each independently denote a covalent bond, —CH₂CH₂—, —CH=CH—, —COO— or —CF₂O—, with the proviso that at least one of $Z^1$, $Z^2$ and $Z^3$ is —COO— or —CF₂O—, rings $A^1$, $A^2$, $A^3$ and $A^4$ each independently denote trans-1,4-cyclohexylene, 3-cyclohexen-1,4-ylene, 3-fluoro-3-cyclohexen-1,4-ylene, pyrimidine-2,5-diyl, 1,3-dioxan-2,5-diyl, trans-1-sila-1,4-cyclohexylene, trans-4-sila-1,4-cyclohexylene, or 1,4-phenylene in which one or more hydrogen atoms may be replaced by fluorine atoms or chlorine atoms, and m and n denote 0 or 1, with the proviso that when $Z^1$, $Z^2$ or $Z^3$ is —CF₂O—, then at least two groups selected from rings $A^1$, $A^2$, $A^3$ and $A^4$ directly bonded to —CF₂O— are both 1,4-phenylene in which one or more hydrogen atoms may be replaced by fluorine atoms or chlorine atoms, and any of the rings $A^1$, $A^2$ and $A^3$ bonded with the carbon atoms of —CF₂O— is 1,4-phenylene in which at least one hydrogen atom is replaced by fluorine or chlorine atoms.

2. A compound according to claim 1, wherein m=n=0 and $Z^1$ is —COO— in the general formula (1).

3. A compound according to claim 1, wherein m=1, n=0 and $Z^2$ is —COO— in the general formula (1).

4. A compound according to claim 1, wherein m=1, n=0, and $Z^1$ is —CF$_2$O— in the general formula (1).

5. A compound according to claim 1, wherein m=1, n=0, and $Z^2$ is —CF$_2$O— in the general formula (1).

6. A compound according to claim 1, wherein m=n=1 and $Z^3$ is —COO— in the general formula (1).

7. A compound according to claim 1, wherein m=n=1, $Z^2$ is —CF$_2$O— and $A^4$ is 1,4-phenylene in which one or more hydrogen atoms may be replaced by fluorine atoms in the general formula (1).

8. A compound according to claim 1, wherein m=n=1, $Z^2$ is —CF$_2$O—, $A^4$ is 1,4-phenylene in which one or more hydrogen atoms may be replaced by fluorine atoms and $Z^3$ is a covalent bond in the general formula (1).

9. A compound according to claim 1, wherein m=n=1, $Z^3$ is —CF$_2$O—, and $A^1$ and $A^2$ are both trans-1,4-cyclohexylene in the general formula (1).

10. A compound according to claim 1, wherein m=n=1, $Z^3$ is —CF$_2$O—, $A^1$ is trans-1,4-cyclohexylene, and $A^2$ is 1,4-phenylene in which one or more hydrogen atoms may be replaced by fluorine atoms in the general formula (1).

11. A liquid crystal composition comprising at least two components, at least one of which is a compound expressed by the general formula (1) according to claim 1.

12. A liquid crystal composition comprising at least one compound according to claim 1 as a first component, and at least one compound selected from the group consisting of compounds having the general formulae (2), (3) and (4) as a second component:

(2)

(3)

(4)

wherein $R^2$ denotes an alkyl group having from 1 to 10 carbon atoms, in which optional non-adjacent methylene groups in said group may be replaced by oxygen atoms or —CH=CH— and optional hydrogen atoms in said group may be replaced by fluorine atoms, $Y^2$ denotes a fluorine atom, a chlorine atom, OCF$_3$, OCF$_2$H, CF$_3$, CF$_2$H, CFH$_2$, OCF$_2$CF$_2$H or OCF$_2$CFHCF$_3$, $L^1$ and $L^2$ each independently denote a hydrogen atom or a fluorine atom, $Z^4$ and $Z^5$ each independently denote —CH$_2$CH$_2$—, —CH=CH—, 1,4-butylene group, —COO—, —CF$_2$O—, —OCF$_2$— or a covalent bond, ring B denotes trans-1,4-cyclohexylene, 1,3-dioxane-2,5-diyl, or 1,4-phenylene in which hydrogen atoms may be replaced by fluorine atoms, and ring C denotes trans-1,4-cyclohexylene or 1,4-phenylene in which hydrogen atoms may be replaced by fluorine atoms.

13. A liquid crystal composition comprising at least one compound according to claim 1 as a first component, and at least one compound selected from the group consisting of compounds having the general formulae (5) and (6) as a second component:

(5)

(6)

wherein $R^3$ and $R^4$ each independently denote an alkyl group having from 1 to 10 carbon atoms, in which optional non-adjacent methylene groups in said group may be replaced by oxygen atoms or —CH=CH— and optional hydrogen atoms in said group may be replaced by fluorine atoms, $Y^3$ denotes CN group or C≡C—CN, ring D denotes trans-1,4-cyclohexylene, 1,4-phenylene, pyrimidine-2,5-diyl or 1,3-dioxane-2,5-diyl, ring E denotes trans-1,4-cyclohexylene, 1,4-phenylene in which hydrogen atoms may be replaced by fluorine atoms, or pyrimidine-2,5-diyl, ring F denotes trans-1,4-cyclohexylene or 1,4-phenylene, $Z^6$ denotes —CH$_2$CH$_2$—, —COO— or a covalent bond, $L^3$, $L^4$ and $L^5$ each independently denote a hydrogen atom or a fluorine atom, a, b and c each independently denote 0 or 1.

14. A liquid crystal composition comprising at least one compound according to claim 1 as a first component, and at least one compound selected from the group consisting of compounds having the general formulae (7), (8) and (9) as a second component:

(7)

(8)

(9)

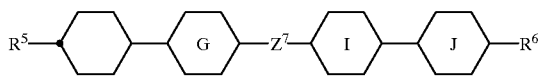

wherein R⁵ and R⁶ each independently denote an alkyl group having from 1 to 10 carbon atoms, in which optional non-adjacent methylene groups in said group may be replaced by oxygen atoms or —CH=CH— and optional hydrogen atoms in said group may be replaced by fluorine atoms, ring G, ring I and ring J each independently denote trans-1,4-cyclohexylene, pyrimidine-2,5-diyl or 1,4-phenylene in which one or more hydrogen atoms may be replaced by fluorine atoms, and Z⁷ and Z⁸ each independently denote —C≡C—, —COO—, —CH₂CH₂—, —CH=CH— or a covalent bond.

15. A liquid crystal composition comprising at least one compound according to claim 1 as a first component, at least one compound selected from the group consisting of compounds having the general formulae (5) and (6) as a second component, and at least one compound selected from the group consisting of compounds having the general formulae (7), (8) and (9) as a third component:

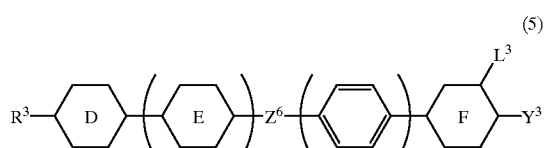

(5)

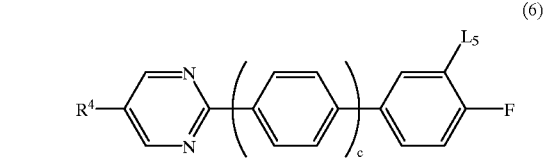

(6)

wherein R³ and R⁴ each independently denote an alkyl group having from 1 to 10 carbon atoms, in which optional non-adjacent methylene groups in said group may be replaced by oxygen atoms or —CH=CH— and optional hydrogen atoms in said group may be replaced by fluorine atoms, Y³ denotes CN group or C≡C—CN, ring D denotes trans-1,4-cyclohexylene, 1,4-phenylene, pyrimidine-2,5-diyl or 1,3-dioxane-2,5-diyl, ring E denotes trans-1,4-cyclohexylene, 1,4-phenylene in which hydrogen atoms may be replaced by fluorine atoms, or pyrimidine-2,5-diyl, ring F denotes trans-1,4-cyclohexylene or 1,4-phenylene, Z⁶ denotes —CH₂CH₂—, —COO— or a covalent bond, L³, L⁴ and L⁵ each independently denote a hydrogen atom or a fluorine atom, a, b and c each independently denote 0 or 1,

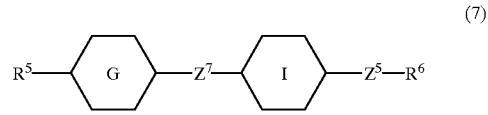

(7)

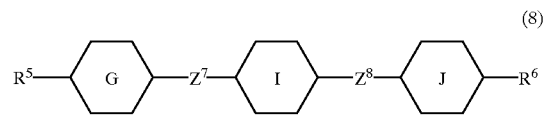

(8)

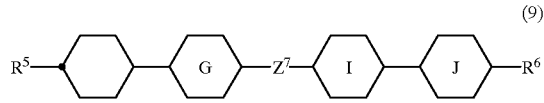

(9)

wherein R⁵ and R⁶ each independently denote an alkyl group having from 1 to 10 carbon atoms, in which optional non-adjacent methylene groups in said group may be replaced by oxygen atoms or —CH=CH— and optional hydrogen atoms in said group may be replaced by fluorine atoms, ring G, ring I and ring J each independently denote trans-1,4-cyclohexylene, pyrimidine-2,5-diyl or 1,4-phenylene in which one or more hydrogen atoms may be replaced by fluorine atoms, and Z⁷ and Z⁸ each independently denote —C≡C—, —COO—, —CH₂CH₂—, —CH=CH— or a covalent bond.

16. A liquid crystal composition comprising at least one compound according to claim 1 as a first component, at least one compound selected from the group consisting of compounds having the general formulae (2), (3) and (4) as a second component, at least one compound selected from the group consisting of compounds having the general formulae (5) and (6) as a third component, and at least one compound selected from the group consisting of compounds having the general formulae (7), (8) and (9) as a fourth component:

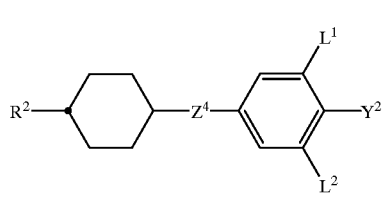

(2)

(3)

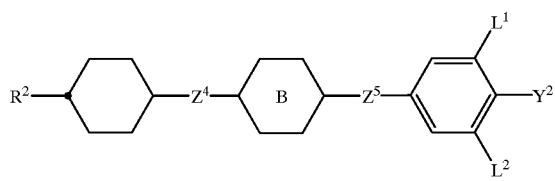

(4)

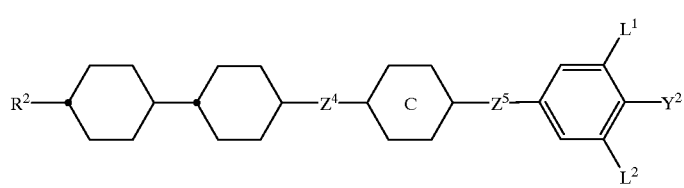

wherein $R^2$ denotes an alkyl group having from 1 to 10 carbon atoms, in which optional non-adjacent methylene groups in said group may be replaced by oxygen atoms or —CH=CH— and optional hydrogen atoms in said group may be replaced by fluorine atoms, $Y^2$ denotes a fluorine atom, a chlorine atom, $OCF_3$, $OCF_2H$, $CF_3$, $CF_2H$, $CFH_2$, $OCF_2CF_2H$ or $OCF_2CFHCF_3$, $L^1$ and $L^2$ each independently denote a hydrogen atom or a fluorine atom, $Z^4$ and $Z^5$ each independently denote —$CH_2CH_2$—, —CH=CH—, 1,4-butylene group, —COO—, —$CF_2O$—, —$OCF_2$— or a covalent bond, ring B denotes trans-1,4-cyclohexylene, 1,3-dioxane-2,5-diyl, or 1,4-phenylene in which hydrogen atoms may be replaced by fluorine atoms, and ring C denotes trans-1,4-cyclohexylene or 1,4-phenylene in which hydrogen atoms may be replaced by fluorine atoms, (5)

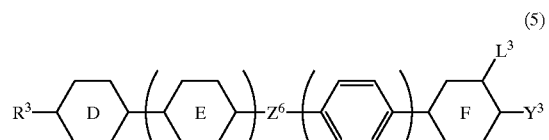

(6)

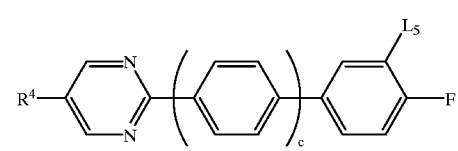

wherein $R^3$ and $R^4$ each independently denote an alkyl group having from 1 to 10 carbon atoms, in which optional non-adjacent methylene groups in said group may be replaced by oxygen atoms or —CH=CH— and optional hydrogen atoms in said group may be replaced by fluorine atoms, $Y^3$ denotes CN group or C≡C—CN, ring D denotes trans-1,4-cyclohexylene, 1,4-phenylene, pyrimidine-2,5-diyl or 1,3-dioxane-2,5-diyl, ring E denotes trans-1,4-cyclohexylene, 1,4-phenylene in which hydrogen atoms may be replaced by fluorine atoms, or pyrimidine-2,5-diyl, ring F denotes trans-1,4-cyclohexylene or 1,4-phenylene, $Z^6$ denotes —$CH_2CH_2$—, —COO— or a covalent bond, $L^3$, $L^4$ and $L^5$ each independently denote a hydrogen atom or a fluorine atom, a, b and c each independently denote 0 or 1, (7)

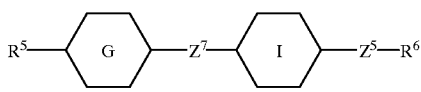

(8)

(9)

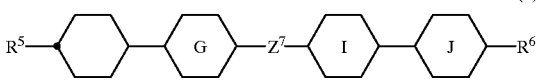

wherein $R^5$ and $R^6$ each independently denote an alkyl group having from 1 to 10 carbon atoms, in which optional non-adjacent methylene groups in said group may be replaced by oxygen atoms or —CH=CH— and optional hydrogen atoms in said group may be replaced by fluorine atoms, ring G, ring I and ring J each independently denote trans-1,4-cyclohexylene, pyrimidine-2,5-diyl or 1,4-phenylene in which one or more hydrogen atoms may be replaced by fluorine atoms, and $Z^7$ and $Z^8$ each independently denote —C≡C—, —COO—, —$CH_2CH_2$—, —CH=CH— or a covalent bond.

17. A liquid crystal composition comprising one or more optically active compounds in addition to the liquid crystal composition according to any one of claims 11 to 16.

18. A liquid crystal display element containing the liquid crystal composition according to any one of claims 11 to 16.

19. A liquid crystal display element containing the liquid crystal composition according to claim 17.

* * * * *